(12) United States Patent
Wawro et al.

(10) Patent No.: US 10,359,573 B2
(45) Date of Patent: *Jul. 23, 2019

(54) RESONANT WAVEGUIDE-GRANTING DEVICES AND METHODS FOR USING SAME

(71) Applicant: The Board of Regents of the University of Texas System, Austin, TX (US)

(72) Inventors: Debra D. Wawro, Arlington, TX (US); Sorin Tibuleac, Norcross, GA (US); Robert Magnusson, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/971,737

(22) Filed: Aug. 20, 2013

(65) Prior Publication Data
US 2014/0056559 A1 Feb. 27, 2014

Related U.S. Application Data

(60) Continuation of application No. 12/115,484, filed on May 5, 2008, now Pat. No. 8,514,391, which is a
(Continued)

(51) Int. Cl.
*G01J 3/00* (2006.01)
*G02B 6/34* (2006.01)
(Continued)

(52) U.S. Cl.
CPC ............ *G02B 6/34* (2013.01); *G01N 21/648* (2013.01); *G01N 21/7743* (2013.01);
(Continued)

(58) Field of Classification Search
CPC ............ G01N 21/7743; G01N 21/774; B01L 2300/0636; G02B 6/02061; G01H 9/004
(Continued)

(56) References Cited

U.S. PATENT DOCUMENTS

| 2,313,947 A | 3/1943 | Klinkum et al. ............. 359/454 |
| 3,017,512 A | 1/1962 | Wolbert ....................... 250/349 |

(Continued)

FOREIGN PATENT DOCUMENTS

| CA | 0591848 | 2/1960 |
| CA | 2395318 | 8/2001 |

(Continued)

OTHER PUBLICATIONS

"BIND® Technology," SRU Biosystems website located at http://www.srubiosystems.com/tech/index.html, downloaded on Aug. 12, 2009.
(Continued)

*Primary Examiner* — Michael A Lyons
(74) *Attorney, Agent, or Firm* — Norton Rose Fulbright US LLP

(57) ABSTRACT

Waveguide gratings, biosensors, and methods of using a waveguide grating, including as a biosensor.

7 Claims, 19 Drawing Sheets

Related U.S. Application Data continuation of application No. 11/305,065, filed on Dec. 16, 2005, now Pat. No. 7,400,399, which is a division of application No. 09/707,435, filed on Nov. 6, 2000, now Pat. No. 7,167,615.

(60) Provisional application No. 60/164,089, filed on Nov. 6, 1999, provisional application No. 60/163,705, filed on Nov. 5, 1999.

(51) Int. Cl.
- *G01N 21/64* (2006.01)
- *G01N 21/77* (2006.01)
- *G02B 6/02* (2006.01)
- *G02B 6/293* (2006.01)
- *G02B 6/12* (2006.01)

(52) U.S. Cl.
CPC .. *G01N 2021/7776* (2013.01); *G02B 6/02061* (2013.01); *G02B 6/29317* (2013.01); *G02B 2006/12107* (2013.01)

(58) Field of Classification Search
USPC .......................................... 356/300, 326, 328
See application file for complete search history.

(56) References Cited

U.S. PATENT DOCUMENTS

| | | | | |
|---|---|---|---|---|
| 3,197,432 | A | 7/1965 | Lamoreaux | 528/31 |
| 3,197,433 | A | 7/1965 | Lamoreaux | 528/31 |
| 3,220,972 | A | 11/1965 | Lamoreaux | 528/15 |
| 3,224,155 | A | 12/1965 | Rook | 52/592.6 |
| 3,240,754 | A | 3/1966 | Plueddemann et al. | 528/27 |
| 3,255,665 | A | 6/1966 | Weiher et al. | 359/595 |
| 3,300,418 | A | 1/1967 | Andres et al. | 521/103 |
| 3,322,962 | A | 5/1967 | Muller et al. | 250/559.01 |
| 3,468,771 | A | 9/1969 | Pedlow | 52/309.6 |
| 3,503,315 | A | 3/1970 | De Montebello | 396/330 |
| 3,530,779 | A | 9/1970 | Alofs | 396/330 |
| 3,544,190 | A | 12/1970 | Moorhusen et al. | 359/209.1 |
| 3,580,082 | A | 5/1971 | Strack | 73/705 |
| 3,591,252 | A | 7/1971 | Lu | 359/9 |
| 3,627,432 | A | 12/1971 | Bergmann | 356/246 |
| 3,628,872 | A | 12/1971 | Miranda et al. | 356/432 |
| 3,654,090 | A | 4/1972 | Wilhelmus et al. | 435/7.93 |
| 3,675,553 | A | 7/1972 | Dudley et al. | 396/330 |
| 3,683,773 | A | 8/1972 | Dudley et al. | 396/330 |
| 3,689,346 | A | 9/1972 | Rowland | 156/245 |
| 3,693,025 | A | 9/1972 | Brunton | 250/340 |
| 3,698,795 | A | 10/1972 | Flint | 359/571 |
| 3,706,486 | A | 12/1972 | De Montebello | 359/619 |
| 3,712,653 | A | 1/1973 | Lehmann | 52/582.2 |
| 3,715,334 | A | 2/1973 | Karstedt | 528/15 |
| 3,721,486 | A | 3/1973 | Bramley | 359/201.1 |
| 3,721,487 | A | 3/1973 | Pieuchard et al. | 359/17 |
| 3,740,155 | A | 6/1973 | Keller et al. | 356/409 |
| 3,748,975 | A | 7/1973 | Tarabocchia | 396/548 |
| 3,780,478 | A | 12/1973 | Pavlecka | 52/206 |
| 3,791,932 | A | 2/1974 | Schuurs et al. | 435/7.8 |
| 3,809,732 | A | 5/1974 | Chandross et al. | 430/321 |
| 3,810,688 | A | 5/1974 | Ballman et al. | 385/2 |
| 3,814,730 | A | 6/1974 | Karstedt | 528/15 |
| 3,820,294 | A | 6/1974 | Parker | 52/262 |
| 3,831,137 | A | 8/1974 | Cuomo | 367/153 |
| 3,839,067 | A | 10/1974 | Sosnowski et al. | 427/164 |
| 3,843,231 | A | 10/1974 | Borel et al. | 349/202 |
| 3,853,395 | A | 12/1974 | Yevick | 353/27 R |
| 3,856,404 | A | 12/1974 | Hershler | 356/36 |
| 3,856,604 | A | 12/1974 | Lukkarinen | 156/361 |
| 3,857,210 | A | 12/1974 | Austin | 52/4 |
| 3,875,714 | A | 4/1975 | Nayler et al. | 52/309.4 |
| 3,877,790 | A | 4/1975 | Robinson | 349/143 |
| 3,883,221 | A | 5/1975 | Rigrod | 385/36 |
| 3,883,222 | A | 5/1975 | Gunderson | 385/24 |
| 3,884,866 | A | 5/1975 | Jeram et al. | 523/203 |
| 3,896,661 | A | 7/1975 | Parkhurst et al. | 73/61.54 |
| 3,907,650 | A | 9/1975 | Pinsler et al. | 430/131 |
| 3,912,614 | A | 10/1975 | Spracklen et al. | 600/345 |
| 3,914,126 | A | 10/1975 | Pinsler et al. | 430/62 |
| 3,916,182 | A | 10/1975 | Dabby et al. | 250/199 |
| 3,916,482 | A | 11/1975 | Kvilhaug et al. | 452/152 |
| 3,926,564 | A | 12/1975 | Giaever | 422/426 |
| 3,932,763 | A | 1/1976 | Weinstein | 250/576 |
| 3,940,202 | A | 2/1976 | Kato et al. | 359/18 |
| 3,955,015 | A | 5/1976 | Ohtsuka et al. | 427/163.2 |
| 3,978,500 | A | 8/1976 | Brachet | 396/339 |
| 3,979,184 | A | 9/1976 | Giaever | 422/429 |
| 3,996,195 | A | 12/1976 | Sato et al. | 528/31 |
| 4,009,933 | A | 3/1977 | Firester | 359/485.03 |
| 4,013,463 | A | 3/1977 | Leder | 430/84 |
| 4,016,043 | A | 4/1977 | Schuurs et al. | 435/5 |
| 4,037,969 | A | 7/1977 | Feldman et al. | 356/401 |
| 4,045,927 | A | 9/1977 | Diaz | 52/127.11 |
| 4,050,895 | A | 9/1977 | Hardy et al. | 436/527 |
| 4,059,338 | A | 11/1977 | Hartelius | 385/36 |
| 4,067,639 | A | 1/1978 | Kramer | 359/211.4 |
| 4,075,062 | A | 2/1978 | Shibata et al. | 435/29 |
| 4,079,559 | A | 3/1978 | Tenbrummeler | 52/295 |
| 4,080,476 | A | 3/1978 | Laskey | 428/413 |
| 4,083,856 | A | 4/1978 | Mendicino | 549/215 |
| 4,093,346 | A | 6/1978 | Nishino et al. | 348/292 |
| 4,094,575 | A | 6/1978 | Kellie et al. | 359/10 |
| 4,094,576 | A | 6/1978 | Heiling | 359/18 |
| 4,094,585 | A | 6/1978 | Betensky | 359/708 |
| 4,098,655 | A | 7/1978 | Ward et al. | 205/85 |
| 4,104,070 | A | 8/1978 | Moritz et al. | 430/329 |
| 4,106,844 | A | 8/1978 | Bryngdahl et al. | 359/17 |
| 4,113,343 | A | 9/1978 | Pole et al. | 359/17 |
| 4,114,983 | A | 9/1978 | Maffitt et al. | 359/580 |
| 4,121,882 | A | 10/1978 | White | 359/17 |
| 4,125,314 | A | 11/1978 | Haskell et al. | 350/3.6 |
| 4,128,324 | A | 12/1978 | Seeger | 396/330 |
| 4,133,600 | A | 1/1979 | Russell et al. | 350/3.72 |
| 4,140,370 | A | 2/1979 | Snaper et al. | 350/128 |
| 4,152,075 | A | 5/1979 | Rellstab et al. | 356/435 |
| 4,153,367 | A | 5/1979 | Lietar et al. | 356/400 |
| 4,158,310 | A | 6/1979 | Ho | 76/705 |
| 4,162,243 | A | 7/1979 | Mi et al. | 260/37 S |
| 4,168,900 | A | 9/1979 | Adachi et al. | 355/1 |
| 4,200,110 | A | 4/1980 | Peterson et al. | 128/634 |
| 4,214,159 | A | 7/1980 | Hillenkamp et al. | 250/288 |
| 4,216,245 | A | 8/1980 | Johnson et al. | 427/2 |
| 4,229,073 | A | 10/1980 | Lotspeich et al. | 350/150 |
| 4,236,366 | A | 12/1980 | Rijnders et al. | 52/580 |
| 4,239,326 | A | 12/1980 | Kramer et al. | 999/999.99 |
| 4,240,751 | A | 12/1980 | Linnecke et al. | 356/409 |
| 4,243,293 | A | 1/1981 | Kramer et al. | 350/3.71 |
| 4,251,137 | A | 2/1981 | Knop et al. | 350/347 |
| 4,279,717 | A | 7/1981 | Eckberg et al. | 204/999.99 |
| 4,282,287 | A | 8/1981 | Giese et al. | 428/407 |
| 4,288,345 | A | 9/1981 | Ashby et al. | 252/999.99 |
| 4,289,371 | A | 9/1981 | Kramer et al. | 999/999.99 |
| RE30,804 | E | 11/1981 | Lindemann et al. | 999/410 |
| 4,312,228 | A | 1/1982 | Wohltjen et al. | 73/497 |
| 4,335,438 | A | 6/1982 | Smolen et al. | 364/497 |
| 4,343,536 | A | 8/1982 | Watanabe et al. | 999/355 |
| 4,344,438 | A | 8/1982 | Schultz et al. | 128/634 |
| 4,357,142 | A | 11/1982 | Schall et al. | 23/999.99 |
| 4,363,874 | A | 12/1982 | Greenquist et al. | 435/7 |
| 4,399,686 | A | 8/1983 | Kindlund et al. | 73/23 |
| 4,402,571 | A | 9/1983 | Cowan et al. | 999/999.99 |
| 4,416,505 | A | 11/1983 | Dickson et al. | 999/999.99 |
| 4,417,430 | A | 11/1983 | Loikitz et al. | 52/584 |
| 4,420,502 | A | 12/1983 | Conley et al. | 427/54.1 |
| 4,425,501 | A | 1/1984 | Stauffer et al. | 250/516 |
| 4,427,801 | A | 1/1984 | Sweet et al. | 523/212 |
| 4,440,850 | A | 4/1984 | Paul et al. | 430/325 |
| 4,447,546 | A | 5/1984 | Hirschfeld et al. | 436/527 |
| 4,448,485 | A | 5/1984 | Bergman et al. | 999/162.2 |
| 4,456,670 | A | 6/1984 | Shizuoka et al. | 430/49 |
| 4,461,533 | A | 7/1984 | Sherman et al. | 999/372 |
| 4,472,735 | A | 9/1984 | Shinozaki et al. | 358/47 |
| 4,496,216 | A | 1/1985 | Cowan et al. | 999/999.99 |

(56) References Cited

U.S. PATENT DOCUMENTS

| | | | |
|---|---|---|---|
| 4,499,052 A | 2/1985 | Fulwyler et al. | 422/52 |
| 4,502,756 A | 3/1985 | Peterson et al. | 999/162.2 |
| 4,512,122 A | 4/1985 | Berkowitz et al. | 52/127.9 |
| 4,513,593 A | 4/1985 | Wilson et al. | 70/114 |
| 4,521,522 A | 6/1985 | Lundstrom et al. | 436/525 |
| 4,531,809 A | 7/1985 | Carter et al. | 350/96.19 |
| 4,533,247 A | 8/1985 | Epworth | 356/345 |
| 4,534,356 A | 8/1985 | Papadakis et al. | 128/635 |
| 4,536,608 A | 8/1985 | Sheng et al. | 139/259 |
| 4,537,861 A | 8/1985 | Elings et al. | 436/518 |
| 4,556,621 A | 12/1985 | Hoffmann et al. | 430/49 |
| 4,557,993 A | 12/1985 | Matjakowski et al. | 430/131 |
| 4,558,012 A | 12/1985 | Nygren et al. | 436/501 |
| 4,558,014 A | 12/1985 | Hirschfeld et al. | 436/527 |
| 4,558,082 A | 12/1985 | Eckberg et al. | 524/104 |
| 4,560,246 A | 12/1985 | Cotter et al. | 999/96.16 |
| 4,560,248 A | 12/1985 | Cramp et al. | 999/999.99 |
| 4,560,249 A | 12/1985 | Nishiwaki et al. | 999/999.99 |
| 4,561,286 A | 12/1985 | Sekler et al. | 73/23 |
| 4,562,157 A | 12/1985 | Lowe et al. | 435/291 |
| 4,565,422 A | 1/1986 | Seymour et al. | 999/96.19 |
| 4,575,330 A | 3/1986 | Hull et al. | 425/174.4 |
| 4,576,850 A | 3/1986 | Martens et al. | 428/156 |
| 4,576,999 A | 3/1986 | Eckberg et al. | 525/476 |
| 4,582,809 A | 4/1986 | Block et al. | 436/527 |
| 4,586,980 A | 5/1986 | Hirai et al. | 156/655 |
| 4,591,260 A | 5/1986 | Yip et al. | 355/3 R |
| 4,596,697 A | 6/1986 | Ballato et al. | 422/98 |
| 4,598,240 A | 7/1986 | Gale et al. | 318/429 |
| 4,598,522 A | 7/1986 | Hoofe et al. | 52/555 |
| 4,608,344 A | 8/1986 | Carter et al. | 436/34 |
| 4,617,238 A | 10/1986 | Crivello et al. | 428/452 |
| 4,630,418 A | 12/1986 | Degut et al. | 52/264 |
| 4,632,522 A | 12/1986 | Osaka et al. | 999/570 |
| 4,637,684 A | 1/1987 | Tomita et al. | 999/96.19 |
| 4,647,521 A | 3/1987 | Oguchi et al. | 430/58 |
| 4,647,544 A | 3/1987 | Nicoli et al. | 436/518 |
| 4,650,329 A | 3/1987 | Barrett et al. | 356/345 |
| 4,652,290 A | 3/1987 | Cho et al. | 65/31 |
| 4,653,844 A | 3/1987 | Ward et al. | 999/96.15 |
| 4,653,849 A | 3/1987 | Boirat et al. | 999/96.22 |
| 4,653,850 A | 3/1987 | Boirat et al. | 999/96.22 |
| 4,654,532 A | 3/1987 | Hirschfeld et al. | 250/458.1 |
| 4,655,013 A | 4/1987 | Ritland et al. | 52/80 |
| 4,656,797 A | 4/1987 | Marquart et al. | 52/169.12 |
| 4,658,403 A | 4/1987 | Takiguchi et al. | 372/96 |
| 4,661,235 A | 4/1987 | Krull et al. | 204/414 |
| 4,666,745 A | 5/1987 | Huhn et al. | 427/393.4 |
| 4,668,063 A | 5/1987 | Street et al. | 999/112 |
| 4,668,558 A | 5/1987 | Barber et al. | 428/156 |
| 4,671,032 A | 6/1987 | Reynolds et al. | 52/210 |
| 4,673,299 A | 6/1987 | Dakin et al. | 374/131 |
| 4,674,878 A | 6/1987 | Vo-Dinh et al. | 356/301 |
| 4,678,904 A | 7/1987 | Saaski et al. | 250/227 |
| 4,682,895 A | 7/1987 | Costello et al. | 356/402 |
| 4,686,366 A | 8/1987 | Stuke et al. | 250/287 |
| 4,689,310 A | 8/1987 | Kramer et al. | 436/512 |
| 4,690,715 A | 9/1987 | Allara et al. | 148/999.99 |
| 4,691,994 A | 9/1987 | Afian et al. | 999/320 |
| 4,701,008 A | 10/1987 | Richard et al. | 999/96.12 |
| 4,701,392 A | 10/1987 | Saitoh et al. | 430/57 |
| 4,708,494 A | 11/1987 | Kleinerman et al. | 374/161 |
| 4,708,920 A | 11/1987 | Orensteen et al. | 430/11 |
| 4,716,121 A | 12/1987 | Block et al. | 436/514 |
| 4,721,764 A | 1/1988 | Fujiki et al. | 528/15 |
| 4,726,011 A | 2/1988 | Ih et al. | 370/3 |
| 4,729,640 A | 3/1988 | Sakata et al. | 999/348 |
| 4,729,949 A | 3/1988 | Weinreb et al. | 435/30 |
| 4,732,446 A | 3/1988 | Gipson et al. | 385/24 |
| 4,732,453 A | 3/1988 | De Montebello | 999/130 |
| 4,732,932 A | 3/1988 | Waldern et al. | 524/862 |
| 4,739,591 A | 4/1988 | Everhardus et al. | 51/319 |
| 4,743,377 A | 5/1988 | Ohtsu et al. | 210/635 |
| 4,747,667 A | 5/1988 | Tanaka et al. | 999/167 |
| 4,748,042 A | 5/1988 | Linnecke et al. | 427/2 |
| 4,751,509 A | 6/1988 | Kubota et al. | 340/784 |
| 4,753,529 A | 6/1988 | Layton | 356/345 |
| 4,758,090 A | 7/1988 | Schuma et al. | 356/350 |
| 4,763,009 A | 8/1988 | Fevrier et al. | 250/458.1 |
| 4,772,540 A | 9/1988 | Deutsch et al. | 430/320 |
| 4,773,063 A | 9/1988 | Maltenfort et al. | 370/3 |
| 4,776,660 A | 10/1988 | Mahlein et al. | 999/96.16 |
| 4,776,944 A | 10/1988 | Janata et al. | 204/415 |
| 4,778,987 A | 10/1988 | Saaski et al. | 250/226 |
| 4,785,814 A | 11/1988 | Kane et al. | 128/634 |
| 4,789,214 A | 12/1988 | Vilhelmsson et al. | 999/96.15 |
| 4,789,804 A | 12/1988 | Karube et al. | 310/311 |
| 4,791,069 A | 12/1988 | Hovorka et al. | 436/533 |
| 4,807,955 A | 2/1989 | Ashman et al. | 999/96.2 |
| 4,810,658 A | 3/1989 | Shanks et al. | 436/172 |
| 4,812,221 A | 3/1989 | Madou et al. | 204/412 |
| 4,815,843 A * | 3/1989 | Tiefenthaler et al. | 356/128 |
| 4,818,058 A | 4/1989 | Bonanni et al. | 999/96.2 |
| 4,818,710 A | 4/1989 | Sutherland et al. | 436/527 |
| 4,822,146 A | 4/1989 | Yamanobe et al. | 999/348 |
| 4,822,746 A | 4/1989 | Walt et al. | 436/528 |
| 4,823,403 A | 4/1989 | Twietmeyer et al. | 455/607 |
| 4,823,534 A | 4/1989 | Hebinck et al. | 52/743 |
| 4,824,789 A | 4/1989 | Yafuso et al. | 436/68 |
| 4,828,387 A | 5/1989 | Sawyers et al. | 356/319 |
| 4,837,715 A | 6/1989 | Ungpiyakul et al. | 364/552 |
| 4,839,250 A | 6/1989 | Cowan et al. | 430/1 |
| 4,842,783 A | 6/1989 | Blaylock et al. | 264/1.4 |
| 4,844,613 A | 7/1989 | Batchelder et al. | 356/318 |
| 4,850,681 A | 7/1989 | Yamanobe et al. | 999/348 |
| 4,851,091 A | 7/1989 | Uesugi et al. | 204/999.999 |
| 4,851,816 A | 7/1989 | Macias et al. | 340/573 |
| 4,852,967 A | 8/1989 | Cook et al. | 999/999.99 |
| 4,854,097 A | 8/1989 | Haener et al. | 52/309.11 |
| 4,857,273 A | 8/1989 | Stewart et al. | 422/68 |
| 4,857,828 A | 8/1989 | Celine et al. | 324/61 R |
| 4,859,022 A | 8/1989 | Opdahl et al. | 999/96.2 |
| 4,859,759 A | 8/1989 | Maycock et al. | 528/27 |
| 4,862,511 A | 8/1989 | Peppers et al. | 382/32 |
| RE33,064 E | 9/1989 | Carter et al. | 436/34 |
| 4,863,232 A | 9/1989 | Kwa et al. | 999/96.2 |
| 4,874,213 A | 10/1989 | Cowan et al. | 999/999.99 |
| 4,876,208 A | 10/1989 | Gustafson et al. | 436/531 |
| 4,877,745 A | 10/1989 | Hayes et al. | 436/166 |
| 4,877,747 A | 10/1989 | Stewart et al. | 436/525 |
| 4,882,288 A | 11/1989 | North et al. | 436/525 |
| 4,888,260 A | 12/1989 | Cowan et al. | 430/1 |
| 4,889,427 A | 12/1989 | Van Veen et al. | 356/445 |
| 4,894,343 A | 1/1990 | Tanaka et al. | 435/301 |
| 4,895,017 A | 1/1990 | Pyke et al. | 73/23 |
| 4,897,329 A | 1/1990 | Nakayama et al. | 430/49 |
| 4,901,306 A | 2/1990 | Gardner et al. | 370/3 |
| 4,907,973 A | 3/1990 | Hon et al. | 434/262 |
| 4,909,990 A | 3/1990 | Block et al. | 422/82.11 |
| 4,912,188 A | 3/1990 | Colas et al. | 528/15 |
| 4,913,531 A | 4/1990 | Efron et al. | 999/342 |
| 4,923,271 A | 5/1990 | Henry et al. | 999/96.19 |
| 4,926,412 A | 5/1990 | Jannson et al. | 370/3 |
| 4,927,898 A | 5/1990 | King et al. | 528/27 |
| 4,929,049 A | 5/1990 | Goullon et al. | 999/999.99 |
| 4,931,384 A | 6/1990 | Layton et al. | 435/7 |
| 4,945,230 A | 7/1990 | Saaski et al. | 250/227.21 |
| 4,945,245 A | 7/1990 | Levin et al. | 250/461.2 |
| 4,952,056 A | 8/1990 | Tiefenthaler | 356/73.1 |
| 4,955,060 A | 9/1990 | Katsuki et al. | 382/32 |
| 4,958,895 A | 9/1990 | Wells et al. | 999/98.12 |
| 4,966,430 A | 10/1990 | Weidel et al. | 999/96.11 |
| 4,967,531 A | 11/1990 | Giles et al. | 52/584 |
| 4,969,712 A | 11/1990 | Westwood et al. | 999/96.11 |
| 4,972,634 A | 11/1990 | Dresden et al. | 52/69 |
| 4,978,503 A | 12/1990 | Shanks et al. | 422/58 |
| 4,992,385 A | 2/1991 | Godfrey et al. | 436/525 |
| 4,997,278 A | 3/1991 | Finlan et al. | 356/128 |
| 4,998,396 A | 3/1991 | Palmersten et al. | 52/595 |
| 4,998,796 A | 3/1991 | Cowan et al. | 428/156 |
| 4,999,234 A | 3/1991 | Cowan et al. | 428/156 |
| 4,999,306 A | 3/1991 | Yafuso et al. | 436/68 |
| 5,002,867 A | 3/1991 | Macevicz et al. | 435/6 |
| 5,003,567 A | 3/1991 | Hawryluk et al. | 378/34 |

(56) References Cited

U.S. PATENT DOCUMENTS

| | | | |
|---|---|---|---|
| 5,004,348 A | 4/1991 | Magome et al. | 356/401 |
| 5,006,716 A | 4/1991 | Hall et al. | 250/458.1 |
| 5,009,477 A | 4/1991 | Alferness et al. | 999/96.14 |
| 5,014,478 A | 5/1991 | Spring et al. | 52/281 |
| 5,017,007 A | 5/1991 | Milne et al. | 356/301 |
| 5,017,009 A | 5/1991 | Schutt et al. | 356/338 |
| 5,023,053 A | 6/1991 | Finlan et al. | 422/82.05 |
| 5,026,139 A | 6/1991 | Klainer et al. | 999/999.99 |
| 5,028,545 A | 7/1991 | Soini et al. | 436/501 |
| 5,034,613 A | 7/1991 | Denk et al. | 250/458.1 |
| 5,035,863 A | 7/1991 | Finlan et al. | 422/82.05 |
| 5,042,897 A | 8/1991 | Meltz et al. | 999/96.19 |
| 5,045,694 A | 9/1991 | Beavis et al. | 250/287 |
| 5,046,800 A | 9/1991 | Blyler et al. | 999/96.12 |
| 5,047,213 A | 9/1991 | Finlan et al. | 422/82.11 |
| 5,050,955 A | 9/1991 | Sjolinder et al. | 999/96.2 |
| 5,055,265 A | 10/1991 | Finlan et al. | 422/82.05 |
| 5,055,383 A | 10/1991 | Koblinger et al. | 430/312 |
| 5,057,560 A | 10/1991 | Mueller et al. | 524/22 |
| 5,061,857 A | 10/1991 | Thompson et al. | 250/458.1 |
| 5,063,081 A | 11/1991 | Cozzette et al. | 427/2 |
| 5,063,559 A | 11/1991 | Marcuse et al. | 370/3 |
| 5,064,263 A | 11/1991 | Stein et al. | 999/96.11 |
| 5,064,619 A | 11/1991 | Finlan et al. | 422/82.05 |
| 5,069,263 A | 12/1991 | Edwards et al. | 160/135 |
| 5,071,248 A | 12/1991 | Tiefenthaler et al. | 356/128 |
| 5,073,000 A | 12/1991 | Definy et al. | 999/96.12 |
| 5,076,094 A | 12/1991 | Frye et al. | 73/19.03 |
| 5,082,629 A | 1/1992 | Burgess et al. | 422/82.11 |
| 5,082,630 A | 1/1992 | Partin et al. | 422/83 |
| 5,083,199 A | 1/1992 | Borner et al. | 358/88 |
| 5,093,876 A | 3/1992 | Henry et al. | 385/28 |
| 5,093,890 A | 3/1992 | Bregman et al. | 285/146 |
| 5,096,671 A | 3/1992 | Kane et al. | 422/82.07 |
| 5,098,659 A | 3/1992 | Yim et al. | 422/82.07 |
| 5,105,305 A | 4/1992 | Betzig et al. | 359/368 |
| 5,107,359 A | 4/1992 | Ohuchida et al. | 370/3 |
| 5,108,926 A | 4/1992 | Klebe et al. | 435/284 |
| 5,113,117 A | 5/1992 | Brooks et al. | 310/328 |
| 5,114,676 A | 5/1992 | Leiner et al. | 422/82.06 |
| 5,114,818 A | 5/1992 | Yu et al. | 430/97 |
| 5,114,864 A | 5/1992 | Walt et al. | 436/528 |
| 5,118,608 A | 6/1992 | Layton et al. | 435/7.1 |
| 5,118,937 A | 6/1992 | Hillenkamp et al. | 250/282 |
| 5,119,454 A | 6/1992 | Wills et al. | 385/14 |
| 5,120,131 A | 6/1992 | Lukosz et al. | 356/351 |
| 5,123,078 A | 6/1992 | Thomas et al. | 385/130 |
| 5,125,054 A | 6/1992 | Ackley et al. | 385/49 |
| 5,128,431 A | 7/1992 | Riding et al. | 528/15 |
| 5,133,892 A | 7/1992 | Chun et al. | 252/90 |
| 5,134,057 A | 7/1992 | Kuypers et al. | 430/325 |
| 5,135,876 A | 8/1992 | Andrade et al. | 436/518 |
| 5,142,385 A | 8/1992 | Anderson et al. | 359/10 |
| 5,142,920 A | 9/1992 | Bart et al. | 73/866 |
| 5,143,854 A | 9/1992 | Pirrung et al. | 436/518 |
| 5,148,302 A | 9/1992 | Nagano et al. | 359/95 |
| 5,152,758 A | 10/1992 | Kaetsu et al. | 604/890.1 |
| 5,152,962 A | 10/1992 | Lackie et al. | 422/58.1 |
| 5,155,785 A | 10/1992 | Holland et al. | 385/89 |
| 5,155,791 A | 10/1992 | Hsiung et al. | 385/122 |
| 5,156,785 A | 10/1992 | Zdrahala et al. | 264/108 |
| 5,157,537 A | 10/1992 | Rosenblatt et al. | 359/245 |
| 5,160,358 A | 11/1992 | Kondo et al. | 65/18.2 |
| 5,164,589 A | 11/1992 | Sjodin et al. | 250/227.24 |
| 5,166,023 A | 11/1992 | Harada et al. | 430/62 |
| 5,166,830 A | 11/1992 | Ishibai et al. | 359/717 |
| 5,166,990 A | 11/1992 | Riccitelli et al. | 385/12 |
| 5,170,448 A | 12/1992 | Ackley et al. | 385/31 |
| 5,173,747 A | 12/1992 | Boiarski et al. | 356/361 |
| 5,175,030 A | 12/1992 | Lu et al. | 428/30 |
| 5,176,970 A | 1/1993 | Hawryluk et al. | 430/5 |
| 5,177,012 A | 1/1993 | Kim et al. | 435/175 |
| 5,182,135 A | 1/1993 | Giesecke et al. | 427/98 |
| 5,186,897 A | 2/1993 | Eason et al. | 422/100 |
| 5,189,902 A | 3/1993 | Groeninger et al. | 73/24.06 |
| 5,190,350 A | 3/1993 | Hwang et al. | 297/380 |
| 5,192,502 A | 3/1993 | Attridge et al. | 422/57 |
| 5,194,300 A | 3/1993 | Cheung et al. | 427/213.31 |
| 5,194,393 A | 3/1993 | Hugl et al. | 436/525 |
| 5,195,161 A | 3/1993 | Adar et al. | 385/129 |
| 5,196,350 A | 3/1993 | Backman et al. | 436/501 |
| 5,206,706 A | 4/1993 | Quinn et al. | 356/400 |
| 5,206,920 A | 4/1993 | Cremer et al. | 385/37 |
| 5,208,111 A | 5/1993 | Decher et al. | 428/420 |
| 5,210,404 A | 5/1993 | Cush et al. | 250/216 |
| 5,212,577 A | 5/1993 | Nakamura et al. | 359/124 |
| 5,215,853 A | 6/1993 | Andrews et al. | 430/131 |
| 5,216,257 A | 6/1993 | Brueck et al. | 250/548 |
| 5,216,680 A | 6/1993 | Magnusson et al. | 372/20 |
| 5,222,902 A | 6/1993 | Piersch et al. | 446/121 |
| 5,226,100 A | 7/1993 | Maerz et al. | 385/45 |
| 5,229,614 A | 7/1993 | Andersson et al. | 250/370.12 |
| 5,229,833 A | 7/1993 | Stewart | 356/364 |
| 5,235,238 A | 8/1993 | Nomura et al. | 310/349 |
| 5,235,659 A | 8/1993 | Atkins et al. | 385/124 |
| 5,238,467 A | 8/1993 | Hashiba et al. | 51/293 |
| 5,242,828 A | 9/1993 | Bergstrom et al. | 435/291 |
| 5,244,636 A | 9/1993 | Walt et al. | 422/82.07 |
| 5,244,760 A | 9/1993 | Nealey et al. | 430/58 |
| 5,244,813 A | 9/1993 | Walt et al. | 436/172 |
| 5,245,466 A | 9/1993 | Burns et al. | 359/296 |
| 5,245,471 A | 9/1993 | Iwatsuka et al. | 359/494 |
| 5,250,264 A | 10/1993 | Walt et al. | 422/82.07 |
| 5,252,494 A | 10/1993 | Walt et al. | 436/528 |
| 5,252,743 A | 10/1993 | Barrett et al. | 548/303.7 |
| 5,253,037 A | 10/1993 | Kaliner et al. | 356/133 |
| 5,253,314 A | 10/1993 | Alferness et al. | 385/40 |
| 5,254,477 A | 10/1993 | Walt et al. | 436/172 |
| 5,255,075 A | 10/1993 | Cush | 356/445 |
| 5,260,029 A | 11/1993 | Hosoi et al. | 422/82.08 |
| 5,266,498 A | 11/1993 | Tarcha et al. | 436/525 |
| 5,268,306 A | 12/1993 | Berger et al. | 436/527 |
| 5,268,782 A | 12/1993 | Wenz et al. | 359/81 |
| 5,272,081 A | 12/1993 | Weinreb et al. | 435/240.1 |
| 5,278,608 A | 1/1994 | Taylor et al. | 355/22 |
| 5,279,912 A | 1/1994 | Telfer et al. | 430/17 |
| 5,280,172 A | 1/1994 | Di Bin et al. | 250/227.21 |
| 5,280,548 A | 1/1994 | Atwater et al. | 385/12 |
| 5,281,301 A | 1/1994 | Basavanhally et al. | 156/629 |
| 5,283,686 A | 2/1994 | Huber et al. | 359/337 |
| 5,287,427 A | 2/1994 | Atkins et al. | 385/124 |
| 5,289,407 A | 2/1994 | Strickler et al. | 365/106 |
| 5,291,574 A | 3/1994 | Levenson et al. | 385/129 |
| 5,294,402 A | 3/1994 | Schrepp et al. | 422/57 |
| 5,298,741 A | 3/1994 | Walt et al. | 250/227.23 |
| 5,300,263 A | 4/1994 | Hoopman et al. | 264/2.5 |
| 5,302,509 A | 4/1994 | Cheeseman et al. | 435/6 |
| 5,304,293 A | 4/1994 | Tierney et al. | 204/414 |
| 5,304,465 A | 4/1994 | Garland et al. | 435/4 |
| 5,304,492 A | 4/1994 | Klinkhammer et al. | 436/52 |
| 5,306,403 A | 4/1994 | Vo-Dinh et al. | 204/182.8 |
| 5,309,260 A | 5/1994 | Mizrahi et al. | 359/3 |
| 5,310,623 A | 5/1994 | Gal et al. | 430/321 |
| 5,310,674 A | 5/1994 | Weinreb et al. | 435/293 |
| 5,310,686 A | 5/1994 | Sawyers et al. | 436/518 |
| 5,312,729 A | 5/1994 | Allen et al. | 435/7.9 |
| 5,313,264 A | 5/1994 | Ivarsson et al. | 356/73 |
| 5,320,814 A | 6/1994 | Walt et al. | 422/82.07 |
| 5,324,933 A | 6/1994 | Berkcan et al. | 250/227.23 |
| 5,325,342 A | 6/1994 | Vo-Dinh et al. | 369/13 |
| 5,325,386 A | 6/1994 | Jewell et al. | 372/50 |
| 5,327,225 A | 7/1994 | Bender et al. | 356/445 |
| 5,327,515 A | 7/1994 | Anderson et al. | 385/123 |
| 5,331,654 A | 7/1994 | Jewell et al. | 372/45 |
| 5,332,643 A | 7/1994 | Harada et al. | 430/127 |
| 5,333,077 A | 7/1994 | Leger et al. | 359/619 |
| 5,334,303 A | 8/1994 | Muramatsu et al. | 204/412 |
| 5,335,066 A | 8/1994 | Yamada et al. | 356/364 |
| 5,337,146 A | 8/1994 | Azzam et al. | 356/367 |
| 5,337,183 A | 8/1994 | Rosenblatt et al. | 359/248 |
| 5,341,215 A | 8/1994 | Seher et al. | 356/445 |
| 5,342,737 A | 8/1994 | Goerger et al. | 430/324 |
| 5,343,292 A | 8/1994 | Brueck et al. | 356/363 |
| 5,343,542 A | 8/1994 | Kash et al. | 385/31 |

(56) References Cited

U.S. PATENT DOCUMENTS

| | | | |
|---|---|---|---|
| 5,344,784 A | 9/1994 | Attridge et al. | 436/518 |
| 5,349,796 A | 9/1994 | Meyerson et al. | 52/309.11 |
| 5,351,127 A | 9/1994 | King et al. | 356/445 |
| 5,351,324 A | 9/1994 | Forman et al. | 385/37 |
| 5,352,582 A | 10/1994 | Lichtenwalter et al. | 435/6 |
| 5,357,590 A | 10/1994 | Auracher et al. | 385/33 |
| 5,359,680 A | 10/1994 | Riviere et al. | 385/9 |
| 5,359,681 A | 10/1994 | Jorgenson et al. | 385/12 |
| 5,360,764 A | 11/1994 | Celotta et al. | 999/173 |
| 5,369,717 A | 11/1994 | Attridge et al. | 385/12 |
| 5,370,692 A | 12/1994 | Fink et al. | 623/16 |
| 5,373,359 A | 12/1994 | Woolam et al. | 356/328 |
| 5,374,563 A | 12/1994 | Maule et al. | 436/165 |
| 5,376,255 A | 12/1994 | Gumbrecht et al. | 204/426 |
| 5,376,556 A | 12/1994 | Tarcha et al. | 436/525 |
| 5,377,044 A | 12/1994 | Tomono et al. | 359/566 |
| H1398 H | 1/1995 | Campbell et al. | 435/6 |
| 5,380,489 A | 1/1995 | Sutton et al. | 422/68.1 |
| 5,380,589 A | 1/1995 | Goodman et al. | 428/36.92 |
| 5,384,464 A | 1/1995 | De Fornel et al. | 250/492.2 |
| 5,387,463 A | 2/1995 | Nakamura et al. | 428/327 |
| 5,389,943 A | 2/1995 | Brommer et al. | 343/909 |
| 5,395,587 A | 3/1995 | Brigham-Burke et al. | 422/68.1 |
| 5,400,136 A | 3/1995 | Vo-Dinh et al. | 356/301 |
| 5,401,600 A | 3/1995 | Aizawa et al. | 430/65 |
| 5,402,075 A | 3/1995 | Lu et al. | 324/664 |
| 5,404,756 A | 4/1995 | Briggs et al. | 73/719 |
| 5,410,016 A | 4/1995 | Hubbell et al. | 528/354 |
| 5,411,858 A | 5/1995 | McGeehan et al. | 435/4 |
| 5,412,743 A | 5/1995 | Brazas et al. | 385/2 |
| 5,413,884 A | 5/1995 | Koch et al. | 430/5 |
| 5,415,835 A | 5/1995 | Brueck et al. | 430/311 |
| 5,415,842 A | 5/1995 | Maule et al. | 422/82.05 |
| 5,418,136 A | 5/1995 | Miller et al. | 435/5 |
| 5,424,220 A | 6/1995 | Goerlach-Graw et al. | 436/518 |
| 5,425,124 A | 6/1995 | McRight et al. | 385/123 |
| 5,425,839 A | 6/1995 | Henck et al. | 156/650 |
| 5,430,813 A | 7/1995 | Anderson et al. | 385/12 |
| 5,430,815 A | 7/1995 | Shen et al. | 385/13 |
| 5,430,816 A | 7/1995 | Furuya et al. | 385/33 |
| 5,434,663 A | 7/1995 | Maule et al. | 356/300 |
| 5,434,709 A | 7/1995 | Yamada et al. | 359/569 |
| 5,435,109 A | 7/1995 | Kim et al. | 52/585.1 |
| 5,435,724 A | 7/1995 | Goodman et al. | 433/215 |
| 5,436,161 A | 7/1995 | Bergstrom et al. | 435/291 |
| 5,442,169 A | 8/1995 | Kunz | 250/227.21 |
| 5,443,791 A | 8/1995 | Catchcart et al. | 422/65 |
| 5,445,972 A | 8/1995 | Tarcha et al. | 436/544 |
| 5,449,625 A | 9/1995 | Kobayashi et al. | 436/518 |
| 5,451,683 A | 9/1995 | Barrett et al. | 548/302.7 |
| 5,455,178 A * | 10/1995 | Fattinger | 436/164 |
| 5,455,475 A | 10/1995 | Josse et al. | 310/316 |
| 5,457,573 A | 10/1995 | Iida et al. | 359/569 |
| 5,467,224 A | 11/1995 | Ohnishi et al. | 359/614 |
| 5,468,606 A | 11/1995 | Bogart et al. | 435/5 |
| 5,468,620 A | 11/1995 | Molloy | 435/7.1 |
| 5,474,815 A | 12/1995 | Sunderland et al. | 427/576 |
| 5,475,536 A | 12/1995 | Kikutani et al. | 359/794 |
| 5,475,780 A | 12/1995 | Mizrahi et al. | 385/37 |
| 5,478,527 A | 12/1995 | Gustafson et al. | 422/82.11 |
| 5,478,755 A | 12/1995 | Attridge et al. | 436/518 |
| 5,478,756 A | 12/1995 | Gizeli et al. | 436/527 |
| 5,479,544 A | 12/1995 | Ono et al. | 385/37 |
| 5,480,687 A | 1/1996 | Heming et al. | 427/573 |
| 5,481,629 A | 1/1996 | Tabuchi et al. | 385/14 |
| 5,482,830 A | 1/1996 | Bogart et al. | 435/5 |
| 5,482,867 A | 1/1996 | Barrett et al. | 436/518 |
| 5,485,277 A | 1/1996 | Foster et al. | 356/445 |
| 5,488,230 A | 1/1996 | Mizutani et al. | 250/548 |
| 5,489,678 A | 2/1996 | Fodor et al. | 536/22.1 |
| 5,489,988 A | 2/1996 | Ackley et al. | 356/436 |
| 5,491,556 A | 2/1996 | Stewart et al. | 356/445 |
| 5,492,840 A | 2/1996 | Malmqvist et al. | 436/518 |
| 5,494,798 A | 2/1996 | Gerdt et al. | 435/6 |
| 5,496,701 A | 3/1996 | Pollard-Knight et al. | 435/7.4 |
| 5,496,997 A | 3/1996 | Pope et al. | 250/227.21 |
| 5,506,141 A | 4/1996 | Weinreb et al. | 435/293 |
| 5,510,481 A | 4/1996 | Bednarski et al. | 536/120 |
| 5,512,131 A | 4/1996 | Kumar et al. | 156/655 |
| 5,512,490 A | 4/1996 | Walt et al. | 436/171 |
| 5,514,501 A | 5/1996 | Tarlov et al. | 430/5 |
| 5,514,559 A | 5/1996 | Markert-Hahn et al. | 435/7.9 |
| 5,515,461 A | 5/1996 | Deri et al. | 385/30 |
| 5,516,635 A | 5/1996 | Ekins et al. | 435/6 |
| 5,518,680 A | 5/1996 | Cima et al. | 264/401 |
| 5,518,863 A | 5/1996 | Pawluczyk et al. | 430/321 |
| 5,518,883 A | 5/1996 | Soini et al. | 435/6 |
| 5,527,711 A | 6/1996 | Tom-Moy et al. | 436/518 |
| 5,532,170 A | 7/1996 | Buckle et al. | 436/527 |
| 5,536,455 A | 7/1996 | Aoyama et al. | 264/1.7 |
| 5,543,966 A | 8/1996 | Meyers et al. | 359/566 |
| 5,548,404 A | 8/1996 | Kupershmidt et al. | 356/368 |
| 5,554,541 A | 9/1996 | Malmqvist et al. | 436/518 |
| 5,556,752 A | 9/1996 | Lockhart et al. | 435/6 |
| 5,559,338 A | 9/1996 | Elliott et al. | 250/492.1 |
| 5,565,324 A | 10/1996 | Still et al. | 435/6 |
| 5,568,606 A | 10/1996 | Dobbek et al. | 385/180 |
| 5,573,909 A | 11/1996 | Singer et al. | 435/6 |
| 5,573,956 A | 11/1996 | Hanning et al. | 436/518 |
| 5,575,849 A | 11/1996 | Honda et al. | 118/44 |
| 5,579,164 A | 11/1996 | Chapnik et al. | 359/618 |
| 5,580,697 A | 12/1996 | Keana et al. | 430/296 |
| 5,589,649 A | 12/1996 | Brinker et al. | 73/866 |
| 5,589,882 A | 12/1996 | Shiraishi et al. | 348/340 |
| 5,598,267 A | 1/1997 | Sambles et al. | 356/369 |
| 5,598,300 A | 1/1997 | Magnusson et al. | 359/566 |
| 5,599,695 A | 2/1997 | Pease et al. | 435/91.1 |
| 5,606,170 A | 2/1997 | Saaski et al. | 250/458.1 |
| 5,615,052 A | 3/1997 | Doggett et al. | 359/811 |
| 5,620,556 A | 4/1997 | Henck et al. | 156/626.1 |
| 5,620,850 A | 4/1997 | Bamdad et al. | 435/6 |
| 5,624,537 A | 4/1997 | Turner et al. | 204/403 |
| 5,629,214 A | 5/1997 | Crosby et al. | 436/518 |
| 5,631,170 A | 5/1997 | Attridge et al. | 436/518 |
| 5,631,171 A | 5/1997 | Sandstrom et al. | 436/518 |
| 5,631,734 A | 5/1997 | Stern et al. | 356/317 |
| 5,633,527 A | 5/1997 | Lear | 257/432 |
| 5,633,972 A | 5/1997 | Walt et al. | 385/116 |
| 5,634,159 A | 5/1997 | Paolo et al. | 396/327 |
| 5,638,174 A | 6/1997 | Henderson et al. | 356/343 |
| 5,639,603 A | 6/1997 | Dower et al. | 435/6 |
| 5,640,239 A | 6/1997 | Takamiya et al. | 356/345 |
| 5,641,640 A | 6/1997 | Hanning et al. | 435/7.92 |
| 5,641,956 A | 6/1997 | Vengsarkar et al. | 250/227.14 |
| 5,643,681 A | 7/1997 | Voorhees et al. | 428/483 |
| 5,646,400 A | 7/1997 | Perez et al. | 250/227.18 |
| 5,647,030 A | 7/1997 | Jorgenson et al. | 385/12 |
| 5,647,039 A | 7/1997 | Judkins et al. | 385/37 |
| 5,654,118 A | 8/1997 | Yuh et al. | 430/58 |
| 5,656,241 A | 8/1997 | Seifert et al. | 422/82.06 |
| 5,657,126 A | 8/1997 | Ducharmet et al. | 356/369 |
| 5,658,443 A | 8/1997 | Yamamoto et al. | 204/403 |
| 5,660,792 A | 8/1997 | Koike et al. | 422/63 |
| 5,663,790 A | 9/1997 | Ekstrom et al. | 356/128 |
| 5,666,197 A | 9/1997 | Guerra | 356/512 |
| 5,671,303 A | 9/1997 | Shieh et al. | 385/12 |
| 5,677,196 A | 10/1997 | Herron et al. | 436/518 |
| 5,680,252 A | 10/1997 | Sitter et al. | 359/566 |
| 5,690,894 A | 11/1997 | Pinkel et al. | 422/68.1 |
| 5,691,846 A | 11/1997 | Benson et al. | 359/530 |
| 5,700,241 A | 12/1997 | Goodman et al. | 604/93 |
| 5,702,915 A | 12/1997 | Miyamoto et al. | 435/32 |
| 5,703,978 A | 12/1997 | Digiovanni et al. | 385/37 |
| 5,712,705 A | 1/1998 | Fattinger et al. | 356/354 |
| 5,716,854 A | 2/1998 | Lofas et al. | 436/518 |
| 5,717,453 A | 2/1998 | Wohlstadter et al. | 348/46 |
| 5,719,060 A | 2/1998 | Hutchens et al. | 436/174 |
| 5,724,463 A | 3/1998 | Deacon et al. | 385/27 |
| 5,726,805 A | 3/1998 | Kaushik et al. | 359/589 |
| 5,732,173 A | 3/1998 | Bylander et al. | 385/49 |
| 5,734,772 A | 3/1998 | Gopalan et al. | 385/122 |
| 5,705,813 A | 4/1998 | Apffel et al. | 250/288 |
| 5,737,050 A | 4/1998 | Takahara et al. | 349/122 |

(56) References Cited

U.S. PATENT DOCUMENTS

| | | | |
|---|---|---|---|
| 5,738,825 A | 4/1998 | Rudigier et al. | 422/82.11 |
| 5,745,617 A | 4/1998 | Starodubov et al. | 385/37 |
| 5,755,501 A | 5/1998 | Shinohara et al. | 353/31 |
| 5,756,304 A | 5/1998 | Jovanovich et al. | 435/34 |
| 5,757,540 A | 5/1998 | Judkins et al. | 359/341 |
| 5,757,545 A | 5/1998 | Wu et al. | 359/463 |
| 5,758,461 A | 6/1998 | McManus et al. | 52/293.3 |
| 5,760,900 A | 6/1998 | Ito et al. | 356/338 |
| 5,768,461 A | 6/1998 | Svetkoff et al. | 385/116 |
| 5,770,306 A | 6/1998 | Suzuki et al. | 428/328 |
| 5,770,462 A | 6/1998 | Molloy et al. | 436/527 |
| 5,771,328 A | 6/1998 | Wortman et al. | 385/146 |
| 5,774,240 A | 6/1998 | Goto et al. | 359/12 |
| 5,779,978 A | 7/1998 | Hartmann et al. | 422/82.05 |
| 5,780,251 A | 7/1998 | Klainer et al. | 435/7.93 |
| 5,786,931 A | 7/1998 | Speckbacher et al. | 359/572 |
| 5,792,411 A | 8/1998 | Morris et al. | 267/400 |
| 5,793,544 A | 8/1998 | Ogihara et al. | 359/885 |
| 5,800,778 A | 9/1998 | Chen et al. | 422/48 |
| 5,800,992 A | 9/1998 | Fodor et al. | 435/6 |
| 5,801,390 A | 9/1998 | Shiraishi et al. | 250/559.3 |
| 5,804,453 A | 9/1998 | Chen et al. | 436/518 |
| 5,808,256 A | 9/1998 | Kira et al. | 204/157.15 |
| 5,812,571 A | 9/1998 | Peters | 372/36 |
| 5,814,516 A | 9/1998 | Vo-Dinh et al. | 435/287.2 |
| 5,814,524 A | 9/1998 | Walt et al. | 436/518 |
| 5,821,343 A | 10/1998 | Keogh et al. | 530/402 |
| 5,822,472 A | 10/1998 | Danielzik et al. | 385/12 |
| 5,830,539 A | 11/1998 | Yan et al. | 427/551 |
| 5,830,645 A | 11/1998 | Pinkel et al. | 435/6 |
| 5,830,762 A | 11/1998 | Weindel et al. | 436/8 |
| 5,830,766 A | 11/1998 | Attridge et al. | 436/510 |
| 5,832,165 A | 11/1998 | Reichert et al. | 385/130 |
| 5,837,860 A | 11/1998 | Anderson et al. | 536/25.3 |
| 5,840,484 A | 11/1998 | Seilhamer et al. | 435/6 |
| 5,846,842 A | 12/1998 | Herron et al. | 436/518 |
| 5,846,843 A | 12/1998 | Simon et al. | 436/527 |
| 5,849,035 A | 12/1998 | Pathak et al. | 623/7 |
| 5,849,208 A | 12/1998 | Hayes et al. | 216/94 |
| 5,853,894 A | 12/1998 | Brown et al. | 428/422 |
| 5,858,746 A | 1/1999 | Hubbell et al. | 435/177 |
| 5,858,799 A | 1/1999 | Yee et al. | 436/164 |
| 5,858,801 A | 1/1999 | Brizzolara et al. | 436/518 |
| 5,863,449 A | 1/1999 | Grabbe | 216/24 |
| 5,863,708 A | 1/1999 | Zanzucchi et al. | 430/320 |
| 5,864,641 A | 1/1999 | Murphy et al. | 385/12 |
| 5,872,010 A | 2/1999 | Karger et al. | 436/173 |
| 5,873,394 A | 2/1999 | Meltzer et al. | 141/130 |
| 5,874,219 A | 2/1999 | Rava et al. | 435/6 |
| 5,888,723 A | 3/1999 | Sutton et al. | 435/5 |
| 5,891,658 A | 4/1999 | Klainer et al. | 435/7.93 |
| 5,891,747 A | 4/1999 | Farah | 438/31 |
| 5,897,304 A | 4/1999 | Kaneko et al. | 417/552 |
| 5,898,503 A | 4/1999 | Keller et al. | 356/445 |
| 5,900,481 A | 5/1999 | Lough et al. | 536/55.3 |
| 5,907,408 A | 5/1999 | Naya et al. | 356/445 |
| 5,912,456 A | 6/1999 | Melendez et al. | 250/216 |
| 5,917,607 A | 6/1999 | Naya et al. | 356/445 |
| 5,922,550 A | 7/1999 | Everhart et al. | 435/7.21 |
| 5,925,878 A | 7/1999 | Challener | 250/225 |
| 5,933,276 A | 8/1999 | Magee et al. | 359/455 |
| 5,946,083 A | 8/1999 | Melendez et al. | 356/73 |
| 5,955,335 A | 9/1999 | Thus et al. | 435/176 |
| 5,955,378 A | 9/1999 | Challener | 436/535 |
| 5,955,729 A | 9/1999 | Nelson et al. | 250/282 |
| 5,959,292 A | 9/1999 | Duveneck et al. | 250/227.1 |
| 5,961,926 A | 10/1999 | Kolb et al. | 422/101 |
| 5,965,456 A | 10/1999 | Malmqvist et al. | 436/514 |
| 5,969,863 A | 10/1999 | Staub et al. | 359/567 |
| 5,972,199 A | 10/1999 | Heller et al. | 205/777.5 |
| 5,972,612 A | 10/1999 | Malmqvist et al. | 435/6 |
| 5,978,159 A | 11/1999 | Kamo et al. | 359/793 |
| 5,978,401 A | 11/1999 | Morgan | 372/50 |
| 5,978,524 A | 11/1999 | Bischel et al. | 385/4 |
| 5,981,956 A | 11/1999 | Stern et al. | 250/458.1 |
| 5,986,762 A | 11/1999 | Challener | 356/375 |
| 5,991,048 A | 11/1999 | Karlsen et al. | 356/445 |
| 5,991,480 A | 11/1999 | Kunz et al. | 385/37 |
| 5,991,482 A | 11/1999 | Laude et al. | 385/37 |
| 5,994,150 A | 11/1999 | Challenger et al. | 436/518 |
| 5,995,279 A | 11/1999 | Ogino et al. | 359/355 |
| 5,995,304 A | 11/1999 | Nomura et al. | 359/726 |
| 5,998,298 A | 12/1999 | Fleming et al. | 438/692 |
| 5,998,597 A | 12/1999 | Fisher et al. | 536/23.1 |
| RE36,529 E | 1/2000 | Lewis et al. | 356/346 |
| 6,020,047 A | 2/2000 | Everhart et al. | 428/209 |
| 6,035,089 A | 3/2000 | Grann et al. | 385/129 |
| 6,041,071 A | 3/2000 | Tayebati et al. | 372/64 |
| 6,042,998 A | 3/2000 | Brueck et al. | 430/316 |
| 6,045,755 A | 4/2000 | Lebl et al. | 422/65 |
| 6,052,188 A | 4/2000 | Fluckiger et al. | 356/369 |
| 6,052,213 A | 4/2000 | Burt et al. | 359/237 |
| 6,055,262 A | 4/2000 | Cox et al. | 372/96 |
| 6,060,256 A | 5/2000 | Everhart et al. | 435/7.21 |
| 6,064,524 A | 5/2000 | Oka et al. | 359/582 |
| 6,076,248 A | 6/2000 | Hoopman et al. | 29/527.1 |
| 6,078,705 A | 6/2000 | Neuschafer et al. | 385/12 |
| 6,087,114 A | 7/2000 | Rider et al. | 435/7.2 |
| 6,088,505 A | 7/2000 | Hobbs et al. | 385/147 |
| 6,093,536 A | 7/2000 | Drake et al. | 435/6 |
| 6,096,127 A | 8/2000 | Dimos et al. | 117/9 |
| 6,100,991 A | 8/2000 | Challener | 356/445 |
| 6,102,885 A | 8/2000 | Bass et al. | 604/22 |
| 6,111,248 A | 8/2000 | Melendez et al. | 250/239 |
| 6,111,652 A | 8/2000 | Melendez et al. | 356/445 |
| 6,113,559 A | 9/2000 | Klopotek et al. | 601/2 |
| 6,118,597 A | 9/2000 | Maruyama et al. | 359/743 |
| 6,121,048 A | 9/2000 | Zaffaroni et al. | 436/45 |
| 6,127,183 A | 10/2000 | Ivarsson et al. | 436/34 |
| 6,128,431 A | 10/2000 | Siminovitch et al. | 385/147 |
| 6,137,576 A | 10/2000 | Pauluth et al. | 356/361 |
| 6,141,096 A | 10/2000 | Stern et al. | 356/318 |
| 6,143,574 A | 11/2000 | Karlsson et al. | 436/517 |
| 6,146,593 A | 11/2000 | Pinkel et al. | 422/68.1 |
| 6,147,732 A | 11/2000 | Aoyama et al. | 349/112 |
| 6,154,480 A | 11/2000 | Magnusson et al. | 372/96 |
| 6,164,785 A | 12/2000 | Maekawa et al. | 359/613 |
| 6,174,677 B1 | 1/2001 | Vo-Dinh et al. | 435/6 |
| 6,183,696 B1 | 2/2001 | Elkind et al. | 422/82.05 |
| 6,185,019 B1 | 2/2001 | Hobbs et al. | 359/30 |
| 6,191,847 B1 | 2/2001 | Melendez et al. | 356/73 |
| 6,191,890 B1 | 2/2001 | Baets et al. | 359/572 |
| 6,198,869 B1 | 3/2001 | Kraus et al. | 385/129 |
| 6,200,737 B1 | 3/2001 | Walt et al. | 430/320 |
| 6,200,814 B1 | 3/2001 | Malmqvist et al. | 436/52 |
| 6,203,759 B1 | 3/2001 | Pelc et al. | 422/100 |
| 6,203,989 B1 | 3/2001 | Goldberg et al. | 435/6 |
| 6,207,031 B1 | 3/2001 | Adourian et al. | 204/451 |
| 6,207,381 B1 | 3/2001 | Larsson et al. | 435/6 |
| 6,207,960 B1 | 3/2001 | Stern et al. | 250/458.1 |
| 6,211,954 B1 | 4/2001 | Danielzik et al. | 356/317 |
| 6,212,312 B1 | 4/2001 | Grann et al. | 385/24 |
| 6,215,928 B1 | 4/2001 | Friesem et al. | 385/37 |
| 6,218,194 B1 | 4/2001 | Lyndin et al. | 436/518 |
| 6,220,075 B1 | 4/2001 | Papen et al. | 73/1.74 |
| 6,221,579 B1 | 4/2001 | Everhart et al. | 435/5 |
| 6,225,244 B1 | 5/2001 | Oguma et al. | 501/45 |
| 6,225,625 B1 | 5/2001 | Pirrung et al. | 250/302 |
| 6,235,488 B1 | 5/2001 | Tom-Moy et al. | 435/7.5 |
| 6,239,876 B1 | 5/2001 | Brandenberg et al. | 356/451 |
| 6,245,578 B1 | 6/2001 | Molloy et al. | 436/527 |
| 6,252,236 B1 | 6/2001 | Trulson et al. | 250/458.1 |
| 6,277,653 B1 | 8/2001 | Challener et al. | 436/518 |
| 6,285,500 B1 | 9/2001 | Ranalli et al. | 359/497 |
| 6,288,842 B1 | 9/2001 | Florczak et al. | 359/619 |
| 6,289,144 B1 | 9/2001 | Neuschafer et al. | 385/12 |
| 6,289,286 B1 | 9/2001 | Andersson et al. | 702/19 |
| 6,294,327 B1 | 9/2001 | Walton et al. | 435/6 |
| 6,303,179 B1 | 10/2001 | Koulik et al. | 623/11.11 |
| 6,304,312 B1 | 10/2001 | Tanabe et al. | 349/201 |
| 6,316,153 B1 | 11/2001 | Goodman et al. | 430/8 |
| 6,320,991 B1 | 11/2001 | Callener et al. | 385/12 |
| 6,324,010 B1 | 11/2001 | Bowen et al. | 359/622 |
| RE37,473 E | 12/2001 | Challener et al. | 250/225 |

(56) References Cited

U.S. PATENT DOCUMENTS

| | | | |
|---|---|---|---|
| 6,332,663 B1 | 12/2001 | Puzio | 347/19 |
| 6,338,968 B1 | 1/2002 | Hefti et al. | 436/518 |
| 6,340,598 B1 | 1/2002 | Herron et al. | 436/518 |
| 6,346,376 B1 | 2/2002 | Sigrist et al. | 435/5 |
| 6,355,393 B1 | 3/2002 | Hirai et al. | 430/202 |
| 6,377,721 B1 | 4/2002 | Walt et al. | 385/12 |
| 6,395,558 B1 | 5/2002 | Duveneck et al. | 436/172 |
| 6,399,295 B1 | 6/2002 | Kaylor et al. | 435/5 |
| 6,404,554 B1 | 6/2002 | Lee et al. | 359/576 |
| 6,429,022 B1 | 8/2002 | Kunz et al. | 436/164 |
| 6,449,097 B1 | 9/2002 | Zhu et al. | 359/576 |
| 6,483,959 B1 | 11/2002 | Singh | 385/12 |
| 6,488,414 B1 | 12/2002 | Dawes et al. | 385/79 |
| 6,493,097 B1 | 12/2002 | Ivarsson et al. | 356/630 |
| 6,528,142 B2 | 3/2003 | Ikegaya et al. | 428/169 |
| 6,532,326 B1 | 3/2003 | Hutchinson et al. | 385/12 |
| 6,558,957 B1 | 5/2003 | Roinestad et al. | 422/82.05 |
| 6,563,559 B2 | 5/2003 | Noritake et al. | 349/113 |
| 6,570,657 B1 | 5/2003 | Hoppe et al. | 356/445 |
| 6,573,040 B2 | 6/2003 | Everhart et al. | 435/5 |
| 6,579,673 B2 | 6/2003 | McGrath et al. | 435/5 |
| 6,587,276 B2 | 7/2003 | Daniell et al. | 359/622 |
| 6,618,116 B1 | 9/2003 | Murata et al. | 349/201 |
| 6,661,952 B2 | 12/2003 | Simpson et al. | 385/11 |
| 6,665,070 B1 | 12/2003 | Yarussi et al. | 356/327 |
| 6,667,159 B1 | 12/2003 | Walt et al. | 514/100 |
| 6,707,561 B1 | 3/2004 | Budach | 356/521 |
| 6,741,307 B2 | 5/2004 | Matsunaga et al. | 349/112 |
| 6,748,138 B2 | 6/2004 | Wang et al. | 385/10 |
| 6,771,376 B2 | 8/2004 | Budach | 356/521 |
| 6,855,329 B1 | 2/2005 | Shakesheff et al. | 424/409 |
| 6,861,121 B2 | 3/2005 | Matsunaga et al. | 428/141 |
| 6,867,869 B2 | 3/2005 | Budach | 356/521 |
| 6,870,624 B2 | 3/2005 | Hobbs et al. | 356/416 |
| 6,870,630 B2 | 3/2005 | Budach et al. | 356/521 |
| 6,901,194 B2 | 5/2005 | Charlton et al. | 385/12 |
| 6,902,703 B2 | 6/2005 | Marquiss et al. | 422/100 |
| 6,951,715 B2 | 10/2005 | Cunningham et al. | 435/4 |
| 6,990,259 B2 | 1/2006 | Cunningham | 385/12 |
| 7,023,544 B2 | 4/2006 | Cunningham et al. | 356/326 |
| 7,064,844 B2 | 6/2006 | Budach | 356/521 |
| 7,070,987 B2 | 7/2006 | Cunningham et al. | 435/287.1 |
| 7,074,311 B1 | 7/2006 | Cunningham | 204/450 |
| 7,075,654 B2 | 7/2006 | Kubo | 356/445 |
| 7,094,595 B2 | 8/2006 | Cunningham et al. | 435/287.2 |
| 7,101,660 B2 | 9/2006 | Cunningham et al. | 435/4 |
| 7,118,710 B2 | 10/2006 | Cunningham et al. | 422/82.07 |
| 7,142,296 B2 | 11/2006 | Cunningham et al. | 356/326 |
| 7,142,298 B2 | 11/2006 | Nuspliger | 356/338 |
| 7,148,964 B2 | 12/2006 | Cunningham | 356/326 |
| 7,153,702 B2 | 12/2006 | Lin et al. | 436/518 |
| 7,158,230 B2 | 1/2007 | Cunningham et al. | 356/326 |
| 7,162,125 B1 | 1/2007 | Schulz et al. | 385/37 |
| 7,167,615 B1 | 1/2007 | Wawro et al. | 385/37 |
| 7,170,599 B2 | 1/2007 | Cunningham et al. | 356/326 |
| 7,175,980 B2 | 2/2007 | Qiu et al. | 435/6 |
| 7,197,198 B2 | 3/2007 | Schulz et al. | 385/12 |
| 7,202,076 B2 | 4/2007 | Cunningham et al. | 436/524 |
| 7,217,574 B2 | 5/2007 | Pien et al. | 436/164 |
| 7,264,973 B2 | 9/2007 | Lin et al. | 436/518 |
| 7,267,993 B2 | 9/2007 | Pentrenko | 436/518 |
| 7,292,336 B2 | 11/2007 | Cunningham et al. | 356/326 |
| 7,298,477 B1 | 11/2007 | Cunningham et al. | 356/326 |
| 7,300,803 B2 | 11/2007 | Lin et al. | 436/518 |
| 7,301,628 B2 | 11/2007 | Cunningham et al. | 356/326 |
| 7,306,827 B2 | 12/2007 | Li et al. | 427/264 |
| 7,309,604 B2 | 12/2007 | Alitalo et al. | 435/325 |
| 7,309,614 B1 | 12/2007 | Baird | 436/518 |
| 7,312,090 B2 | 12/2007 | Lin et al. | 435/7.2 |
| 7,327,454 B2 | 2/2008 | Cunningham et al. | 356/326 |
| 7,371,562 B2 | 5/2008 | Cunningham et al. | 436/518 |
| 7,396,675 B2 | 7/2008 | Pawlak | 435/287.2 |
| 7,400,399 B2 * | 7/2008 | Wawro et al. | 356/328 |
| 7,422,891 B2 | 9/2008 | Cunningham et al. | 435/287.2 |
| 7,429,492 B2 | 9/2008 | Lin | 436/518 |
| 7,435,385 B2 | 10/2008 | Lin | 422/82.05 |
| 7,479,404 B2 | 1/2009 | Cunningham | 438/69 |
| 7,483,127 B1 | 1/2009 | Li | 356/237.1 |
| 7,497,992 B2 | 3/2009 | Cunningham | 422/82.05 |
| 7,521,769 B2 | 4/2009 | Cunningham | 257/414 |
| 7,524,625 B2 | 4/2009 | Madison | 435/5 |
| 7,534,578 B1 | 5/2009 | Baird | 435/7.4 |
| 7,620,276 B2 | 11/2009 | Schulz | 385/37 |
| 7,628,085 B2 | 12/2009 | Laing | 73/863 |
| 7,689,086 B2 | 3/2010 | Magnusson et al. | 385/129 |
| 7,742,662 B2 | 6/2010 | Cunningham | 385/12 |
| 7,756,365 B2 | 7/2010 | Cunningham | 385/12 |
| 7,790,406 B2 | 9/2010 | Cunningham | 435/7.2 |
| 8,514,391 B2 * | 8/2013 | Wawro et al. | 356/300 |
| 2002/0018610 A1 | 2/2002 | Challener et al. | 385/12 |
| 2002/0028480 A1 | 3/2002 | Maher | 435/285.2 |
| 2002/0123050 A1 | 9/2002 | Poponin et al. | 435/6 |
| 2002/0127565 A1 | 9/2002 | Cunningham et al. | 435/287.2 |
| 2002/0135752 A1 | 9/2002 | Valentin et al. | 356/369 |
| 2002/0142133 A1 | 10/2002 | Matsunaga et al. | 428/141 |
| 2002/0150722 A1 | 10/2002 | Suzuki et al. | 428/332 |
| 2002/0168295 A1 | 11/2002 | Cunningham et al. | 422/82.07 |
| 2002/0171045 A1 | 11/2002 | Perraut et al. | 436/172 |
| 2003/0003599 A1 | 1/2003 | Wagner et al. | 436/100 |
| 2003/0017580 A1 | 1/2003 | Cunningham et al. | 435/6 |
| 2003/0017581 A1 | 1/2003 | Li et al. | 427/264 |
| 2003/0026891 A1 | 2/2003 | Qiu et al. | 435/6 |
| 2003/0027327 A1 | 2/2003 | Cunningham et al. | 435/4 |
| 2003/0027328 A1 | 2/2003 | Cunningham et al. | 435/287.1 |
| 2003/0032039 A1 | 2/2003 | Cunningham et al. | 356/326 |
| 2003/0059855 A1 | 3/2003 | Cunningham et al. | 356/326 |
| 2003/0068657 A1 | 4/2003 | Lin et al. | 436/518 |
| 2003/0077660 A1 | 4/2003 | Pien et al. | 436/164 |
| 2003/0092075 A1 | 5/2003 | Pepper et al. | 436/518 |
| 2003/0104479 A1 | 6/2003 | Bright | 435/320.1 |
| 2003/0113766 A1 | 6/2003 | Pepper et al. | 435/6 |
| 2003/0148542 A1 | 8/2003 | Pawlak et al. | 435/6 |
| 2003/0210396 A1 | 11/2003 | Hobbs et al. | 356/416 |
| 2003/0224369 A1 | 12/2003 | Surber | 435/6 |
| 2004/0005540 A1 | 1/2004 | Petrenko | 435/5 |
| 2004/0011965 A1 | 1/2004 | Hodgkinson et al. | 250/461.1 |
| 2004/0132172 A1 | 7/2004 | Lin et al. | 422/82.05 |
| 2004/0132214 A1 | 7/2004 | Lin et al. | 436/518 |
| 2004/0151626 A1 | 8/2004 | Cunningham et al. | 436/524 |
| 2004/0191757 A1 | 9/2004 | Maher | 435/7.2 |
| 2005/0200942 A1 | 9/2005 | Grot et al. | 385/123 |
| 2005/0214803 A1 | 9/2005 | Wang | 436/518 |
| 2005/0227374 A1 | 10/2005 | Cunningham et al. | 435/287.2 |
| 2006/0003372 A1 | 1/2006 | Li | 435/6 |
| 2006/0024013 A1 | 2/2006 | Magnusson et al. | 385/129 |
| 2006/0030033 A1 | 2/2006 | Cunningham et al. | 436/164 |
| 2006/0040376 A1 | 2/2006 | Cunningham et al. | 436/518 |
| 2006/0057707 A1 | 3/2006 | Cunningham et al. | 436/524 |
| 2006/0181705 A1 | 3/2006 | Cunningham et al. | 436/524 |
| 2006/0193550 A1 | 8/2006 | Wawro et al. | 356/328 |
| 2006/0275825 A1 | 12/2006 | Laing | 436/524 |
| 2006/0281077 A1 | 12/2006 | Lin et al. | 435/7.2 |
| 2006/0286663 A1 | 12/2006 | Cunningham et al. | 435/4 |
| 2007/0041012 A1 | 2/2007 | Cunningham et al. | 356/326 |
| 2007/0054339 A1 | 3/2007 | Lin et al. | 436/518 |
| 2007/0070355 A1 | 3/2007 | Cunningham et al. | 356/326 |
| 2007/0141231 A1 | 6/2007 | Qiu et al. | 435/4 |
| 2008/0062418 A1 | 3/2008 | Magnusson et al. | 356/307 |
| 2008/0213910 A1 | 9/2008 | Jogikalmath | 436/94 |
| 2008/0219892 A1 | 9/2008 | Cunningham | 435/287.1 |
| 2008/0240543 A1 | 10/2008 | Budach | 382/141 |
| 2008/0299673 A1 | 12/2008 | Wagner | 436/171 |
| 2008/0316485 A1 | 12/2008 | Wawro et al. | 356/328 |
| 2009/0017488 A1 | 1/2009 | Binder | 506/7 |
| 2009/0067774 A1 | 3/2009 | Magnusson | 385/10 |
| 2009/0130703 A1 | 5/2009 | Wagner | 435/7.2 |
| 2009/0137422 A1 | 6/2009 | Laing | 506/7 |
| 2009/0148955 A1 | 6/2009 | Cunningham | 436/524 |
| 2009/0176658 A1 | 7/2009 | Madison | 436/512 |
| 2009/0179637 A1 | 7/2009 | Cunningham | 436/524 |
| 2009/0192049 A1 | 7/2009 | Laing | 436/524 |
| 2009/0264314 A1 | 10/2009 | Cunningham | 435/287.2 |
| 2009/0269244 A1 | 10/2009 | Cunningham | 422/82.05 |
| 2009/0282931 A1 | 11/2009 | Laing | 73/863 |

(56) References Cited

U.S. PATENT DOCUMENTS

| | | | |
|---|---|---|---|
| 2009/0305304 A1 | 12/2009 | Laing | 435/7.2 |
| 2010/0003743 A1 | 1/2010 | Schulz et al. | 435/288.7 |
| 2010/0008826 A1 | 1/2010 | Schulz | 422/102 |
| 2010/0015721 A1 | 2/2010 | Laing | 436/164 |
| 2010/0043571 A1 | 2/2010 | Laing | 73/863 |
| 2010/0143959 A1 | 6/2010 | Cunningham | 435/7.2 |
| 2010/0195099 A1 | 8/2010 | Rockney | 356/326 |
| 2010/0196925 A1 | 8/2010 | Genick | 436/518 |
| 2010/0202923 A1 | 8/2010 | Cunningham | 435/287.2 |
| 2010/0227769 A1 | 9/2010 | Schulz | 436/164 |
| 2010/0231907 A1 | 9/2010 | Pien | 435/164 |

FOREIGN PATENT DOCUMENTS

| | | |
|---|---|---|
| CH | 0669050 | 2/1989 |
| CH | 0670521 | 6/1989 |
| EP | 0075353 | 3/1983 |
| EP | 0112721 | 7/1984 |
| EP | 0326219 | 8/1989 |
| EP | 0517777 | 4/1991 |
| EP | 0660924 | 7/1994 |
| EP | 1031828 | 8/2000 |
| EP | 1085315 | 3/2001 |
| FR | 2801977 | 6/2001 |
| GB | 2156970 | 10/1985 |
| GB | 2227089 | 7/1990 |
| JP | 05-228946 | 9/1993 |
| WO | WO 1981/00912 | 4/1981 |
| WO | WO 1984/02578 | 7/1984 |
| WO | WO 1986/07149 | 12/1986 |
| WO | WO 1990/08318 | 7/1990 |
| WO | WO 1991/13339 | 9/1991 |
| WO | WO 1992/04653 | 3/1992 |
| WO | WO 1992/21768 | 12/1992 |
| WO | WO 1993/14392 | 7/1993 |
| WO | WO 1996/38726 | 12/1996 |
| WO | WO 1997/19362 | 8/1997 |
| WO | WO 1998/10288 | 3/1998 |
| WO | WO 1998/57200 | 12/1998 |
| WO | WO 1999/09392 | 2/1999 |
| WO | WO 1999/09396 | 2/1999 |
| WO | WO 1999/54714 | 10/1999 |
| WO | WO 1999/66330 | 12/1999 |
| WO | WO 2000/23793 | 4/2000 |
| WO | WO 2000/29830 | 5/2000 |
| WO | WO 2001/02839 | 1/2001 |
| WO | WO 2001/04697 | 1/2001 |
| WO | WO 2001/92870 | 12/2001 |
| WO | WO 2002/61429 | 8/2002 |
| WO | WO 2010/05600 | 1/2010 |

OTHER PUBLICATIONS

"Research—Photonic Crystal Biosensors," Nano Sensors Group website, downloaded on Aug. 14, 2009.
Abel, et al., "Fiber-optic evanescent wave biosensor for the detection of oligonucleotides," *Analytical Chemistry*, 68:2905-2912, 1996.
Adamczyk et al., "Application of surface Plasmon resonance toward studies of low-molecular-weight antigen-antibody binding interactions," *Methods*, 20:319-328, 2000.
Amendment Under 37 CFR § 1.312 filed in U.S. Appl. No. 11/188,452, Sep. 21, 2009.
Anderson et al., "Proteomics: applications in basic and applied biology," *Curr Opinion Biotech* 11(4): 408-412. Aug. 1, 2000.
Avrutsky and Sychugov, "Reflection of a beam of finite size from a corrugated waveguide," *Journal of Modern Optics*, 36(11):1527-1539, 1989.
Avrutsky, et al., "Interference phenomena in waveguides with two corrugated boundaries," *Journal of Modern Optics*, 36:1303-1320, 1989.
Bolin, et al., "Refractive index of some mammalian tissues using a fiber optic cladding method," *Applied Optics*, 28:2297-2303, 1989.

Boye and Kostuk, "Investigation of the effect of finite grating size on the performance of guided-mode resonance filters," *Applied Optics*, 39(21):3649-3653, 2000.
Broad et al., "Growth and adipose differentiation of sheep preadipocyte fibroblasts in serum-free medium," *Eur. J Bichem.*, 135:33-39, 1983.
Brundrett, et al., "Effects of Modulation Strength in Guided-Mode Resonant Subwavelength Gratings at Normal Incidence," *J. Opt. Soc. Am. A.*, 17:1221-1230, 2000.
Brundrett, et al., "Normal-incidence guided-mode resonant grating filters: design and experimental demonstration," *Optics Letters*, 23(9):700-702, 1998.
Buckles and Petry, *Genetic Algorithms*, IEEE Computer Society Press, Los Alamitos, California, 1994.
Castillo et al., "Characterization of proliferation and differentiation of EGF-responsive striatal and septal precursor cells," *Int. J. Devl. Neuroscience*, 21:41-47, 2003.
Cekaite et al., "Analysis of the humoral immune response to immunoselected phage-displayed peptides by a microarray-based method," *Proteomics*, 4:2572-2582, 2004.
Chalazonitis et al., "The α1 subunit of laminin-1 promotes the development of neurons by interacting with LBP110 expressed by neural crest-derived cells immunoselected from the fetal mouse gut," *J. Neurobiol.*, 33:118-138, 1997.
Challener et al., "A multilayer grating-based evanescent wave sensing technique," *Sensors and Actuators B*, 71(1-2):42-46, 2000.
Chan et al., "A general method for discovering inhibitors of protein-DNA interactions u sing SRU BIND optical biosensor microplates," Poster, *SBS Conference*, 2008.
Chen, "Excitation of higher order modes in optical fibers with parabolic index profile," *Applied Optics*, 27(11):2353-2356, 1988.
Collings and Caruso, "Biosensors: recent advances," *Reports on Progress in Physics*, 60:1397-1445, 1997.
Cooper, "Current biosensor technologies in drug discovery," *Drug Discovery World*, pp. 68-82, Summer 2006.
Cooper, "Optical biosensors in drug discovery," *Nature Reviews* 1: 515-528. Jul. 2002.
Cromley, "Label-free detection new biosensors facilitate broader range of drug discovery applications," *Drug Discovery World*, pp. 63-74, Winter 2004-2005.
Cunningham et al., "Colorimetric resonant reflection as a direct biochemical assay technique," *Sensors and Actuators*, 4120:1-13, 2001.
Cunningham et al., "Colorimetric resonant reflection as a direct biochemical assay technique," The Fifteenth IEEE International Conference on Micro Electro Mechanical Systems, 2002.
Cunningham, *Introduction to Bioanalytical Sensors*, John Wiley and Sons, 1998.
Cush, et al., "The resonant mirror: a novel optical biosensor for direct sensing of biomolecular interactions Part I: Principle of operation and associated instrumentation," *Biosensors and Bioelectronics*, 8:347-353, 1993.
Davis, Ed.,: *Genetic Algorithms and Simulated Annealing*, Pitman, London ,1987.
Day, et al., "Filter Response Lineshapes of Resonant Waveguide Gratings," *J. Lightwave Tech.*, 14:1815-1824, 1996.
De Maria, et al., "Fiber-optic sensor based on surface plasmon interrogation," *Sensors and Actuators B*, 12:221-223, 1993.
Decision on Petition to Accept Unintentionally Delayed Benefit Claim to U.S. Appl. No. 09/707,435, issued in U.S. Appl. No. 11/656,612, dated Jun. 17, 2009.
Decision Sua Sponte Returning Untimely Filed Papers in Reexamination U.S. Appl. No. 90/009,276, mailed Jan. 4, 2010.
Declaration of Robert Magnusson Under 37 C.F.R. § 1.132 filed with Joint Claim Construction and Prehearing Statement on Mar. 14, 2011 in Civil Action No. 08-cv-01978 in the U.S. District Court, Northern District of Texas, Dallas Division.
Ding and Magnusson, "Double resonant single-layer bandpass optical filters," *Optics Letters* 29(10): 1135-1137. May 15, 2004.
Ding and Magnusson, "Resonant leaky-mode spectral-band engineering and device applications," *Optics Express* 12(23): 5661-5674, 2004.

(56) References Cited

OTHER PUBLICATIONS

Ding and Magnusson, "Use of nondegenerate resonant leaky modes to fashion diverse optical spectra," *Optics Express* 12(9): 1885-1890. May 3, 2004.
Exhibit A—Claim Chart—Plaintiffs' Infringement Contentions Under Patent Rule 3.1—U.S. Pat. No. 5,216,680, filed Aug. 20, 2010 in Civil Action No. 08-cv-01978 in the U.S. District Court, Northern District of Texas, Dallas Division.
Exhibit A—SRU's Disclosure of Preliminary Invalidity Contention to ROI, RSI ,and UTS Regarding U.S. Pat. No. 5,216,680, filed Oct. 21, 2010 in Civil Action No. 08-cv-01978 in the U.S. District Court, Northern District of Texas, Dallas Division.
Exhibit A filed with Joint Claim Construction and Prehearing Statement on Mar. 14, 2011 in Civil Action No. 08-cv-01978 in the U.S. District Court, Northern District of Texas, Dallas Division.
Exhibit A to Plaintiff's Second Amended Complaint and Jury Demand, filed Jun. 18, 2010 in Civil Action No. 3:08-CV-01978-M in the U.S. District Court, Northern District of Texas, Dallas Division.
Exhibit A to SRU Biosystems, Inc.'s Answer to Plaintiff's Second Amended Complaint and Jury Demand, Affirmative and Other Defenses, and Counterclaims, filed Jul. 9, 2010 in Civil Action No. 3:08-CV-01978-M in the U.S. District Court, Northern District of Texas, Dallas Division.
Exhibit A to SRU's Answer, Affirmative and Other Defenses, and Counterclaims, filed Aug. 31, 2009 in Civil Action No. 3:08-CV-01978-M in the U.S. District Court, Northern District of Texas, Dallas Division.
Exhibit B—SRU's Disclosure of Preliminary Invalidity Contention to ROI, RSI ,and UTS Regarding U.S. Pat. No. 7,400,399, filed Oct. 21, 2010 in Civil Action No. 08-cv-01978 in the U.S. District Court, Northern District of Texas, Dallas Division.
Exhibit B filed with Joint Claim Construction and Prehearing Statement on Mar. 14, 2011 in Civil Action No. 08-cv-01978 in the U.S. District Court, Northern District of Texas, Dallas Division.
Exhibit B to SRU Biosystems, Inc.'s Answer to Plaintiff's Second Amended Complaint and Jury Demand, Affirmative and Other Defenses, and Counterclaims, filed Jul. 9, 2010 in Civil Action No. 3:08-CV-01978-M in the U.S. District Court, Northern District of Texas, Dallas Division.
Exhibit B to SRU's Answer, Affirmative and Other Defenses, and Counterclaims, filed Aug. 31, 2009 in Civil Action No. 3:08-CV-01978-M in the U.S. District Court, Northern District of Texas, Dallas Division.
Exhibit B-1—Claim Chart—Plaintiffs' Infringement Contentions Under Patent Rule 3.1—U.S. Pat. No. 7,400,399 (Original Claims), filed Aug. 20, 2010 in Civil Action No. 08-cv-01978 in the U.S. District Court, Northern District of Texas, Dallas Division.
Exhibit B-2—Claim Chart—Plaintiffs' Infringement Contentions Under Patent Rule 3.1—U.S. Pat. No. 7,400,399—Claims 49-62 Added During Reexamination, filed Aug. 20, 2010 in Civil Action No. 08-cv-01978 in the U.S. District Court, Northern District of Texas, Dallas Division.
Exhibit C filed with Joint Claim Construction and Prehearing Statement on Mar. 14, 2011 in Civil Action No. 08-cv-01978 in the U.S. District Court, Northern District of Texas, Dallas Division.
Exhibit C to SRU Biosystems, Inc.'s Answer to Plaintiff's Second Amended Complaint and Jury Demand, Affirmative and Other Defenses, and Counterclaims, filed Jul. 9, 2010 in Civil Action No. 3:08-CV-01978-M in the U.S. District Court, Northern District of Texas, Dallas Division.
Exhibit C to SRU's Answer, Affirmative and Other Defenses, and Counterclaims, filed Aug. 31, 2009 in Civil Action No. 3:08-CV-01978-M in the U.S. District Court, Northern District of Texas, Dallas Division.
Exhibit C-1: Chart Comparing SRU '987 Claim Elements to Prior Art Wawro '399, Wawro SPIE, Magnusson '680, Rudigier '825, McGarry '674, Hobbs '624, , filed Dec. 24, 2009 in Civil Action No. 08-cv-01978 in the U.S. District Court, Northern District of Texas, Dallas Division.
Exhibit C-2: Chart Comparing SRU '987 Claim Elements to Prior Art Tibuleac Leos Presentation, Wawro SPIE Presentation, Wawro Research Notes, filed Dec. 24, 2009 in Civil Action No. 08-cv-01978 in the U.S. District Court, Northern District of Texas, Dallas Division.
Exhibit C-3: Chart Comparing SRU '562 Claim Elements to Prior Art Wawaro '399, Wawro SPIE, Magnusson '680, Avrutsky-Sychugov, Rudigier '825, Hobbs '624, filed Dec. 24, 2009 in Civil Action No. 08-cv-01978 in the U.S. District Court, Northern District of Texas, Dallas Division.
Exhibit C-4: Chart Comparing SRU '562 Claim Elements to Prior Art Tibuleac Leos Presenation, Wawro SPIE Presentation, Wawro Research Notes, filed Dec. 24, 2009 in Civil Action No. 08-cv-01978 in the U.S. District Court, Northern District of Texas, Dallas Division.
Exhibit C-5: Chart Comparing SRU '980 Claim Elements to Prior Art Wawro '399 Patent, Rudigier '825 Patent, Ackley '818, McGarry '674, filed Dec. 24, 2009 in Civil Action No. 08-cv-01978 in the U.S. District Court, Northern District of Texas, Dallas Division.
Exhibit D filed with Joint Claim Construction and Prehearing Statement on Mar. 14, 2011 in Civil Action No. 08-cv-01978 in the U.S. District Court, Northern District of Texas, Dallas Division.
Exhibit D to SRU Biosystems, Inc.'s Answer to Plaintiff's Second Amended Complaint and Jury Demand, Affirmative and Other Defenses, and Counterclaims, filed Jul. 9, 2010 in Civil Action No. 3:08-CV-01978-M in the U.S. District Court, Northern District of Texas, Dallas Division.
Exhibit E filed with Joint Claim Construction and Prehearing Statement on Mar. 14, 2011 in Civil Action No. 08-cv-01978 in the U.S. District Court, Northern District of Texas, Dallas Division.
Exhibit G, "Expert Technical Tutorial Declaration," filed with Joint Claim Construction and Prehearing Statement on Mar. 14, 2011 in Civil Action No. 08-cv-01978 in the U.S. District Court, Northern District of Texas, Dallas Division.
Ferguson and Walt, "Optical fibers make sense of chemicals," *Photonics Spectra*, 108-114, 1997.
Furlong, et al., "A fundamental approach for biosensor characterization," Proceedings of Sensors Expo, Helmers Publishing, 353-356, 1996.
Furlong, et al., "Fundamental system for biosensor characterization: application to surface plasmon resonance (SPR)," presented at Chemical, biochemical and environmental fiber sensors VIII, Denver, CO, 1996.
Furman and Tikhonravov, *Basics of Optics of Multilayer Systems*, Editions Frontieres, Paris, 1992.
Gale, et al., "Zero-order diffractive microstructures for security applications," Proceedings SPIE on Optical Security and Anti-counterfeiting systems, 1210:83-89, 1990.
Gaylord and Moharam, "Analysis and applications of optical diffraction by gratings," *Proc. IEEE*, 73(5):894-937, 1985.
Gestwicki et al., "Using receptor conformational change to detect low molecular weight analytes by surface plasmon resonance," *Anal. Chem.*, 4:5732-5737, 2001.
Goldberg, "Genetic algorithms in search, optimization and machine learning," Addison-Wesley, Reading, MA, 1989.
Golden, et al., "An evanescent wave biosensor- Part II: Fluorescent signal aquisition from tapered optic probes," IEEE Transactions on Biomedical Engineering, 41:585-591, 1994.
Golubenko, et al., "Total Reflection of Light from a Corrugated Surface of a Dielectric Waveguide," *Sov. J. Quantum Electron.*, 15:886-887, 1985.
Hao et al., "Fetal human hemotopoietic stem cells can differentiate sequentially into neural stem cells and then astrocytes in vitro," *Journal of Hematotherapy & Stem Cell Research*, 12:23-32, 2003.
Haupt, "An Introduction to Genetic Algorithms for Electromagnetics," *IEEE Antennas and Propagation Mag.*, 37:7-15, 1995.
Hessel and Oliner, "A new theory of Wood's anomalies on optical grating," *Applied Optics*, 4(10):1275-1297, 1965.
Homola and Slavik, "Fibre-optic sensor based on surface plasmon resonance," *Electronics Letters*, 32:480-482, 1996.
Homola et al., "Surface plasmon resonance sensors: review," *Sens. Actuators B.*, 54:3-15, 1999.

(56) References Cited

OTHER PUBLICATIONS

Horiuchi et al., "Innovative chemical compound microarrays for drug screening," *DrugsPlus International*, Jun./Jul. 2006.

Information Disclosure Statement submitted in Reexaminatioon U.S. Appl. No. 90/009,276, filed Jan. 13, 2009.

Interview Summary issued in Reexamination U.S. Appl. No. 90/009,276, dated Jul. 1, 2009.

Jin, et al., "Limitation of absorption-based fiber optic gas sensors by coherent reflections," *Applied Optics*, 36:6251-6255, 1997.

Johns, et al., "Computational and in vivo investigation of optical reflectance from human brain to assist neurosurgery," *Journal of Biomedical Optics*, 3:437-445, 1998.

Johnson and Abushagur, "Microgenetic-algorithm optimization methods applied to dielectric gratings," *J. Opt. Soc. Am.*, 12(5):1152-1160, 1995.

Joint Claim Construction and Prehearing Statement filed Mar. 14, 2011 in Civil Action No. 08-cv-01978 in the U.S. District Court, Northern District of Texas, Dallas Division.

Jorgenson and Yee, "A fiber-optic chemical sensor based on surface plasmon resonance," Sensors and Actuators B, 22:213-220, 1993.

Jung, "Surface Plasmon Resonance Fiber Optic Sensors," Proceedings of the 3rd Pacific NW Fiber Optic Sensor Workshop, Troutdale, OR; 2-8, 1997.

Kano et al., "Establishment of hepatic stem-like cell lines from normal adult porcine liver in a poly-D-Lysine-coated dish with Nair-1 medium," in Vitro *Cell Dev. Biol.—Animal*, 30:440-448, 2003.

Kazarinov, et al., "Second-Order Distributed Feedback Lasers with Mode Selection Provided by First-Order Radiation Loss," *IEEE J. Quant. Elect.*, QE-21:144-150, 1985.

Kersey, "A review of recent developments in fiber optic sensor technology," *Optical Fiber Technology*, 2:291-317, 1996.

Kikuta et al., "Refractive index sensor with a guided-mode resonant grating filter," *Optical Engineering for Sensing and Nanotechnology, Proc. SPIE*, 4416:219-222, 2001.

Kim, "Diffraction of Gaussian Laser Beams by Waveguide Gratings," *Master's thesis*. May 2000.

Kunz et al., "Replicated chirped waveguide gratings for optical sensing applications," *Sensors and Actuators* A 46-47:482-486, 1995.

Lemarchand, et al., "Increasing the Angular Tolerance of Resonant Grating Filters with Doubly Periodic Structures," *Opt. Lett.*, 23:1149-1151, 1998.

Levine, "Users guide to the PGAPack parallel genetic algorithm library," Argonne National Laboratory, ANL 95/18, Jan. 1996.

Li et al., "A new method for label-free imaging of biomolecular interactions," *Sensors and Actuators*, 99:6-13, 2004.

Li et al., "Optical scanning extrinsic Fabry-Perot interferometer for absolute microdisplacement measurement," *Applied Optics*, 36(34):8858-8861, 1997.

Liu, et al., "High-efficiency guided-mode resonance filter," *Optics Letters*, 23(19):1556-1558, 1998.

Luff, et al., "Integrated Optical Mach-Zender Biosensor," *Journal of Lightwave Technology*, 16:583-592, 1998.

Lukosz and Tiefenthaler, "Sensitivity of integrated optical grating and prism couplers as (bio)chemical sensors," *Sensors and Actuators*, 15(3):273-284, 1988.

Lukosz et al., "Output Grating Couplers on Planar Waveguides as Integrated Optical Chemical Sensors," *Sens. Actuators*, B1:585-588, 1990.

Madou, *Fundamentals of Microfabrication*, CRC Press: Boca Raton, Chapters 1-3, pp. 1-177, 1997.

Magnusson and Liu, "Fiber endface bioprobes with high sensitivity and spatial resolution," proposal submitted to Advanced Research Program and Advanced Technology Program (ARP/ATP) between Jun. and Aug. of 1999.

Magnusson and Shin, "Diffractive optical components," *Encyclopedia of Physical Science and Technology*, $3^{rd}$ edition, 4:421-440, 2002.

Magnusson and Wang, "Characteristics of waveguide-grating filters: Plane wave and Gaussian beam illumination," *Conference Proceedings of the IEEE Lasers and Electro-Optics Society Annual Meeting*, 157-158, San Jose, California, Nov. 15-18, 1993.

Magnusson and Wang, "New principle for optical filters," *Applied Physics Letters*, 61:1022-1024, 1992.

Magnusson and Wang, "Optical waveguide-grating filters," *Proceedings of the SPIE: International Conference on Holography, Correlation Optics, and Recording Materials*, 2108:380-391, Chernovtsy, Ukraine, May 10-14, 1993.

Magnusson and Wang, "Transmission bandpass guided-mode resonance filters," *Applied Optics*, 34(35):8106-8109, 1995.

Magnusson et al., "Characteristics of resonant leaky mode biosensors," *Proc. SPIE, Nanosensing: Materials and Devices II*, 6008:1-10, 2005.

Magnusson et al., "Guided-mode resonance biosensors employing phase detection," *Diffractive Optics and Micro-Optics (DOMO) Conference*, 2004.

Magnusson et al., "Guided-mode resonance effects in thin-film diffractive optics and their applications," 3729:212-221, 1999.

Magnusson et al., "Photonic devices enabled by waveguide-mode resonance effects in periodically modulated films," *Proc. SPIE, Nano- and Micro-Optics for Information Systems*, 5225(1):20-34, 2003.

Magnusson, "Comparison of grating-coupler sensor principles with guided-mode resonance sensor principles," Presentation, 2009.

Magnusson, et al., "Guided-mode resonance Brewster filter," *Optics Letters*, 23(8):612-614, 1998.

Mashev and Popov, "Zero order anomaly of dielectric coated gratings," *Opt. Commun.*, 55(6):377-380, 1985.

Mateus, "Ultracompact high-sensitivity label-free biosensor using VCSEL," *Proc. SPIE, Microarrays and Combinatorial Techniques: Design, Fabrication, and Analysis II*, 5328(1):140-146, 2004.

McGee et al., "Micro to Nano: liquid handling gets small," *Drug Discovery & Development*, 2005.

Melendez, et al., "Biological Sensor Systems," presented at Sensors Expo Proceedings, 349-352, 1996.

Melendez, et al., "Development of a surface plasmon resonance sensor for commerical applications," *Sensors and Actuators B*, 38-39:375-379, 1997.

Moharam, et al., "Formulation for stable and efficient implementation of the rigorous coupled-wave analysis of binary gratings," *Journal of the Optical Society of America, Part A*, 12:1068-1076, 1995.

Moharam, et al., "Stable implementation of the rigorous coupled-wave analysis for surface-relief gratings: enhanced transmittance matrix approach," *Journal of the Optical Society of America, Part A*, 12:1077-1086, 1995.

Nellen et al., "Integrated optical input grating couplers as biochemical sensors," *Sensors and Actuators*, 15:285-295, 1988.

Neviere et al., "About the theory of optical grating coupler-waveguide systems," *Optics Communications*, 8(2):113, 1973.

Norton, "Resonant grating structures: theory, design and applications," Doctoral Thesis—The University of Rochester, 1997.

Norton, et al., "Coupled-mode theory of resonant-grating filters," *Journal of the Optical Society of America, Part A*, 14(3):629-639, 1997.

Norton, et al., "Experimental investigation of resonant-grating filter lineshapes in comparison with theoretical models," *Journal of the Optical Society of America, Part A*, 15(2):464-472, 1998.

Notice of Allowance and Fee(s) Due issued in U.S. Appl. No. 09/707,435, dated Sep. 20, 2006.

Notice of Allowance and Fee(s) Due issued in U.S. Appl. No. 11/305,065, dated Jun. 26, 2007.

Notice of Allowance and Fee(s) Due issued in U.S. Appl. No. 11/305,065, dated Nov. 5, 2007.

Notice of Allowance and Fee(s) Due issued in U.S. Appl. No. 11/305,065, dated Nov. 30, 2007.

Notice of Allowance issued in U.S. Appl. No. 11/188,452, dated Jun. 25, 2009.

Notice of Allowance issued in U.S. Appl. No. 11/656,612, dated Jun. 26, 2009.

(56) References Cited

OTHER PUBLICATIONS

Notice of Allowance, issued in U.S. Appl. No. 11/656,612, dated Jan. 26, 2010.
Notice of Intent to Issue Ex Parte Reexamination Certificate in Reexamination U.S. Appl. No. 90/009,276, mailed Dec. 23, 2009.
Office Action issued in U.S. Appl. No. 09/707,435, dated Feb. 17, 2004.
Office Action issued in U.S. Appl. No. 09/707,435, dated Jan. 9, 2006.
Office Action issued in U.S. Appl. No. 09/707,435, dated Jun. 15, 2006.
Office Action issued in U.S. Appl. No. 09/707,435, dated Mar. 12, 2003.
Office Action issued in U.S. Appl. No. 09/707,435, dated May 31, 2005.
Office Action issued in U.S. Appl. No. 09/707,435, dated May 16, 2006.
Office Action issued in U.S. Appl. No. 09/707,435, dated Nov. 6, 2002.
Office Action issued in U.S. Appl. No. 09/707,435, dated Sep. 21, 2004.
Office Action issued in U.S. Appl. No. 11/188,452, dated Apr. 7, 2008.
Office Action issued in U.S. Appl. No. 11/188,452, dated Dec. 12, 2008.
Office Action issued in U.S. Appl. No. 11/188,452, dated Jun. 21, 2007.
Office Action issued in U.S. Appl. No. 11/188,452, dated Nov. 16, 2007.
Office Action issued in U.S. Appl. No. 11/305,065, dated Jan. 26, 2007.
Office Action issued in U.S. Appl. No. 11/656,612, dated Sep. 11, 2008.
Office Action issued in U.S. Appl. No. 12/115,484, dated Mar. 10, 2009.
Office Action issued in Reexamination U.S. Appl. No. 90/009,276, dated Apr. 21, 2009.
Order Granting Request for Ex Parte Reexamination issued in U.S. Appl. No. 90/009,276, mailed Nov. 13, 2008.
Ouellette, "Biosensors: Microelectronics marries biology," *The Industrial Physicist*, 11-12, 14, 1998.
Patent Owner Response to Office Action and Declaration of Robert Magnusson submitted in Reexamination U.S. Appl. No. 90/009,276, filed Jun. 22, 2009.
Peng and Morris, "Experimental demonstration of resonant anomalies in diffraction from two-dimensional gratings," *Optics Letters*, 21:549-551, 1996.
Peng, "Polarization-control components and narrow-band filters based on subwavelength grating," Doctoral Thesis—The University of Rochester, 1996.
Peng, et al., "Theory of Periodic Dielectric Waveguides," *IEEE Trans. Microwave Theory and Tech.*, MTT-23:123-133, 1975.
Petition to Accept Unintentionally Delayed Benefit Claim to U.S. Appl. No. 09/707,435 and Amendment and Response to Sep. 11, 2008 Office Action submitted in U.S. Appl. No. 11/656,612, filed Mar. 11, 2009.
Plaintiff's Responses to SRU's Second Set of Requests for Production of Documents filed Mar. 21, 2011 in Civil Action No. 08-cv-01978 in the U.S. District Court, Northern District of Texas, Dallas Division.
Plaintiff's Second Amended Complaint and Jury Demand, filed Jun. 18, 2010 in Civil Action No. 3:08-CV-01978-M in the U.S. District Court, Northern District of Texas, Dallas Division.
Plaintiffs RSI's and ROI's Invalidity Contentions Regarding Defendant SRU's U.S. Pat. No. 7,070,987; U.S. Pat. No. 7,371,562 and U.S. Pat. No. 7,175,980, filed Dec. 24, 2009 in Civil Action No. 08-cv-01978 in the U.S. District Court, Northern District of Texas, Dallas Division.
Plaintiffs' Answer to SRU's Second Counterclaims, filed Aug. 20, 2010 in Civil Action No. 3:08-CV-01978-M in the U.S. District Court, Northern District of Texas, Dallas Division.
Plaintiffs' Disclosure of Asserted Claims and Preliminary Infringement Contentions, filed Aug. 20, 2010 in Civil Action No. 08-cv-01978 in the U.S. District Court, Northern District of Texas, Dallas Division.
Plaintiffs' First Amended Complaint and Jury Demand filed by Resonant Sensors Incorporated and Resonant Optics Incorporated in Civil Action No. 3:08-CV-01978-M; in the U.S. District Court, Northern District of Texas, Dallas Division, filed Jan. 22, 2009.
Plaintiffs' First Amended Reply to Counterclaims, filed Oct. 16, 2009 in Civil Action No. 3:08-CV-01978-M in the U.S. District Court, Northern District of Texas, Dallas Division.
Plaintiffs' Original Complaint and Jury Demand filed by Resonant Sensors Incorporated and Resonant Optics Incorporated in Civil Action No. 3:08-CV-01978-M; in the U.S. District Court, Northern District of Texas, Dallas Division, filed Nov. 6, 2008.
Plaintiffs' Reply to Counterclaims, filed Sep. 21, 2009 in Civil Action No. 3:08-CV-01978-M in the U.S. District Court, Northern District of Texas, Dallas Division.
Popov et al., "Theoretical study of the anomalies of coated dielectric gratings," *Optica Acta*, 33(5):607-619, 1986.
Priambodo et al., "Fabrication and characterization of high-quality waveguide-mode resonant optical filters," *Applied Physics Letters*, 83(16):3248-3250, 2003.
RCE and Supplemental IDS, filed in U.S. Appl. No. 11/656,612, Sep. 25, 2009.
RCE and Supplemental IDS, filed in U.S. Appl. No. 11/656,612, Apr. 23, 2010.
Request for Ex Parte Reexamination of U.S. Pat. No. 7,400,399, filed Sep. 11, 2008.
Response to Apr. 7, 2008 Office Action submitted in U.S. Appl. No. 11/188,452, filed Sep. 8, 2008.
Response to Dec. 12, 2008 Office Action submitted in U.S. Appl. No. 11/188,452, filed Apr. 13, 2009.
Response to Jun. 21, 2007 Restriction Requirement submitted in U.S. Appl. No. 11/188,452, filed Jul. 23, 2007.
Response to Nov. 16, 2007 Restriction Requirement submitted in U.S. Appl. No. 11/188,452, filed Dec. 17, 2007.
Rosenblatt, et al., "Resonant grating waveguide structures," *IEEE Journal of Quantum Electronics*, 33:2038-2059, 1997.
Saarinen et al., "Guided-mode resonance filters of finite aperture," *Optical Engineering*, 34(9):2560-2566, 1995.
Sethi, "Transducer aspects of biosensors," *Biosensors and Bioelectronics*, 9:243-264, 1994.
Sharma and Rogers, "Biosensors," *Meas. Sci. Technol.*, 5:461-472, 1994.
Shin et al., "Theory and experiments of resonant waveguide gratings under Brewster incidence," *Proc. SPIE, Gradient Index, Miniature, and Diffractive Optical Systems*, 3778(199):31-39, 1999.
Shin et al., "Thin-film optical filters with diffractive elements and waveguides," *Optical Engineering*, 37:2634-2646, 1998.
Slavik, et al., "Miniaturization of fiber optic surface plasmon resonance sensor," *Sensors and Actuators B*, 51:311-315, 1998.
Slavik, et al., "Novel surface plasmon resonance sensor based on single-mode optical fiber," Chemical, Biochemical and Environmental Sensors IX, Munich, Germany, Jun. 16-18, Proceedings of SPIE, 3105:325-331, 1997.
Slavik, et al., "Optical fiber surface plasmon resonance sensor for an aqueous environment," Proceedings of the International Conference on Optical Fiber Sensors, Williamsburg, VA, 436-439, 1997.
SRU Biosystems, Inc.'s Answer to Plaintiff's Second Amended Complaint and Jury Demand, Affirmative and Other Defenses, and Counterclaims, filed Jul. 9, 2010 in Civil Action No. 3:08-CV-01978-M in the U.S. District Court, Northern District of Texas, Dallas Division.
SRU's Answer, Affirmative and Other Defenses, and Counterclaims, filed Aug. 31, 2009 in Civil Action No. 3:08-CV-01978-M in the U.S. District Court, Northern District of Texas, Dallas Division.

(56) References Cited

OTHER PUBLICATIONS

SRU's Notice of Service of Preliminary Invalidity Contentions, filed Oct. 21, 2010 in Civil Action No. 08-cv-01978 in the U.S. District Court, Northern District of Texas, Dallas Division.
SRU's Preliminary Invalidity Contentions, filed Oct. 21, 2010 in Civil Action No. 08-cv-01978 in the U.S. District Court, Northern District of Texas, Dallas Division.
Statement of Substance of Interview submitted in Reexamination U.S. Appl. No. 90/009,276, filed Jul. 17, 2009.
Stone and Stulz, "FiEnd filters: passive multilayer thin-film optical filters depsosited on fibre ends," Electronic Letters, 26(16):1290-1291, 1990.
Sun et al., "Use of bioluminescent salmonella for assessing the efficiency of constructed phage-based biosorbent," Journal of Industrial Microbiology & Biotechnology, 27:126-128, 2001.
Supplemental IDS, filed in Reexamination U.S. Appl. No. 90/009,276, Dec. 29, 2009.
Supplemental Information Disclosure Statement submitted in Reexamination U.S. Appl. No. 90/009,276, filed Jul. 27, 2009.
Supplemental Information Disclosure Statement submitted in Reexamination U.S. Appl. No. 90/009,276, filed Jul. 14, 2009.
Supplementary Partial European Search Report issued in European Application No. 07814755.0, dated Jan. 13, 2011.
Sychugov, et al., "Waveguide coupling gratings for high-sensitivity biochemical sensors," Sensors and Actuators B, 38-39:360-364, 1997.
Tamir and Zhang, "Resonant scattering by multilayered dielectric gratings," Journal of the Optical Society of America A, 14:1607-1617, 1997.
Tamir et al., "Analysis and Design of Grating Couplers," Appl. Phys. 14:235-254, 1977.
TFCalc manual, Thin Film Design Software for Windows, Version 3.0, Software Spectra, Inc., 1995.
Tibuleac and Magnusson, "Diffractive narrow-band transmission filters based on guided-mode resonance effects in thin-film multilayers," IEEE Photonics Technology Letters, 9(4):464-466, 1997.
Tibuleac and Magnusson, "Reflection and transmission guided-mode resonance filters," Journal of the Optical Society of America, Part A, 14:1617-1626, 1997.
Tibuleac et al., "Design of reflection and transmission guided-mode resonance filters with genetic algorithms," Optical Society of America Annual Meeting, Baltimore, Md., Oct. 1998, Conference Proceedings, p. 128, 1998.
Tibuleac et al., "Experimental verification of waveguide-mode resonant transmission filters," IEEE Microwave and Guided Wave Letters, 9(1):19-21, 1999.
Tibuleac et al., "Guided-mode resonance filters generated with genetic algorithms," Proceedings of the Topical Meeting on Diffractive Optics and Micro-Optics, 10:24-26, 1998.
Tibuleac et al., "Narrow-linewidth bandpass filters with diffractive thin-film layers," Optical Letters, 26(9):584-586, 2001.
Tibuleac, "Characteristics of reflection and transmission waveguide-grating filters," Masters Thesis, University of Texas at Arlington, 1996.
Tibuleac, "Guided-mode resonance reflection and transmission filters in the optical and microwave spectral ranges," Dissertation, University of Texas at Arlington, Dec. 15, 1999.
Tibuleac, et al., "Dielectric frequency selective structures incorporating waveguide gratings," IEEE Transactions on Microwave Theory and Techniques, 48(4):553-561, 2000.
Tibuleac, et al., "Direct and inverse techniques of guided-mode resonance filter designs," IEEE Antennas and Propagation Society International Symposium, Conference Proceedings 4:2380-2383, 1997.
Tibuleac, et al., "Resonant diffractive structures integrating waveguide gratings on optical fiber endfaces," Proceedings of IEEE Lasers and Electro Optics Society. Annual Meeting, San Francisco, CA, Nov. 1999, Conference Proceedings 2: 874-875, 1999.
Tiefenthaler and Lukosz, "Integrated optical switches and gas sensors," Optics Letters, 10(4):137-139, 1984.
Tiefenthaler et al., "Sensitivity of grating couplers as integrated-optical chemical sensors," J. Opt. Soc. Am., B6:209-220, 1989.
Ting-Chang et al., "Novel GMR-based biochip," Proc. SPIE, Optical Diagnostics and Sensing V, 5702(1):160-167, 2005.
Tugendhaft, et al., "Reflection intensity optical fiber sensors for the mid-infrared," Applied Optics, 36:1297-1302, 1997.
U.S. Ex Parte Reexamination Certificate (7424th) for U.S. Pat. No. 7,400,399 Cl, issued Mar. 23, 2010.
U.S. Appl. No. 60/244,312, entitled "Resonant reflection microarray," by Cunningham and Hobbs, filed Oct. 30, 2000, and may have first published on Nov. 13, 2003, the publication date of US 2003/0210396, the published version of the patent application that issued as U.S. Pat. No. 6,870,624 and that claims priority to U.S. Appl. No. 60/244,312.
Vincent, et al., "Corrugated Dielectric Waveguides: A Numerical Study of the Second-Order Stop Bands," Appl. Phys., 20:345-351, 1979.
Wan et al., "Landscape phage-based magnetostrictive biosensor for detecting Bacillus anthracis spores," Proc. IEEE Sens., 1308-1311, 2005.
Wang and Magnusson, "Design of waveguide-grating filters with symmetrical line shapes and low sidebands," Optics Letters, 19:919-921, 1994.
Wang and Magnusson, "Multi-layer Waveguide Grating Filters," Applied Optics, 34(14):2414-2420, 1995.
Wang and Magnusson, "Resonance of asymmetric dielectric waveguides containing a diffraction grating," Abstract and Poster, The Antennas and Propagation Society International Symposium, IEEE, 1990.
Wang and Magnusson, "Theory and applications of guided-mode resonance filters," Applied Optics, 32: 2606-2613, 1993.
Wang et al., "Guided-mode resonance in planar dielectric-layer diffraction grating," J. Opt. Soc. Am. A., 7(8):1470, 1990.
Wang, et al., "Self-referenced fiber optic sensor for microdisplacement measurement," Optical Engineering, 34(1):240-243, 1995.
Wawro and Tibuleac, "Novel diffractive structures integrating waveguide-gratings on optical fiber endfaces," Abstract Book associated with The University of Texas at Arlington's Graduate Student Research Symposium, Mar. 24, 1999.
Wawro et al., "Optical fiber endface biosensor based on resonances in dielectric waveguide gratings," Biomedical Diagnostic, Guidance and Surgical Assist Systems II, Proceedings SPIE, 3911:86-94, May 2000.
Wawro et al., "Optical Waveguide-mode Resonant Biosensors," Optical imaging sensors and systems for homeland security applications 367-384, Javidi ed., Springer. 2003.
Wawro et al., "Resonating periodic waveguides as ultra resolution sensors in biomedicine," Proceedings of SPIE Nanoengineering: Fabrication, Properties, Optics, and Devices 5515: 52-57. 2004.
Wawro, "Design, Fabrication and Testing of Waveguide Gratings for Spectral Filters, Photonic Antennas and Optical Fiber Sensors," Thesis for the Master of Science in Electrical Engineering, The University of Texas at Arlington, Dec. 1999.
Yariv, "Coupled-Mode Theory for Guided-Wave Optics," IEEE Journal of Quantum Electronics 9(9): 919-933. Sep. 1973.
Yih et al., "Optical waveguide biosensors constructed with subwavelength grating," Applied Optics, Optical Society of America, 45(9):1938-1942, 2006.
Zhang et al., "Use of surface Plasmon resonance for the measurement of low affinity binding interactions between HSP72 and measles virus nucleocapsid protein," Biol. Proceed., 5(1):170-181, 2003.
Zhang, et al., "Spatial Modifications of Gaussian Beams Diffracted by Reflection Gratings," J. Opt. Soc. Am. A, 6:1368-1381, 1989.
Zuffada et al., "Designing Dielectric Grating Filters with PGAPACK," In: Electromagnetic Optimization by Genetic Algorithms, John Wiley & Sons, Inc. (Rahmat-Samii and Michielssen, eds.), New York, New York, pp. 367-397, 1999.
Zuffada et al., "Synthesis of novel all-dielectric grating filters using genetic algorithms," IEEE Transaction on Antennas and Propagation, 46:657-663, 1998.

* cited by examiner

Chromosome genes (alleles)

RESONANT WAVEGUIDE-GRANTING DEVICES AND METHODS FOR USING SAME

CROSS-REFERENCES TO RELATED APPLICATIONS

This is a continuation of co-pending application Ser. No. 12/115,484, now U.S. Pat. No. 8,514,391, filed May 8, 2008, which is a continuation of co-pending application Ser. No. 11/305,065, now U.S. Pat. No. 7,400,399, filed Dec. 16, 2005, which is a divisional of application Ser. No. 09/707,435, filed Nov. 6, 2000 and now U.S. Pat. No. 7,167,615, which claims priority to U.S. Provisional Patent Application Ser. No. 60/163,705 filed Nov. 5, 1999 and U.S. Provisional Patent Application Ser. No. 60/164,089 filed Nov. 6, 1999. The entire texts of all of these patent applications are specifically incorporated by reference without disclaimer.

BACKGROUND OF THE INVENTION

1. Field of the Invention

The present invention relates generally to the field of optical filters and sensors. More particularly, it concerns the use of the guided-mode resonance effect occurring through the use of waveguide gratings attached to the endfaces of waveguides such as optical fibers in fields such as optical sensing and communications.

2. Description of Related Art

Resonance anomalies occurring in waveguide gratings (WGGs) have been the subject of current interest for spectral filtering applications [Magnusson and Wang, 1992; Wang and Magnusson, 1993; Wang and Magnusson, 1994; Shin et al., 1998; Tibuleac and Magnusson, 1997; Tibuleac, et al., 2000; Wawro, et al., 2000; Avrutsky, et al., 1989; Boye and Kostuk, 1999; and Rosenblatt, et al., 1997]. Guided-mode resonances (GMRs) occurring in subwavelength WGGs admitting only zero-order propagating diffraction orders yield spectral filters with unique properties such as peak reflectances approaching 100%, narrow linewidths, and low sidebands. Filter characteristics, such as center wavelength, linewidth and sideband behavior, are defined by the waveguide-grating parameters, such as grating period, grating profile, refractive indices, layer thicknesses, and grating fill factor.

Changes in any parameters of the diffractive structure can result in a responsive shift of the reflected or transmitted wavelength band. In general, for spectral filtering applications, the most stable GMR structure is sought to prevent an unwanted resonance shift due to small parameter fluctuations. However, for spectroscopic sensing applications, it is desirable to enhance the resonance instability to create a device that will respond to very small parameter changes. This type of device can be utilized, for example, to detect very small changes in the refractive index or thickness of a media being evaluated in biomedical, industrial or environmental sensing applications. Implementation of the guided-mode resonance effect for optical sensing using planar waveguide grating structures and free-space propagating incident waves has been proposed in previous publications [Wang and Magnusson, 1993; Shin et al., 1998].

Experimental fabrication of waveguide gratings utilizing the GMR effect has primarily been restricted to planar WGGs with an incident beam that is propagating in free space. Experimental results for 1-D grating GMR filters incorporate single layer and multilayer reflection filter designs, including a TM polarization reflection filter utilizing the Brewster effect [Magnusson, et al., 1998]. Double layer GMR filter efficiencies as high as 98.5% have been reported by Liu, et al. for TE incident polarization [Liu, et al., 1998]. GMR crossed grating structures (2-D grating filters) have been experimentally fabricated by Peng and Morris [Peng and Morris, 1996], with a reported filter efficiency of 60%. Norton et al. [Norton, et al., 1998] investigated the dependence of lineshape and tunability in central wavelength and resonant angle position on grating parameters.

Chen [Chen, 1988] reports a theoretical design incorporating a diffraction grating on an optical fiber endface that is used to excite higher order modes in multimode optical fibers. Wang et al. [Wang, et al., 1995] reports a fiber optic proximity sensor design incorporating a diffraction grating on a fiber endface. However, the diffraction gratings reported in these two references do not have waveguide properties, and, consequently, do not exhibit the GMR effect.

A biosensor is an analytical device that integrates an immobilized biologically sensitive material (analyte), such as enzyme, antibody, DNA, cells, or organic molecules, with an electrochemical, piezoelectric, optical or acoustic transducer to convert a biochemical response into a signal for measurement, interpretation, or control. Electrochemical and optical sensors are most widely used. Optical biosensors can provide fast, accurate, and safe analyte detection. Current fiber-optic sensor technology applies fluorescence, total internal reflection, intensity reflection, and surface-plasmon resonances.

The surface plasmon resonance (SPR) effect, is a widely used optical detection method that is highly sensitive to changes in the optical properties (refractive index, monolayer thickness) at the sensor surface. The term surface plasmon (SP) refers to an electromagnetic field charge-density oscillation that can occur at the surface of a conductor. An SP mode can be resonantly excited by parallel-polarized (TM) incident light. Conventional surface plasmon sensors include a prism or diffraction grating for phase matching of the incident and SP waves; commercial systems employ bulk optical components. Fiber-optic SPR sensors have been reported; in these a metal sleeve is deposited on the side of the fiber to which the analyte is contacted. A drawback of the SPR technology is the inherently large linewidth; typically $\Delta\lambda \sim 50$ nm. Therefore, a sensor utilizing the GMR effect that would provide smaller linewidths would exhibit a significant resolution dynamic-range advantage over SPR sensors.

SUMMARY OF THE INVENTION

In one respect, the invention is a waveguide grating device. The device includes at least one waveguide that has an end, and the end has an endface. As used herein, "waveguide" means any device possessing a structure capable of confining optical energy. As used herein, "endface" means a face on the end of a waveguide that may be oriented at any angle with respect to a wave being propagated through the waveguide. The device also includes a waveguide grating fabricated on the endface of the at least one waveguide. The waveguide grating has at least one waveguide layer and at least one grating layer. As used herein, "grating layer" includes any suitable layer possessing a grating. The gratings on the present grating layers include surface-relief type gratings (e.g., those in which the amplitude of the grating may be modulated) and volume gratings (e.g., those in which the refractive index of the grating may be modulated). The periodicity of the gratings of the present grating layers may be varied and/or their modulation depth (amplitude or index) may be varied. The grating may be nonuniform. As used herein, "waveguide layer" includes any suitable layer possessing a structure capable of confining optical energy. Throughout the present disclosure, including the claims, waveguide layers are distinct from the waveguides on which they are fabricated. The at least one waveguide layer and the at least one grating layer may be the same layer.

In other respects, the at least one waveguide may be a fiber. The at least one waveguide may possess any suitable shape, including elliptical. The shape may be rectangular. The at least one waveguide may be a channel waveguide. The at least one waveguide may be cylindrical in shape. The at least one waveguide may be a slab waveguide. The at least one waveguide may be a ridge waveguide. The at least one grating layer may include a dielectric material. The at least one grating layer may include a glass. The at least one grating layer may include a polymer. The at least one grating layer may include a solid or liquid crystalline material. The at least one grating layer may include a semiconductor material. The at least one grating layer may include a photorefractive material. The at least one waveguide layer may include a dielectric material. The at least one waveguide layer may include a glass. The at least one waveguide layer may include a polymer. The at least one waveguide layer may include a solid or liquid crystalline material. The at least one waveguide layer may include a semiconductor material. The at least one waveguide layer may include a photorefractive material. The at least one grating layer and the at least one waveguide layer may be the same layer. The at least one grating layer and the at least one waveguide layer may be different layers in contact with each other. The waveguide grating may also include at least a third layer in contact with the at least one waveguide layer, the at least one grating layer, or both the at least one waveguide layer and the at least one grating layer. The at least third layer may be a buffer layer, which may be formed from any material suitable for forming either the at least one waveguide layer or the at least one grating layer, and which may be formed using the same techniques that may be used to form either the at least one waveguide layer or the at least one grating layer.

As a buffer layer, the at least third layer may be made of a dielectric and may serve to shape the spectral reflection of the waveguide grating, such as to lower the sidebands, shift the resonance to a desired wavelength, or narrow or widen the linewidth of the GMR. The buffer layer may serve as neither a waveguide layer nor a grating layer. The at least third layer may also be formed of metal, which in some embodiments, may serve a buffer layer intermediate two layers of the waveguide grating that do not otherwise attach well to one another. In other embodiments, the at least third layer (made from either a dielectric or a metal, for example), may be the layer of the waveguide grating in contact with a substance to be sensed/evaluated. In some cases, the substance to be sensed may not attach itself efficiently to dielectric materials composing, at least in part, the waveguide grating. The use of a third layer that is thin may facilitate the attachment of substances being sensed. In still other embodiments, such as biomedical applications, an organic substance being sensed may attach itself only to other organic substances, and not to dielectric or metallic layers of the waveguide grating. In such situations, the use of a third layer (metallic, for example) may be used to which another (fourth) organic layer could be attached. The organic substance being sensed could then attach itself to such a fourth organic layer. The at least third layer may be distinct from both the at least one waveguide and grating layers. The waveguide grating may also include at least a third layer in contact with the at least one grating layer, and may include an arbitrarily large number of layers, each of which may be either additional waveguide layers, additional grating layers, or additional buffer layers.

In another respect, the invention is a system for spectral filtering and the system utilizes a guided-mode resonance effect in a waveguide. The guided-mode resonance effect is described below in greater detail. The system includes a waveguide grating device. The waveguide grating device includes at least one waveguide that has a proximal end and a distal end. The distal end of the at least one waveguide has an endface. The device also has a waveguide grating fabricated on the endface of the at least one waveguide. The waveguide grating has at least one waveguide layer and at least one grating layer. The waveguide grating also has a plurality of variable parameters. The plurality of variable parameters includes at least one permittivity of the at least one grating layer, the permittivity of the at least one waveguide layer, the periodic structure of the at least one grating layer, the grating fill factor of the at least one grating layer, the thickness of the at least one waveguide layer, and the thickness of the at least one grating layer. The at least one waveguide layer and the at least one grating layer may be the same layer. Also, the permittivity of the at least one waveguide layer and one of the permittivities of the at least one permittivity of the at least one grating layer may be the same.

In other respects, the system may also include a source coupled to the proximal end of the at least one waveguide for propagating a signal through the at least one waveguide. After the signal is propagated, it contacts the waveguide grating and is reflected from the waveguide grating in whole or in part, or transmitted through the waveguide grating in whole in or in part, depending at least partially upon the plurality of variable parameters. The source may be a broadband source. The source may be a white light. The source may be a light emitting diode. The source may be a laser. The source may be a continuous wave source. The source may be a pulsed source. The source may be polarized. The source may be unpolarized. The source may be an incoherent light source. The source may be a coherent light source. The source may have wavelengths ranging from the ultraviolet to microwave range (on the order of 100 nm to the order of tens of centimeters).

In still other respects, the system may also include a photodetector operationally coupled to the at least one waveguide. As used herein, if a first device is "operationally coupled" to a second device, one or more mediums or devices may separate the first and second devices such that the first and second devices are not in physical contact with each other. The photodetector may include silicon. The photodetector may include germanium. The photodetector may include indium gallium arsenide. Silicon, germanium, and indium gallium arsenide are examples of semiconductor detectors that may serve as photodetectors operationally coupled to waveguides of the present devices. Semiconductor detectors are power detectors commonly used in the detection of continuous wave sources ranging from about 160 nm to about 1800 nm wavelengths (e.g., visible range to infrared). The photodetector may include a pyroelectric material. The photodetector may include the human eye.

In other respects, the at least one waveguide may be a fiber. The at least one waveguide may be rectangular in shape. The at least one waveguide may be a channel waveguide. The at least one waveguide may be cylindrical in shape. The at least one waveguide may be a slab waveguide. The at least one waveguide may be a ridge waveguide. The at least one grating layer may include a dielectric material. The at least one grating layer may include a glass. The at least one grating layer may include a polymer. The at least one grating layer may include a liquid or solid crystalline material. The at least one grating layer may include a semiconductor material. The at least one grating layer may include a photorefractive material. The at least one waveguide layer may include a dielectric material. The at least one waveguide layer may include a glass. The at least one waveguide layer may include a polymer. The at least one waveguide layer may include a liquid or solid crystalline material. The at least one waveguide layer may include a semiconductor material. The at least one waveguide layer may include a photorefractive material. The at least one grating layer and the at least one waveguide layer may be the same layer. The at least one grating layer and the at least one waveguide layer may be different layers in contact with each other. The waveguide grating may also include a third layer in contact with the at least one waveguide layer. The third layer may be a buffer layer, which may be formed from any material suitable for forming either the at least one waveguide layer or the at least one grating layer, and which may be formed using the same techniques that may be used to form either the at least one waveguide layer or the at least one grating layer. The third layer may be distinct from both the at least one waveguide and grating layers. The plurality of variable parameters may include the thickness of the third layer. The waveguide grating may also include a third layer in contact with the at least one grating layer, and may include an arbitrarily large number of layers, each of which may be either additional waveguide layers, additional grating layers, or additional buffer layers.

In still other respects, the system may include a sensor operationally coupled to the waveguide grating device. The sensor may be an electrochemical sensor. The sensor may be an optical sensor. The sensor may be a surface plasmon sensor. The sensor may be a fluorescence sensor. The sensor may be an evanescent wave sensor.

In another respect, the invention is a waveguide grating device that includes at least one waveguide through which a signal having at least one wavelength may be propagated. The at least one waveguide has an end, and the end has an endface. The device also includes a waveguide grating fabricated on the endface of the at least one waveguide. The waveguide grating has at least one waveguide layer and at least one grating layer. The waveguide grating also has a plurality of variable parameters. The plurality of variable parameters includes at least one permittivity of the at least one grating layer, the permittivity of the at least one waveguide layer, the periodic structure of the at least one grating layer, the grating fill factor of the at least one grating layer, the thickness of the at least one waveguide layer, and the thickness of the at least one grating layer. The periodic structure of the at least one grating layer has a period less than the at least one wavelength of the signal. The at least one waveguide layer and the at least one grating layer may be the same layer. Also, the permittivity of the at least one waveguide layer and one of the permittivities of the at least one permittivity of the at least one grating layer may be the same.

In another respect, the invention is a waveguide grating device that includes at least a first waveguide having a first end. The first end has a first endface. The waveguide grating device also includes a first waveguide grating fabricated on the first endface. The first waveguide grating has at least a first waveguide layer and at least a first grating layer. The at least first waveguide layer and the at least first grating layer may be the same layer. The waveguide grating device also includes at least a second waveguide having a second end. The second end has a second endface. The waveguide grating device also includes a second waveguide grating fabricated on the second endface. The second waveguide grating has at least a second waveguide layer and at least a second grating layer. The at least second waveguide layer and the at least second grating layer may be the same layer.

In other respects, the at least first and second waveguides may be fibers.

In another respect, the invention is a method of forming a waveguide grating device that includes providing at least one waveguide that has an end, and the end has an endface; and fabricating a waveguide grating on the endface of the at least one waveguide to form the waveguide grating device.

In other respects, the method may also include cleaving the end to form the endface of the at least one waveguide. The method may also include polishing the end to form the endface of the at least one waveguide.

In still other respects, the waveguide grating may include at least one layer of polymer. The fabricating may include dipping the endface of the at least one waveguide into the polymer. The method may also include heating the at least one layer of polymer. The method may also include patterning the at least one layer of polymer. The patterning may include holographic interferometry, photolithography, electron-beam lithography, laser-beam lithography, or contact printing the at least one layer of polymer to form a grating. The fabricating may include spin coating the endface of the at least one waveguide with a polymer.

In still other respects, the waveguide grating may include at least one layer of photosensitive glass or at least one layer of dielectric. The method may also include etching the at least one layer of dielectric to form a grating.

In other respects, the waveguide grating may include at least a first layer and at least a second layer adjacent the at least first layer. The fabricating may include depositing the at least first layer on the endface of the at least one waveguide by sputtering and coating the at least first layer with the at least second layer. The fabricating may also include depositing the at least first layer on the endface of the at least one waveguide by thermal evaporation. The fabricating may include depositing the at least first layer on the endface of the at least one waveguide by electron-beam evaporation. The fabricating may also include depositing the at least first layer on the endface of the at least one waveguide by molecular beam epitaxy. The fabricating may also include depositing the at least first layer on the endface of the at least one waveguide by metal-organic chemical vapor deposition. The fabricating may include depositing the at least first layer on the endface of the at least one waveguide by chemical vapor deposition. The fabricating may include depositing the at least first layer on the endface of the at least one waveguide by liquid phase epitaxy.

In another respect, the invention is a method of detecting at least one parameter of a medium. As used herein, "medium" means material under investigation in solid, liquid, plasma, or gas form. The method includes providing a waveguide grating device. The device includes at least one waveguide that has an end, and the end has an endface. The device also includes a waveguide grating fabricated on the endface of the at least one waveguide. The waveguide grating has at least one waveguide layer and at least one grating layer. The at least one waveguide layer and the at least one grating layer may be the same layer. The method also includes contacting the waveguide grating with a medium, propagating a signal having at least one signal attribute through the at least one waveguide such that the signal contacts the waveguide grating and the at least one signal attribute is modified, and comparing the modified signal attribute to a known signal attribute to detect the at least one parameter of the medium. As used herein, "signal attribute" means power of a reflected or transmitted wave at a specific wavelength, a specific spectral range, or a specific polarization.

In other respects, the at least one signal attribute may be the spectral content of the signal. The at least one signal attribute may be the intensity of the signal. The at least one signal attribute may be the polarization of the signal. The at least one parameter of the medium may be the presence or absence of a substance. The at least one parameter of the medium may also be the quantity of a substance. The at least one parameter of the medium may be the refractive index of the medium. The at least one parameter of the medium may be the thickness of the medium. The medium may include a first parameter and a second parameter, and the comparing may include comparing the modified signal attribute to a known signal attribute to detect both the first and second parameters.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
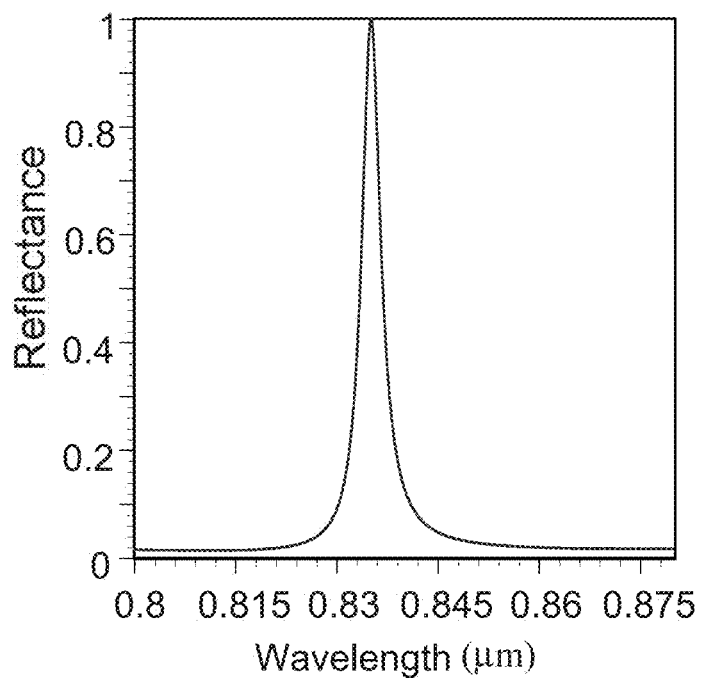
FIGS. 1 and 2. An embodiment of one of the present devices useful as a reflection filter designed for an ionic self assembled polymer waveguide layer having a thickness $d_2$ and a photoresist grating layer having a thickness $d_1$ recorded on the top surface. TE polarization at normal incidence, $n_C$=1.0, $n_{1H}$=1.632, $n_{1L}$=1.0, $n_2$=1.8, $n_S$=1.45, $d_1$=200 nm, $d_2$=280 nm, $\Lambda$=515 nm, fill factor f=0.5. As depicted, $f\Lambda$ is the width of the high-index region of the grating layer.

Disclosed herein is a new GMR device that includes a waveguide having an end that has an endface and a waveguide grating fabricated on the endface. As defined above, waveguides include fibers such as optical, single-mode, multi-mode, polarization-maintaining, graded-index, step-index, nonlinear core (either with or without embedded electrodes), polymer, phototonic crystal waveguides and fibers, glass, crystal-core, and chalcogenide fibers; waveguides with shapes such as rectangular, elliptical and cylindrical; slab waveguides and ridge waveguides. The waveguide grating is made up of at least one waveguide layer and at least one grating layer, and the grating and waveguide layers may be the same layer. The layers, if separate, may be arranged in any suitable fashion with respect to each other and the waveguide. A source may propagate an incident signal, such as a broad-spectrum signal, through the waveguide, the waveguide may guide the signal to the waveguide grating, and the waveguide grating, depending on its design, may filter the signal to reflect or transmit a desired spectral band of the signal. Used as a filter, characteristics such as center wavelength (the wavelength at which a peak or a notch is exhibited in the spectrum of the reflected or transmitted wave), linewidth (the width of the spectral peak or notch) and sideband (reflectance or transmittance in the spectral region outside the peak or notch spectral region) are defined by certain waveguide-grating parameters, such as the periodic structure of the grating layer(s), the refractive indices of the layer(s) forming the waveguide grating, the thicknesses of those layers, and the fill factor of the grating layer(s). The present waveguide grating devices provide a new class of diffractive optical elements as a result of the GMR spectral filters resulting therefrom. Potential applications for the present devices include use as spectral filters for use in fiber optic systems (such as communications), as sensors for high resolution chemical or biochemical sensing, and as integrated polarized reflectors for fiber lasers.

The phrase guided-mode resonance (GMR) refers to a rapid variation in the diffraction efficiency spectrum of waveguide gratings generally, and those described herein. A resonance occurs when an incident wave from a propagated signal that may include more than one wave is phase matched to a leaky guided mode allowed by a waveguide grating. Phase matching may be accomplished through a diffraction grating, which is inherently polarization sensitive. Resonances occurring in subwavelength waveguide gratings (i.e., waveguide gratings having a grating layer(s) with a period, $\Lambda$, less than the wavelength, $\lambda$, of the input wave admitting only zero-order propagating diffraction orders, where $\Lambda < \lambda/n_s$, $\lambda/n_c$ where $\lambda/n_s$ and $\lambda/n_c$ are the wavelengths in the substrate and cover regions respectively, [i.e. regions of propagation of the incident and emerging waves]; $\lambda$ is the wavelength in vacuum, and $n_s$ and $n_c$ are the refractive indices of the substrate and cover regions, respectively) allow complete energy exchange between the forward and backward propagating zero-order waves. In this case, all higher order diffracted waves are evanescent. In fact, when these evanescent waves correspond to waveguide modes supportable by the WGG, the resonance occurs.

Considering a single layer WGG, for a resonance to occur, the average refractive index of the grating layer, $n_{av}$, is required to be higher than the refractive index of the surrounding cover and it is required to be higher than the refractive index of the substrate. For a multi-layer structure, one of the layers in the stack needs to meet this requirement. The average refractive index of the grating layer may be calculated using the following equation:

$$n_{av} = [n_L^2 + f(n_H^2 - n_L^2)]^{1/2}$$

where $n_H$ and $n_L$ are the refractive indices of the high and low-refractive index regions of the grating layer, and f is the fill factor of the grating layer (i.e. the fraction of the grating period occupied by the high-refractive index material). The efficient energy exchange occurs within small ranges of at least one physical parameter of the device, such as the angle of incidence of the input wave or signal, wavelength, thickness of the layers utilized, period of the grating layer(s), and the refractive indices of the grating and waveguide layers and surrounding adjacent media $n_f$ and $n_c$.

Integration of resonant WGGs with thin-film coatings may provide low sidebands surrounding the resonance regime, achieving high-quality near ideal filter properties. Such filters are disclosed in U.S. Pat. No. 5,598,300 to Magnusson and S. S. Wang (1997) (hereinafter the '300 patent), which is hereby expressly incorporated herein by reference in its entirety. Generic GMR filters and their many applications are described in U.S. Pat. No. 5,216,680 issued to R. Magnusson and S. S. Wang.

Modeling of the Present Waveguide Grating Devices

Rigorous coupled wave analysis (RCWA) [Gaylord and Moharam, 1985; Moharam, et al., 1995a; and Moharam, et al., 1995b], all three of which are expressly incorporated herein by reference, is a numerical tool that may be used to accurately model the present waveguide grating devices based on the use of certain known parameters of the waveguide grating. "Modeling," as used herein, means to determine the spectral characteristics, i.e., the fraction of the incident wave power that is reflected and transmitted through a waveguide grating device at any wavelength of interest. This includes determining the GMR spectral locations, shape, and width of GMR peaks or notches, and reflectance and transmittance in the sidebands (i.e. outside the resonance region). For a rigorous analysis and development of these theories see Magnusson and Wang U.S. Pat. No. 5,216,680, which is hereby expressly incorporated herein by reference in its entirety, and [Wang and Magnusson, 1995], which is also hereby expressly incorporated herein by reference in its entirety. However, a simplified model employing waveguide theory is useful to provide physical insight and approximate resonance locations. This theory is detailed in the '300 patent at col. 5, line 6 through col. 6, line 61 for multi-layer waveguide gratings. For a single-layer waveguide grating, this theory is detailed in the '300 patent at col. 7, lines 7 through 38. The present waveguide gratings may be modeled in a variety of different manners. For example, GMR devices may be modeled using a commercially available software such as Gsolver, from Grating Solver Development Company, which implements RCWA. In addition, waveguide gratings may be modeled using finite difference time domain analysis programs such as TFDS, commercially available from Apollo Photonics, or BEAMPROP FULLWAVE, commercially available from Rsoft. Waveguide gratings may also be suitably modeled using finite element analysis.

Figure 2:
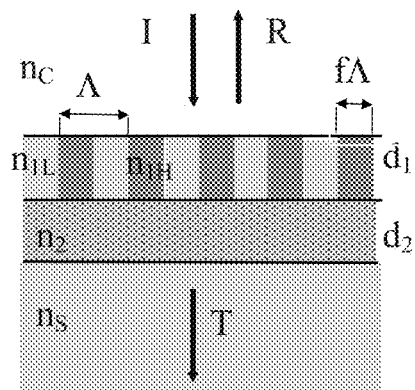

The present waveguide gratings formed from multiple layers may be modeled using RCWA. In using such an analysis, one may assume that the grating layer being analyzed possesses an infinite number of grating periods. In using such an analysis, one may also assume the incident wave or waves are plane waves, and further, one may assume the incidence of the plane waves is normal. FIG. 1 shows a two-layer TE polarization GMR response resulting from an RCWA in which the foregoing assumptions were made. FIG. 2 depicts a two-layer waveguide grating 10, which was analyzed to arrive at the response shown in FIG. 1. Waveguide grating 10 may be part of a two-layer reflection filter (having waveguide layer 12 and grating layer 14) designed for an ionic, self-assembled polymer waveguide layer with a photoresist grating layer deposited on the polymer waveguide layer.

Although the assumption that the number of grating periods is infinite may be made in using RCWA to analyze the present waveguide gratings, the number of such grating periods is finite. However, in recent experiments at microwave wavelengths, RCWA has been demonstrated to accurately predict the GMR spectral locations and lineshapes of finite-size structures [Tibuleac, et al., 2000]. Microwave experiments on GMR filters indicate that finite-size grating layers with as few as twelve periods may yield GMR notch filters with a decrease in the transmittance spectrum from ~81% outside resonance to ~2% at resonance. The foregoing GMR filters have, of course, been planar and not fabricated on the end of a waveguide.

Controlling lineshape parameters such as center wavelength, linewidth, and sideband response may be achieved by carefully selecting the parameters of a waveguide grating device. Low sideband responses (e.g., FIG. 1) may be achieved by choosing the grating layer thickness to be one-fourth of the resonant wavelength. Filter linewidth is affected in part by the strength of the guided-mode confinement and the coupling efficiency of the waveguide grating. As used herein, "mode confinement" means the ratio between the power contained in the core of a mode and the power contained in the core and cladding of a mode. Lineshape may be adjusted by modifying the grating layer fill factor, the grating modulation, and the difference between the average refractive index of the grating layer and the refractive indices of the surrounding regions or media. As used herein, "grating modulation" means the difference between the high and low refractive indices of the grating layer. The filter central wavelength is affected in part by the periodic structure of the grating layer (as used herein, "periodic structure of the grating layer" includes grating layer parameters such as grating period, shape of the gratings, the dimension of the gratings, amplitude, and periodicity of the gratings), the refractive indices of the grating layer, and the refractive index of the waveguide layer (or refractive indices if more than one waveguide layer is utilized within the waveguide grating). Additional parameters that may be manipulated to affect lineshape include the relative spatial phases of incorporated gratings, which may be shifted, and the periodic structures of any grating layers, which may be chosen to be dual-line [Tibuleac, 1996]. As used herein, "dual-line" refers to the presence of two peaks (or notches) in the spectral reflectance (or transmittance) dependence. Since waveguide grating devices are polarization dependent in 1-D (i.e., one-dimensional) grating layers, polarization insensitive devices may be designed by implementing crossed (i.e., 2-D) waveguide gratings.

The present waveguide grating devices may also be designed an inverse approach if certain properties of the needed GMR device are known. If the properties of the needed GMR device are known, these parameters may serve as input parameters into a search and optimization algorithm such as a genetic algorithm [Goldberg, 1989] employing RCWA to calculate the reflectance and transmittance spectra of the devices during the optimization process. Such methods to design GMR filters have been reported in references [Tibuleac, et al., 1997; Zuffada, et al., 1998; Zuffada, et al., 1999; Tibuleac, 1999]. The use of one such genetic algorithm is disclosed in the Appendix hereto.

Biomedical/Chemical Sensing

A biosensor is an analytical device that integrates an immobilized biologically sensitive material, such as enzyme, antibody, DNA, cells, or organic molecules, with an electrochemical, piezoelectric, optical or acoustic transducer to convert a biochemical response into a signal that can be used for measurement, interpretation, or control. Accurate, real-time, direct measurement of biologically related substances eliminates expensive and complex sample preparation that is required in ex situ lab processing. Electrochemical and optical sensors are the most widely used and versatile biosensing methods [Collings and Caruso, 1997; Kersey, 1996]. Optical biosensors provide a fast, accurate, safe, and robust means of analyte detection. All fundamental characteristics of light as it interacts with matter can be used in measurement, including intensity, frequency, phase, and polarization changes. A major advantage of optical detection methods over other techniques is the ability to probe surfaces and films in a non-destructive manner. In addition, optically based sensors are generic elements that can be used to sense a wide variety of analytes that might not be possible with other methods, such as gases, proteins, various types of micro-organisms, and metabolites such as glucose. The use of optical fibers in biosensing systems allows a high degree of geometrical versatility, including component miniaturization, and continuous, real-time, remote monitoring of very small sample domains. Optical fiber sensors are convenient devices that are free from electrical interference and are generally biocompatible for in vivo testing. The ability to provide remote, continuous monitoring is a distinct advantage when testing hazardous materials, in vivo testing, or down-well environmental measurements.

Current fiber optic sensor technology includes fluorescence [Golden, et al., 1994; Abel, et al., 1996], total internal reflection fiber sensors [Bolin, et al., 1989], reflection intensity [Tugendhaft, et al., 1997; Jin, et al., 1997; Johns, et al., 1998], surface plasmon resonances [Jorgenson and Yee, 1993; Jung, 1997; Furlong, et al., 1996a; Slavik, et al., 1997b; Slavik, et al., 1997a; Slavik, et al., 1998; Homola and Slavik, 1996; De Maria, et al., 1993; Melendez, et al., 1997], and fiber bundle arrays utilizing fluorescent detection materials [Ferguson and Walt, 1997]. While fiber optic sensors are the focus here, there are many other designs in the area of optical sensing. Capillary optical sensors utilize fiber optic couplers and capillary tubes that are chemically modified on the inner surface. Optical absorbance or fluorescence is implemented as the unit of measure. Ellipsometry is used to detect refractive index or thickness changes in biological sensing layers. Sensors utilizing planar optical waveguides [Collings and Caruso, 1997; Melendez, et al., 1996; Sharma and Rogers, 1994] include total internal reflection fluorescence, attenuated total reflectance, reflectomeric interference spectroscopy, as well as thin film devices including the resonant mirror developed by Cush, et al. [Cush, et al., 1993], grating couplers [Sychugov, et al., 1997], and Mach-Zender sensor devices [Luff, et al., 1998]. Fabrication of optical sensor elements using transparent sol-gel, can increase sensor sensitivity [Cunningham, 1998]. The primary advantage of fiber optic sensing over other optical configurations is the real-time, remote operation of the sensor.

Current Technology

The surface plasmon resonance (SPR) is a widely used optical detection method that is highly sensitive to changes in the optical properties at the sensor surface, such as refractive index or thickness. The term surface plasmon (SP) is based upon an electromagnetic field charge-density oscillation that can occur at the surface of a conductor. When this electromagnetic coupled mode of excitation travels along the interface between a metal and another medium, it is referred to as a surface plasmon. These surface waves are bound to the metal-dielectric interface, with an intensity maximum in the surface and exponentially decaying fields perpendicular to it. An SP mode is resonantly excited by TM polarized incident light if the wavevector of the incident light and the surface plasmon wave are matched, as governed by Maxwell's equations. At resonance, reflected light intensity from the metallic surface goes through a minimum at a defined angle of incidence. Phase matching occurs by employing a metallized diffraction grating, or by using total internal reflection from a high index material, such as in prism coupling or an evanescent field from a guided wave. The propagation constant of the plasmon depends upon the refractive index of the adjacent medium, which is within sensing distance of the surface plasmon field.

Conventional surface plasmon sensors include a prism or diffraction grating that is used as the phase matching and transducer element. Commercial [Sethi, 1994] planar SPR sensors include Pharmacia Biosensor's BIAcore and BIAlite systems, and Texas Instrument's Spreeta system [Melendez, et al., 1997; Furlong, et al., 1996b; Ouellette, 1998]. Fiber optic SPR sensors developed by Jorgenson and Yee [Jorgenson and Yee, 1993], and more recently by Slavik, et al. [Slavik, et al., 1997b; Slavik, et al., 1997a; Slavik, et al., 1998] and Jung [Jung, 1997] allow remote, real time monitoring. Commercially manufactured fiber SPR sensors are available from Biacore. A sensor based upon SP wave excitation on the tip of an optical fiber was proposed by De Maria, et al. in 1993 [De Maria, et al., 1993].

A method for fabrication of fiber optic surface plasmon resonance sensors is described by Jorgenson and Yee, and Slavik, et al. This includes removal of the fiber cladding over the sensing region to allow access to the evanescent field of a guided mode. Cladding removal is accomplished by gluing the fiber in a curved slot on a silica block, and subsequently polishing and lapping the cladding to obtain a proximity to the core. The exposed region is covered with a thin layer of gold in order to support an SP wave, with the sensing layer attached at the outer interface. If the two modes are closely phase matched, a guided TM mode in the fiber can excite an SP wave at the outer metal-sensing layer interface, resulting in a detectable minimum in the transmitted light intensity. The wavelength where this intensity minimum occurs is closely dependent on the refractive index of the medium adjacent to the metallic film (sensing layer). Variations in the sensing layer, such as refractive index or thickness, can be detected by monitoring changes in the output intensity. To attain maximum sensitivity, appropriate metal layer and cladding thicknesses must be chosen. Optimizing the sensor sensitivity by increasing metallic layer thickness and decreasing the remaining fiber cladding thickness results in a decrease of the dynamic range of the sensor. To tune the refractive index operation range of the SPR fiber optic sensor, a thin tantalum pentoxide overlayer can be deposited beneath the sensing layer.

Slavik details two modes of operation for the fiber optic SPR sensor [Slavik, et al., 1997a]. In the spectral mode, the output power is monitored as a function of wavelength to indicate an SPR spectral location. A tunable laser or a white light source can be used in this configuration. Experimentally achieved sensor resolutions operating in the spectral mode are reported to be $1.6*10^{-5}$ RIU (refractive index units) for an index range of 1.3952-1.3973. This is based on a spectroscopic resolution of 0.1 nm, and does not account for the lineshape characteristics of the sensor response. In the more widely reported amplitude mode, the output power is monitored at a fixed wavelength. The relative output intensity is detected as a refractive index or thickness change causes a shift towards or away from a resonance location. Small changes in the transmitted intensity are measured and calibrated to a specific refractive index or thickness change. Resolutions for the amplitude mode are reported as low as $9\times10^{-6}$ RIU for an index range of 1.4105-1.4163, assuming an optoelectronic system that can resolve changes in optical power to 1%. A particular intensity response provides two solutions for a change in refractive index or thickness; one going towards the resonance dip and one away from it. The resolutions reported are based on an experimentally determined resonance shift of approximately 12 nm with a 80 nm linewidth for a refractive index change from 1.3952 to 1.3973. To perform remote, real-time measurements with this sensor, an aluminum mirror must be deposited on the fiber endface to redirect the output light.

Other fiber sensors include fluorescent excitation and detection in the evanescent field of an optical fiber. As the evanescent field extends to the cladding sensing region, fluorophores coated on the outside of the fiber are excited. Depending on the biological material that is being sensed, a particular wavelength of light indicating a biological recognition can be captured by the fiber optic probe and analyzed using spectroscopic detection elements. This requires very sensitive detection equipment such as photomultiplier tubes since the captured signal is very weak. Accuracy and repeatability is an inherent weakness for this device. Furthermore, detection applications are limited by the bioselective agents available.

Advantages of the Present Waveguide Grating Devices Over Current Technology

Comparison of biosensor performance is best accomplished through a figure of merit [Cunningham, 1998]. Device characterizations that can be included in a generic figure of merit include sensor sensitivity, resolution, and dynamic range. The sensitivity of a biosensor is defined as the measured response for a particular amount of material that is detected. For example, a GMR resonance shift of 11 nm for a thickness change of 20 nm results in a sensitivity value of 0.55 nm shift per 1 nm material added. However, the sensitivity value does not consider sensor limitations; rather, it indicates the maximum achievable sensitivity to the analyte being detected. Resolution of the sensor includes the realistic component limitations such as spectroscopic equipment resolutions, power meter sensitivities, bioselective agent response, and linewidth considerations. The lineshape response has a great impact on the accuracy of spectroscopic sensors in distinguishing between wavelength shifts. For highest confidence limits, the resolution for resonant sensors can be defined by the linewidth (full width, half maximum power), assuming the equipment has a higher resolution. For example, the refractive index sensor depicted in FIG. 20 has a maximum resolution of $3*10^{-4}$ RIU, when considering only spectroscopic resolution limitations of 0.1 nm. However, the detected response is limited by the linewidth of the device, which is 0.8 nm in this case. Under this criteria, the smallest RIU change that can be accurately detected with this sensor is $4*10^{-3}$, although the sensitivity is higher. By normalizing the resonance shift with the linewidth, a realistic evaluation of a resonance sensor performance can be determined. A comparison of sensor sensitivity, resolution and dynamic range is included below in Table 1. The dynamic range (or usable range) of a sensor is defined as the range where discrimination between responses can be detected. Materials used in fabrication and the sensing medium generally limit this range. In addition, these three parameters are generally inter-related. For example, for SPR sensors, as the operational range of refractive index values that can be detected is increased, the sensor sensitivity decreases.

Low loss dielectric materials may be used as either the grating layer or the waveguide layer of the present devices, and absorption losses are not a physical limitation of the present devices. Linewidths for the present devices may be typically less than 5 nm, with well-defined resonance shapes that may provide accurate, well-defined measurements. Two separate resonance locations for TE and TM polarizations are available for detection in the present devices. Accordingly, accuracy and reliability of the present devices is greatly enhanced over other sensors types, since each polarization can act as a reference for the other. In addition, it may be possible to obtain actual refractive index and thickness values of the sensed medium since two measured values are obtained. In contrast to that which may be achieved using the present devices, for sensors that utilize only TM polarization, such as surface plasmon resonance (SPR) sensors, the refractive index of the sensed medium or the sensed layer thickness must be determined beforehand, since both parameters cannot be determined from the same measurement.

Current fiber optic sensors, including the SPR, require the sensing region to be along the length of the fiber, which increases fabrication complexity and spatial sensing resolution. For the present devices, however, the sensing element is located on the waveguide endface, such as the endface of a fiber, thus permitting highly-accurate, small-proximity sensing. Furthermore, waveguide sensor arrays, such as optical fiber sensor arrays, may be readily implemented to simultaneously detect a wide variety of analytes, such as DNA sequences. A calibration fiber may be integrated in a bundle of the present devices to further increase accuracy for in vivo or remote measurement.

Current fiber optic array sensors utilize fluorescence indicators and are less sensitive than the present devices. Additionally, since the deposition of dielectric thin films on

TABLE 1

Comparison between the surface plasmon sensor and guided-mode resonance fiber sensor.

| Sensor type | Max. Linewidth Response | Max. Sensitivity | Max. Resolution (equipment resolution 0.1 nm) | FOM: Sensor Resolution (w/linewidth) | Dynamic range |
|---|---|---|---|---|---|
| SPR sensor | 80 nm [Slavik, et al., 1997a] | 6250 nm/RIU | $1.6 * 10^{-5}$ RIU | $1.3 * 10^{-2}$ RIU | 1.352-1.3973 |
|  | 30 nm [Slavik, et al., 1998] | 1875 nm/RIU | $5.3 * 10^{-5}$ RIU | $1.6 * 10^{-2}$ RIU | not available |
| Fiber GMR sensor (FIG. 20) | 0.8 nm | 310 nm/RIU | $3 * 10^{-4}$ RIU | $2.6 * 10^{-3}$ RIU | 1.34-1.36 RIU |
|  | 1.7 nm | 330 nm/RIU | $3 * 10^{-4}$ RIU | $5.1 * 10^{-3}$ RIU | 1.3-1.7 RIU |

The present devices (e.g., the fiber GMR sensors in Table 1) can be highly sensitive to the parameters of the waveguide gratings. Thus, the grating period, filling factor, number of layers, layer thicknesses, and refractive indices may be tailored for a specific waveguide grating device sensitivity and operational dynamic range. This flexibility allows the resonance wavelength, linewidth, and degree of sensitivity to be tailored for specific applications. By using a genetic algorithm program to design the present devices, specific design criteria such as sensing range or sensitivity may be realized. In general, the present waveguide grating devices have a much higher operational sensing range and greater sensor sensitivity than other fiber optic sensors. In addition, by utilizing biologically sensitive material, such as biopolymers to fabricate the waveguide grating, increased waveguide grating sensitivity may be achieved.

optical fiber endfaces is well-known in the art, the present devices are suitable for mass production. Moreover, an array of the present devices may be fabricated simultaneously using standard thin film deposition methods well known in the art such as dipping, sputtering, spin coating, thermal evaporation, electron-beam evaporation, molecular beam epitaxy, metal-organic chemical vapor deposition, chemical vapor deposition, and liquid phase epitaxy, and submicron grating fabrication technology such as contact printing, and patterning techniques well known in the art such as holographic interferometry, photolithography, electron-beam lithography, and laser-beam lithography. Further still, other detection devices and techniques, such as SPR sensors or fluorescent detection, may be combined with the present devices, which utilize the GMR effect, to increase the flexibility of the present devices in a system for spectral filtering.

Applications for the present devices and systems include use as fiber optic sensors for chemical/biochemical measurement in widespread applications that range from implantable devices used for continuous in vivo measurement to ex vivo analysis in a laboratory. Additionally, in fiber optic communications, the present device may be used to reject or transmit signals for multiplexing/demultiplexing of multiple wavelength channel systems. It is also to be understood that the present waveguide grating devices include multiple waveguides having ends with endfaces, on each of which waveguide gratings may be fabricated. Thus, the present devices may be used as sensors having multiple waveguides with waveguide gratings fabricated on the respective ends thereof. The present device also includes a waveguide, such as an optical fiber, having an end with an endface on which a waveguide grating is fabricated, which waveguide is adjacent to a second waveguide, such as an optical fiber, having an end with an endface onto which a waveguide grating may be fabricated. The waveguide gratings on the two waveguides may be oriented such that a signal propagated through the first waveguide may be reflected at least in part after contacting the first waveguide grating such that it then contacts the waveguide grating of the second waveguide and, thereafter, may be reflected by the second waveguide grating such that the signal is then transmitted through the second waveguide in a direction moving away from the second waveguide grating. In such an embodiment, the present device is a dual fiber sensor. Some applications include:

Feedback control in artificial organs;

Dynamic intravascular blood gas sensor used to detect oxygen saturation of hemochromes (hemoglobin, myoglobin) and carbon dioxide levels in major blood vessels or cardiac chambers. Specifically, for the detection of cardiac shunts during catheterization, to estimate cardiac output from arterio-venous oxygen difference, or for use in the care of fetuses to determine oxygen saturation data. Inadequate blood oxygen levels and carbon dioxide elimination are indications of respiratory and metabolic imbalances. By continuous, real-time monitoring of these levels in the blood, dynamic corrections to patient oxygen ventilation or pharmacological agents can be administered;

Glucose sensor used to detect blood/tissue glucose levels. Qualitative measurement based on refractive index differences correlated to glucose concentration levels can be used. A more accurate quantitative measurement is made by employing bioselective agents such as glucose oxidase. Glucose oxidase changes its chemical properties (and refractive index) depending on the concentration of glucose available in the detection sample;

pH sensor used to monitor blood/tissue acidity levels can be implemented by employing a pH sensitive biosensitive layer on the fiber endface GMR device that changes refractive index for different blood acidity levels;

Tumor sensors to assist in surgery for tumor removal based on an increase in refractive index from the cancer cells; and Brain tissue sensors to locate neuro structures for guidance during neurosurgery. As the refractive indices of tissues vary in the gray and white matter of the brain, the present device may act as a sensor to distinguish between the two types of tissues. For similar reasons, the present devices may also be used as sensors for detecting brain tumors or lesions, etc.

Fuel tank sensor to detect the level of a liquid in a container, or the density or composition of gases inside a fuel container based on changes in the refractive index of the medium.

Oil/fuel quality sensor to detect changes in the chemical properties that induce refractive index changes in the oil or fuel. For example, one of the present devices could be used as a real-time sensor in an automobile that detects when engine oil needs replacement.

Setup for Measuring Spectral Reflectance from Present Devices

Figure 9:
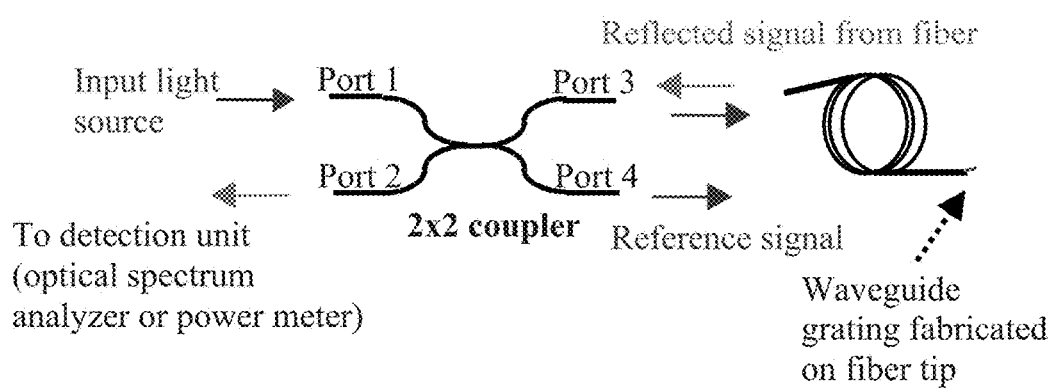
FIG. 9. Schematic of a test setup to measure properties of light (spectrum, polarization, and/or power) from the present waveguide gratings.

As explained herein and in more detail in the Examples below (e.g., Example 3), the present devices are suitable candidates for use as spectroscopic sensing elements (i.e., filters) due at least in part to the narrow linewidths and high sensitivities of the guided-mode resonance peaks to variations in the physical parameters of the present devices (layer thicknesses, refractive indices, grating fill factor, and substrate and cover refractive indices). Thus, the present devices may be designed for a specific sensitivity, resolution, and operational dynamic range. This flexibility allows the resonance wavelength, linewidth, and degree of sensitivity to be tailored for specific applications. A sensor may be optimized to enhance sensitivity to specific parameters, such as refractive index and/or thickness. Since dielectric materials may be used in the fabrication of the present devices, many design configurations are available. In FIG. 9, one embodiment of a setup for use in monitoring the reflectance from one of the present devices is depicted. In general, the setup may be used to measure properties of light (spectrum, polarization, and/or power) reflected from the present devices The setup includes an input light source 30, a 2×2 optical coupler 20, and a detection unit that is not illustrated. Input light source 30 enters 2×2 coupler 20 at input port 22, and coupler 20 divides the power of light incident from input port 22 between output ports 26 and 28. As depicted in FIG. 9, output port 26 is coupled to one of the present devices, which includes a waveguide 16 (such as a fiber) on which waveguide grating 10 is disposed. The reflected power 34 from the present device is equally split between input port 22 and port 24. Port 24 is coupled to a detection unit, which measures the properties of light reflected from the present device. To monitor the intensity of the reflected signal 36 using a fixed wavelength laser source, the detection unit may be an optical power meter, such as a Newport 835 optical power meter. Alternatively, to monitor spectral shifts of the GMR resonance, the detection unit may be an optical spectrum analyzer (such as an Anritsu MS9001B), or a monochromator (Burleigh model) and an optical power meter. Input light source 30 may be broadband (such as an LED or white light source), or a tunable laser (such as Ti:Sapphire or a semiconductor type). To detect the polarization state of the reflected signal 36, an optical polarizer should be placed so that it receives reflected signal 36 prior to the detection unit. The setup depicted in FIG. 9 permits various medium parameters to be monitored remotely and in real-time.

The present device includes multiple sensors, at least one of which is a waveguide having an end with an endface on which a waveguide grating is fabricated, bundled in an array, such that many types of sensors may be simultaneously utilized. A potential application is to integrate this type of bundled array with an intravenous (IV) tube that is inserted into a patient's artery. By integrating the biosensor array into the polymer shunt used for insertion of the IV tube, real time, accurate, continuous monitoring of blood gases, glucose and pH levels can be accomplished without loss of patient blood.

This is particularly useful for monitoring changes in blood gas/glucose levels during surgery, or critically ill patients in intensive care units.

The following examples are included to demonstrate specific embodiments of the invention. Example 1, however, does not include a description of an embodiment of the present devices. Instead, it includes a description of fabricating a diffractive grating (i.e., a grating layer) on a fiber endface. As the diffractive grating is not also a waveguide layer, it is not a waveguide grating. However, the description accompanying Example 1 may be useful in creating the present devices because the waveguide gratings of the present devices require a grating layer. Further, were the photoresist in Example 1 fabricated on a fiber having a slightly lower refracting index, the photoresist could have served as both a waveguide layer and a grating layer, thereby forming a waveguide grating. It should be appreciated by those of skill in the art that the techniques disclosed in the examples that follow represent techniques discovered by the inventors to function well in the practice of the invention, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the invention. See also [Wawro, 1999] for information identical or similar to the following Examples.

EXAMPLE 1

Example 1 describes a procedure that was undertaken to optimize the manner of fabricating a diffractive grating, but not a waveguide grating, on the endface of a fiber. A high quality cleaving tool was used to obtain flat, optical quality endfaces on both single-mode and multimode fibers. After cleaving, the fibers were visually inspected with an optical microscope to determine endface quality. The fibers were cleaned by immersion in an ultrasonic bath of heated acetone for 30 minutes, briefly dipped in optical grade methanol, and dried with filtered nitrogen gas.

The fabrication procedure was initially optimized by recording efficient submicron diffractive structures on the optical fiber endfaces. Thin films of UV-sensitive Shipley 1805 photoresist (PR) were deposited on the cleaved multimode and single-mode fiber endfaces by a dipping process. It was found that a dilution of 3 parts PR to 5 parts Shipley photoresist thinner yielded an approximate PR thickness of 300 nm. This thickness value was obtained from a test substrate that was dipped in the thinned solution, after which the thickness of the PR layer was measured via ellipsometery. The PR/thinner mixture was filtered before deposition with a glass fiber 0.2 µm particulate filter. No significant curvature of the PR layered on the fiber endfaces was observed in scanning electron microscope pictures for photoresist dilutions of greater than 1:1. After the dipping process, the fibers were soft baked in an oven at 90° C. for approximately 30 minutes. The soft bake improved PR adhesion and response linearity during exposure.

Figure 10:
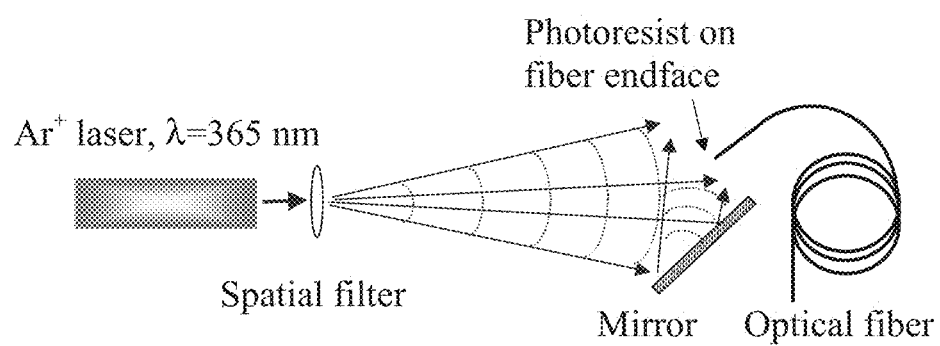
FIG. 10. Single beam holographic setup using ultraviolet laser to record grating pattern on optical fiber endfaces coated with photosensitive polymer.

Diffraction gratings with submicron periods were recorded in the PR layers using holographic interferometry with an UV Argon ion laser ($\lambda$=365 nm) as illustrated in FIG. 10. An exposure power of approximately 110 µW/cm² for 22 seconds was required. The gratings were developed for approximately 20 seconds using Shipley MF-321 developer, resulting in a surface relief photoresist grating.

Figure 23:
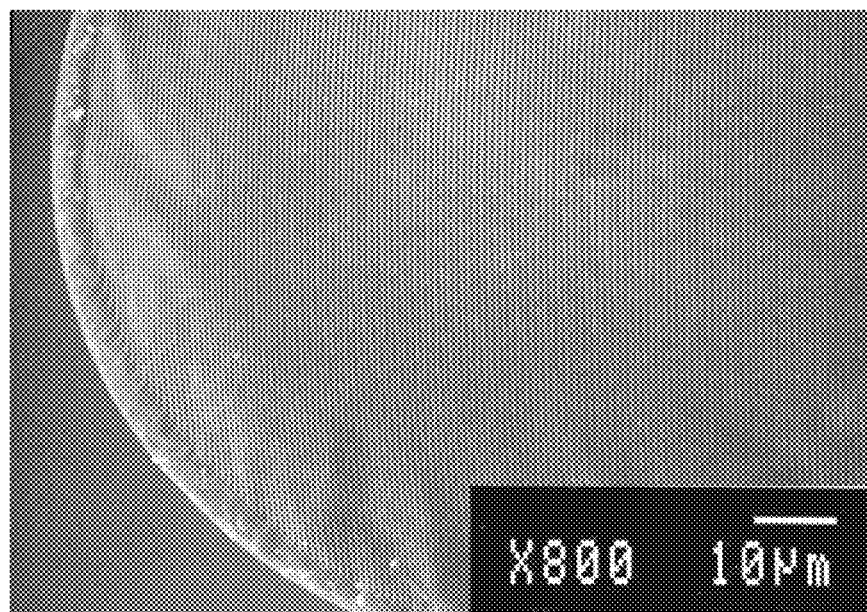
FIG. 23. Scanning electron micrograph of 800 nm period photoresist grating recorded on a multimode fiber endface 800 times magnification.

The grating diffraction efficiency was tested by propagating laser light into the uncoated end of the fiber, and measuring the power output of the transmitted diffraction orders on the end with the diffraction grating. Light from each diffracted order was collimated with a lens and measured individually with an optical power detector head to obtain accurate intensity measurements. The intensity output of the transmitted diffracted orders was measured after coupling a white light source (halogen lamp) into an optical fiber with a 1.2 µm period photoresist grating recorded on its endface. An HeNe laser light ($\lambda$=633 nm) was also propagated into the optical fiber. A diffraction grating with 800 nm period on an optical fiber endface with a 100 µm core diameter was also evaluated, and is illustrated in FIG. 23. This device produced ±1 diffracted orders containing ~50% of the total output power when tested with a HeNe laser ($\lambda$=633 nm). In addition, gratings with a period of 530 nm were recorded on optical fiber endfaces with 6.7 µm core diameters. The ±1 transmitted diffraction orders were measured to contain ~10% of the total power coupled out of the fiber at a wavelength of 442 nm (HeCd laser).

EXAMPLE 2

Fabrication of Waveguide Gratings on Endfaces of Waveguides

In this example, waveguide gratings were fabricated on the endfaces of optical fibers. Once the ends of the fibers were cleaved to form endfaces and cleaned, deposition of dielectric thin-films was required to create a waveguide grating structure. In this example, thin films of $Si_3N_4$ were deposited by sputtering on the clean, uncoated optical fiber endfaces. Silicon nitride is a hard, low loss dielectric material that has a relatively high refractive index (n=2.0). This commonly-used coating can also be patterned by etching in a reactive ion etching (RIE) chamber using standard fluorocarbon etchant gases, such as $CF_4$ or $CHF_3$. An RF-powered sputter machine that housed a single, three-inch $Si_3N_4$ target was used to deposit the nitride films. Inert argon gas was used as the primary sputter gas, with a small amount (~5%) of $N_2$ included to prevent nitrogen depletion of the $Si_3N_4$ target. Nitrogen depletion results in an Si-rich film, which is typically quite lossy. The fibers were mounted in the chamber along with a test substrate made from fused silica to monitor the thickness of the deposited nitride films. The thickness, refractive index, absorption, index grading, and surface roughness of the deposited films were measured using a Woollam V-Vase spectroscopic ellipsometer.

Figure 3:
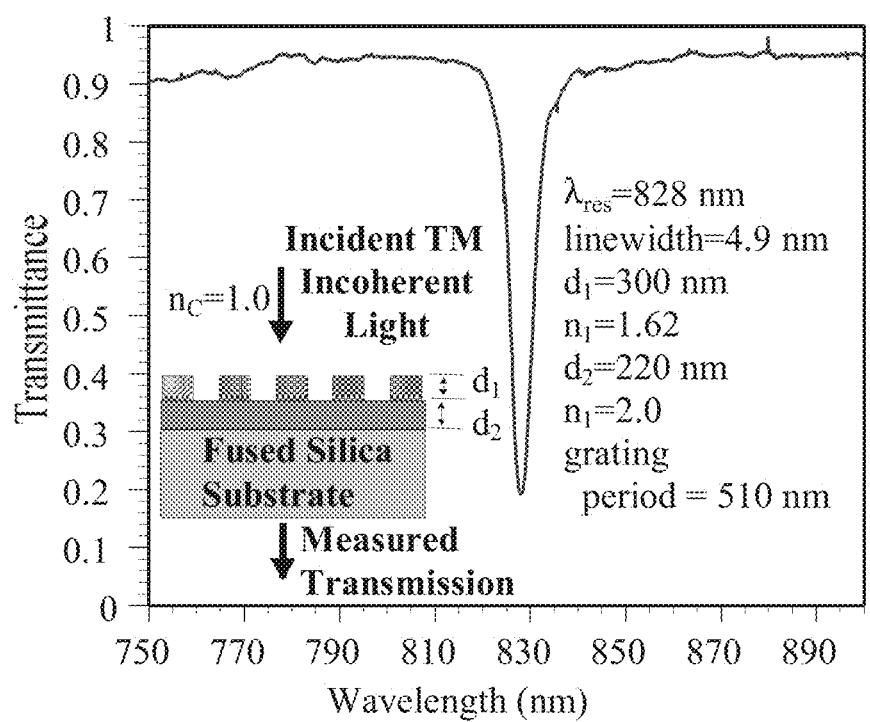
FIG. 3. Transmission measurement at normal incidence performed with a broadband source using an embodiment of one of the present devices that has separate waveguide and grating layers.

Next, the test substrate was spin coated with a 300 nm thick layer of PR and a 510 nm grating was recorded on its surface. Using the spectroscopic ellipsometer, the test waveguide grating structure was subjected to normal incidence transmission measurements, the results of which are indicated in FIG. 3. The parameters of the test waveguide grating structure that led to the results depicted in FIG. 3 are shown therein. The ellipsometer testing source is a fiber coupled Xenon arc lamp monochrometer with a specified resolution of 0.1 nm.

EXAMPLE 3

Figure 4:
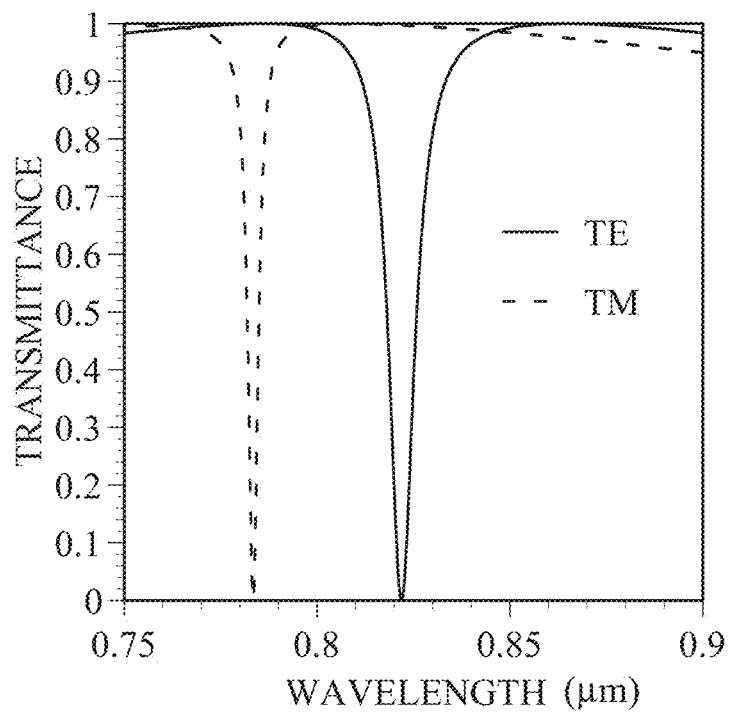
FIGS. 4 and 5. Calculated TE and TM-polarization spectral response (FIG. 4) of an embodiment of one of the present devices that is useful as a filter and has separate waveguide and grating layers (FIG. 5) with the following parameters: $\Lambda$=0.51 μm, $d_1$=0.4 μm, $d_2$=0.18 μm, $n_H$=1.63, $n_L$=1.0, $n_2$=1.9, and $n_S$=1.45.
Figure 5:
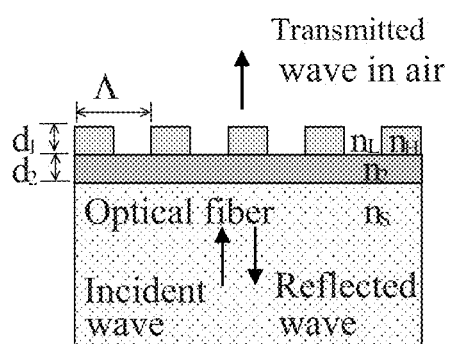
Figure 6:
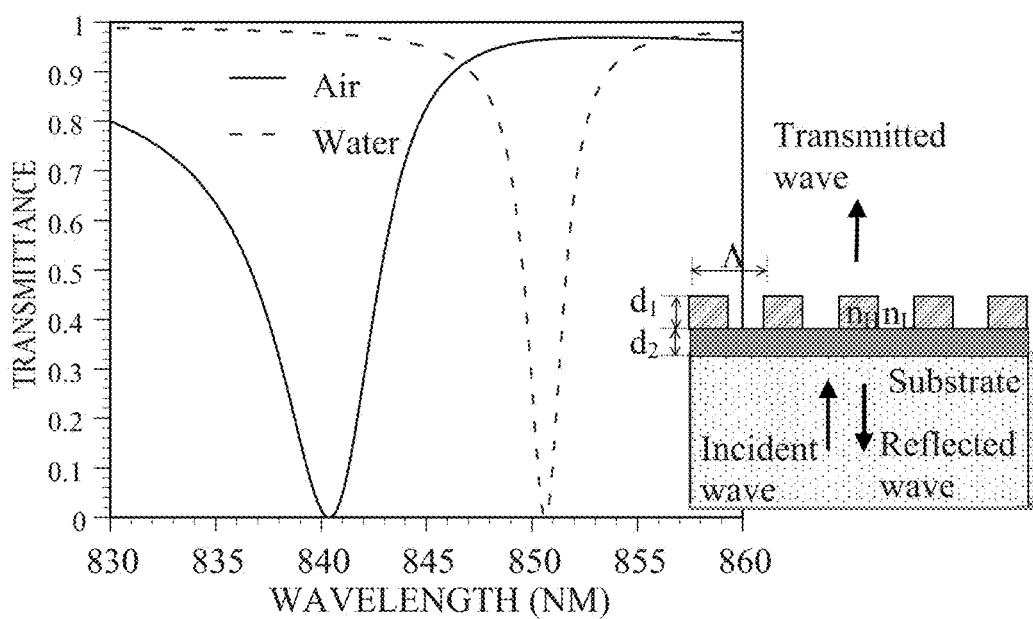
FIGS. 6 and 7. Calculated (FIG. 6) and measured (FIG. 7) spectral shift of one embodiment of the present waveguide gratings on a planar substrate, before and after immersion in water. Physical parameters are as follows: grating period $\Lambda$=510 nm, fill factor f=0.5, $n_2$=2.0, $d_2$=200 nm, $d_1$=300 nm, $n_H$=1.62, $n_L$=1.0 (air) and $n_L$=1.33 (water), TE polarization.
Figure 7:
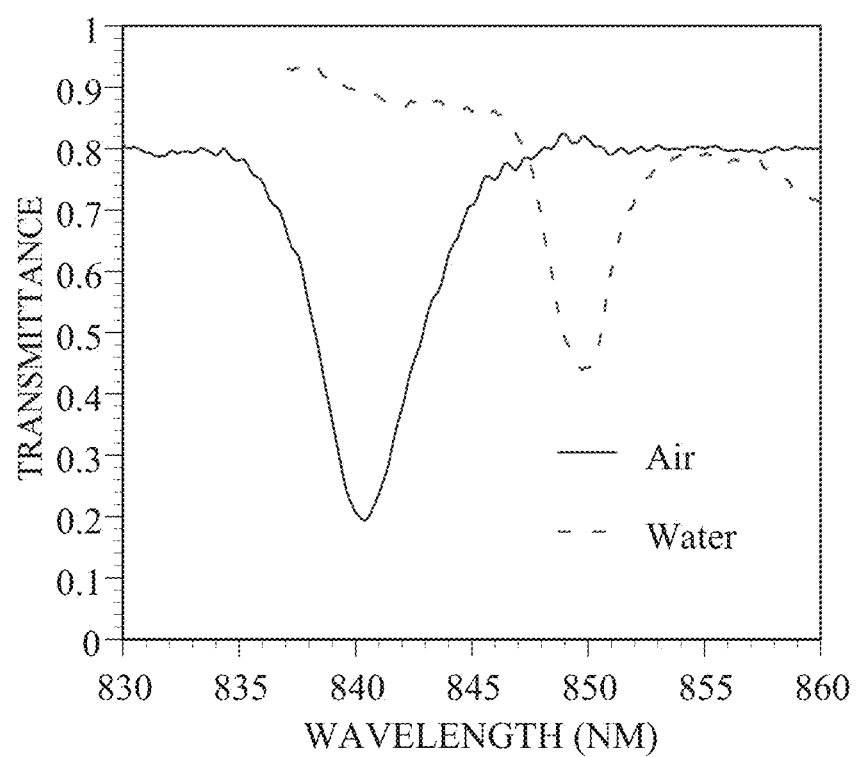

FIG. 4 depicts calculated TE and TM polarization spectral responses of a waveguide grating with the cross section shown in FIG. 5, having the following parameters: grating period, $\Lambda$, is 0.51 µm; thickness, $d_1$, is 0.4 µm; thickness, $d_2$, is 0.18 µm; refractive index, $n_H$, is 1.63; refractive index, $n_L$, is 1.0; refractive index, $n_2$, is 1.9; and refractive index, $n_S$, is 1.45. The calculations leading to the results depicted in FIG. 4 were performed with rigorous coupled-wave analysis, assuming plane waves at normal incidence on a structure with an infinite number of grating periods.

Turning now to the details of this experiment, ~200 nm layers of $Si_3N_4$ were sputter deposited on multimode optical fiber endfaces with 100 µm core diameters. PR gratings with 510 nm periods were subsequently recorded to yield waveguide grating devices. The parameters of the devices are as follows: grating period, L, is 510 nm; PR thickness, $d_1$, is 300 nm; $Si_3N_4$ thickness, $d_2$, is 200 nm; refractive index, $n_L$, is 1.0; refractive index, $n_H$, is 1.85; $Si_3N_4$ refractive index, $n_2$, is 1.85; fiber refractive index, $n_s$, is 1.45.

Figure 8:
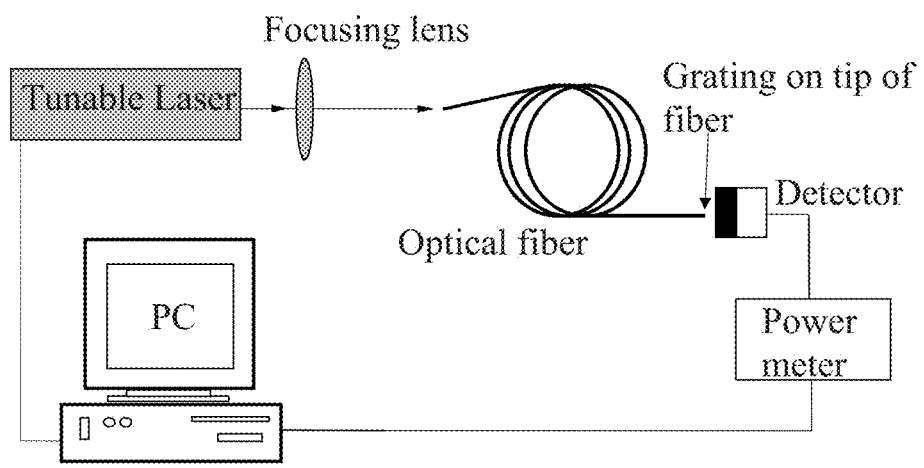
FIG. 8. Test setup used to obtain transmission measurements for the present devices used as sensors.
Figure 11:
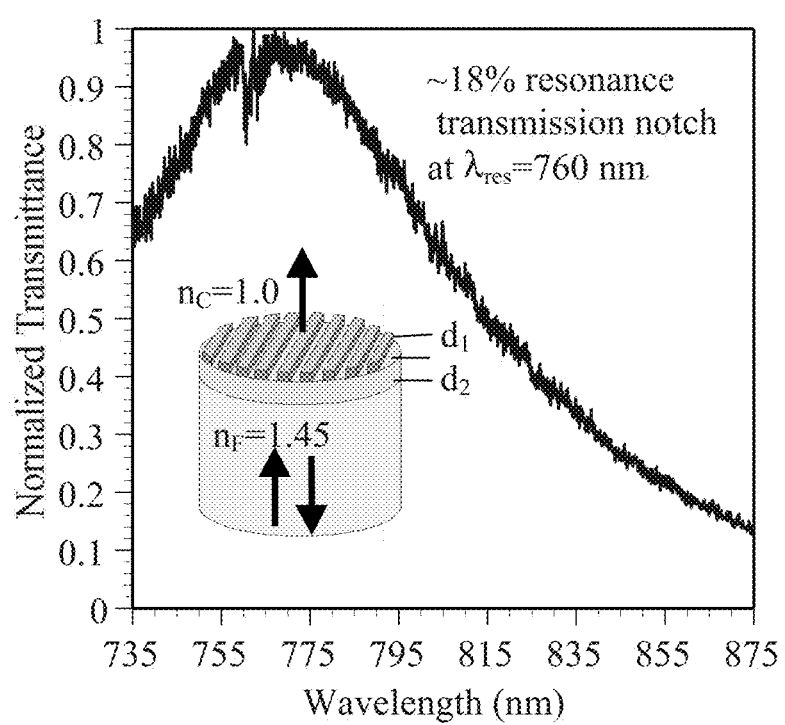
FIG. 11. Raw transmission data measured for an embodiment of one of the present devices having separate waveguide and grating layers that are fabricated using Si3N4 and photoresist, with the following parameters: grating period $\Lambda$=510 nm, thickness of the photoresist grating layer, $d_1$=300 nm, thickness of the waveguide layer (Si3N4), $d_2$=200 nm, low refractive index of the grating layer, which is the same as the refractive index of the cover region ($n_c$ of air), $n_L$=1.0, high refractive index of the grating layer, $n_H$=1.62, refractive index of the waveguide layer (Si3N4), $n_2$=1.85, refractive index of the substrate (silica optical fiber), $n_F$=1.45.

Testing was performed using the setup depicted in FIG. 8. Spectral measurements made with tunable Ti:Sapphire laser ($\lambda$=730-900 nm) indicated GMR notches of ~18% in the transmitted power, which was measured at the output of the optical fiber. FIG. 11 illustrates the measured results without normalization. The low efficiency is partially attributed to the polarization sensitivity of the GMR effect, with TE and TM peaks occurring at different wavelengths and the polarization scrambling induced by propagation through the optical fiber. However, similar devices that are polarization independent may be achieved with two-dimensional gratings. Scattering due to imperfect fiber cleaves and rough silicon nitride films are also contributing factors to a decrease in GMR efficiency. Furthermore, it is assumed for modeling purposes that the wavefronts are essentially planar in nature due to the large core diameter. More accurate modeling may be required to account for the finite 2-D confinement of the incident beam, as well as the finite periodic structure on the fiber endface. It is contemplated that finite element or finite difference modeling would be well-suited for this purpose.

Spectroscopic Sensor Designs

The present waveguide grating devices are well-suited for use as spectroscopic filters due to the sensitivity of the devices to changes in parameters such as the thicknesses of the grating layer or layers and the waveguide layer or layers, the refractive indices of the same, the grating fill factor, and the substrate and cover refractive indices. Factors in addition to the parameters discussed above that may affect the configuration of a given waveguide grating device include the sources available for testing and the required sensor resolution. In general, waveguide gratings made of a single layer (i.e., waveguide gratings in which the at least one waveguide layer and the at least one grating layer are the same layer) are more sensitive to changes in the parameters discusses above than are waveguide gratings made of multiple layers, because the mode confinement of the single-layer waveguide grating is greater or heightened as compared to the mode confinement of multi-layer waveguide gratings.

FIGS. 12-22 illustrate examples of the present waveguide grating devices that may be used as filters/sensors for sensing changes in the parameters of the refractive index and the thickness of material that may contact the waveguide grating. The devices may be placed and utilized in fluid media including water and air.

EXAMPLE 4

Figure 12:
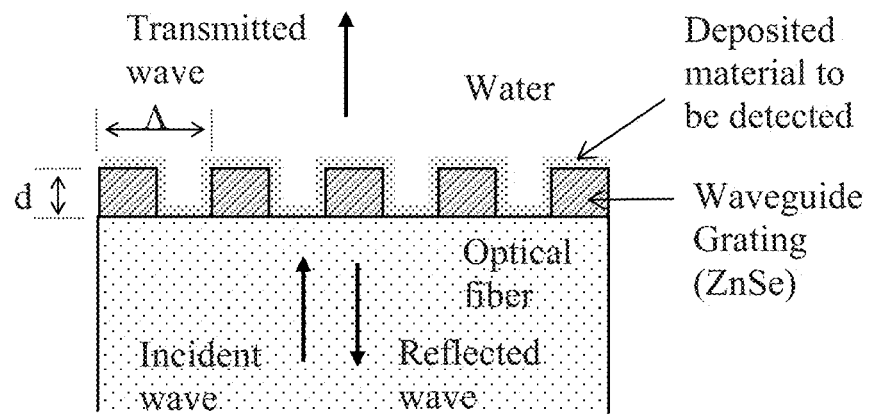
FIGS. 12 and 13. Thickness sensing in water. TE polarization spectral response of an embodiment of the present devices useful as fiber endface reflection filter (FIG. 13). The peak wavelength shifts from 749.6 nm to 751.5 nm and 754.1 nm, as 20 nm and 40 nm of material are added, respectively. The physical parameters of the waveguide grating are as follows (FIG. 12): grating period, $\Lambda$=454 nm, thickness, d=371 nm, refractive indices of the grating layer, n=2.55 (ZnSe) and n=1.33 (water). The refractive index of the material to be detected is n=1.4.
Figure 13:
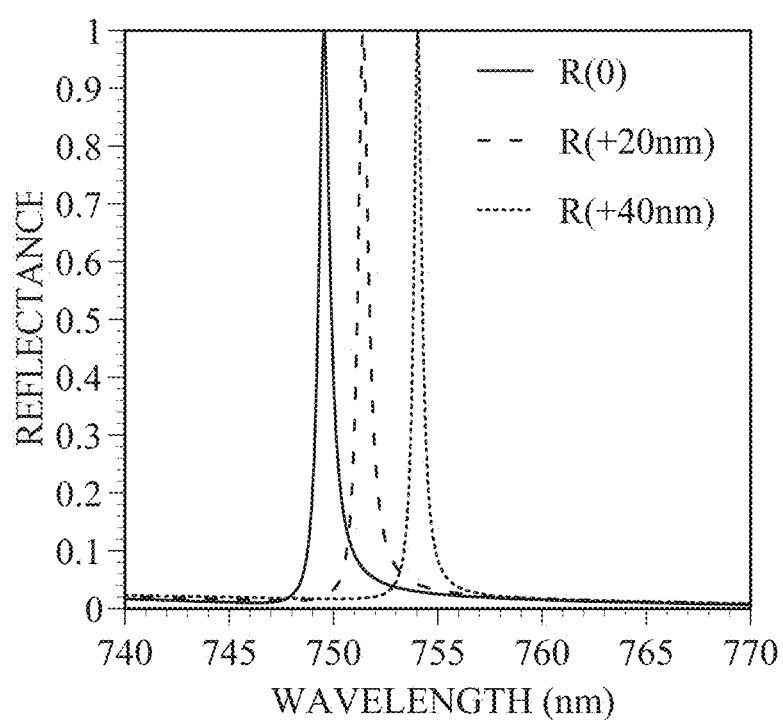

Sensor Placed in Aqueous Media and Used to Sense Changes in Thickness of Material Deposited on Waveguide Grating FIG. 12 illustrates certain parameters of both a sensor designed to detect changes in the thickness parameter of a material in an aqueous media, and a material contacted by the sensor. The waveguide grating is made of ZnSe and is fabricated on an endface of the waveguide, which, in this embodiment, is an optical fiber. Grating period, $\Lambda$, is 454 nm, thickness, d, of the waveguide grating is 371 nm, refractive index, $n_{wg}$, of the waveguide grating is 2.55, and refractive index, $n_{water}$, of water is 1.33. The refractive index of the material to be detected is 1.4. Material is a high index material can be deposited on waveguide grating by plasma etching. The above refractive index and thickness values were chosen to model typical bioselective agents, such as antigen/antibody attachments. FIG. 13 illustrates the TE polarization spectral response of the waveguide grating device illustrated in FIG. 12 to material and to changes in the thickness of material. As shown, a resonance shift of 1.9 nm was determined as 20 nm of material was added to the thickness of waveguide grating, and a 2.6 nm resonance shift was determined as a total of 40 nm of material was added to the thickness of waveguide grating as the peak wavelength shifted from 749.6 nm, to 751.5 nm, to 754.1 nm, respectively. In this case, the degree of resonant central wavelength shift is contributed to two parameter changes: the change in waveguide grating thickness that resulted from adding material to the waveguide grating, and a change in grating layer (which is also the waveguide grating) fill factor. The former parameter may contribute significantly to the resonance shift for fill factor values other than 0.5 [Tibuleac, 1996].

EXAMPLE 5

Figure 14:
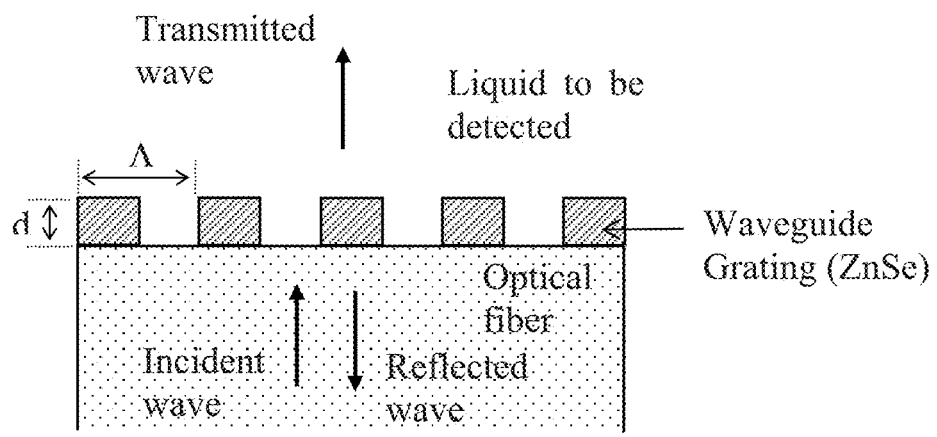
FIGS. 14 and 15. Refractive index sensing in liquid. TE polarization spectral response of an embodiment of the present devices useful as fiber endface reflection filter (FIG. 15). The peak wavelength shifts from 749.6 nm to 752.2 nm and 754.8 nm, as the refractive index of the detected liquid varies from 1.33 to 1.34 and 1.35, respectively. The physical parameters of the waveguide grating are as follows (FIG. 14): grating period, $\Lambda$=454 nm, thickness, d=371 nm, refractive indices of the grating layer, n=2.55 (ZnSe) and n=1.33-1.35 (liquid being detected).
Figure 15:
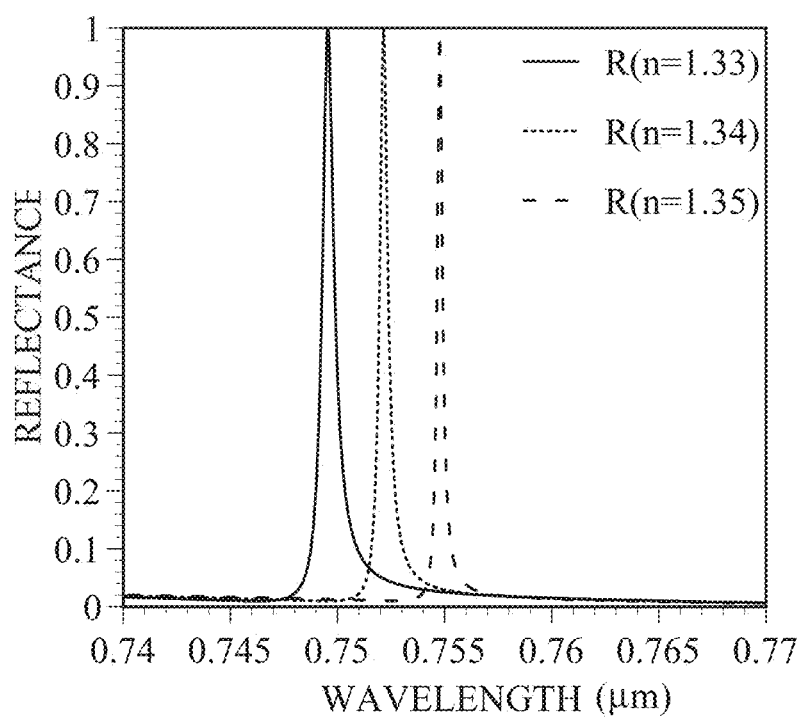

Sensor Placed in Liquid Media and Used to Sense Changes in Refractive Index of Liquid Turning now to FIGS. 14 and 15, the above highly flexible sensor configuration may also be used to detect changes in the refractive index of a media into which it may be placed. The media was liquid, and the refractive index of the liquid changed from 1.33 to 1.35. Accordingly, FIG. 15 illustrates the TE polarization spectral response of the waveguide grating device illustrated in FIG. 14 to the changes in the refractive index of the liquid. As shown in FIG. 15, the peak wavelength shifted from 749.6 nm to 752.2 nm and 754.8 nm as the refractive index of the detected liquid varied from 1.33 to 1.34 and 1.35, respectively.

EXAMPLE 6

Figure 16:
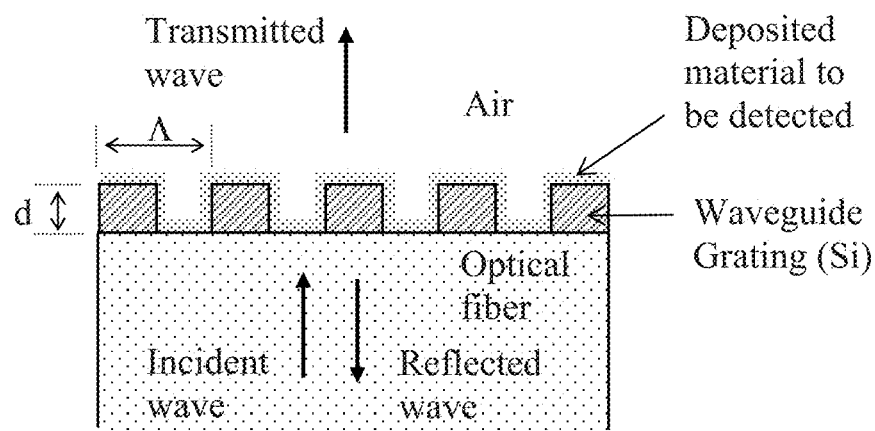
FIGS. 16 and 17. Thickness sensing in air. TE polarization spectral response of an embodiment of the present devices useful as fiber endface reflection filter (FIG. 17). The peak wavelength shifts from 1.554 μm to 1.564 μm and 1.575 μm, as 20 nm and 40 nm of material are added, respectively. The physical parameters of the waveguide grating are as follows (FIG. 16): grating period, $\Lambda$=0.907 μm, thickness, d=1.1 μm, refractive indices of the grating layer, n=3.2 (Silicon) and n=1.0 (air). The refractive index of the material to be detected is n=1.4.
Figure 17:
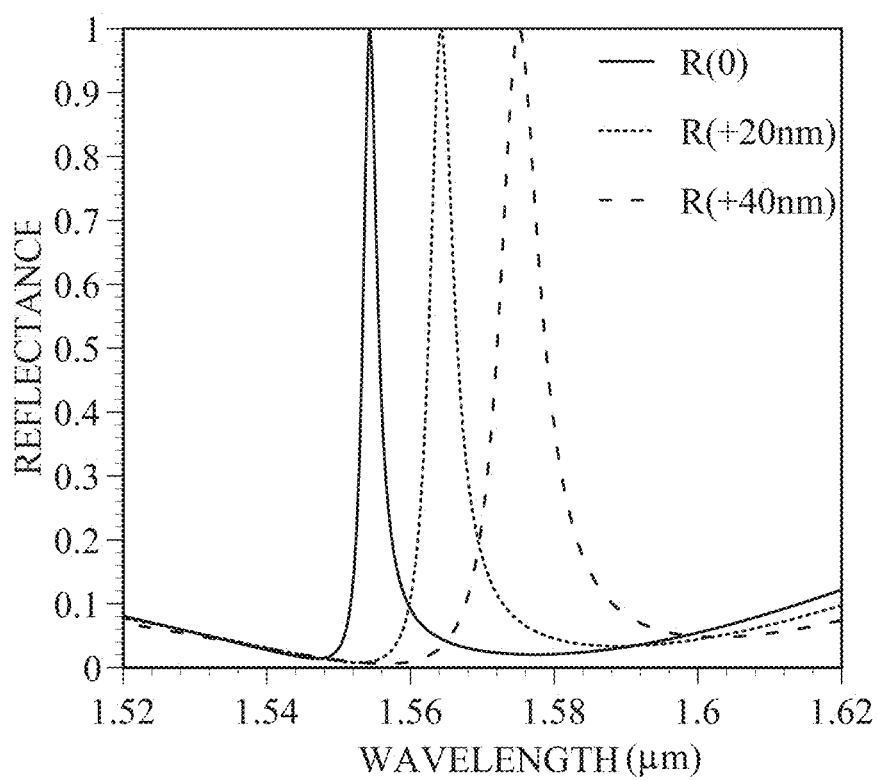

Sensor Placed in Liquid Media, Air, and Used to Sense Changes in Thickness of Material Deposited on Waveguide Grating In FIGS. 16 and 17, a waveguide grating device is shown that may be placed in a media of air. The device may be contacted by a material, which in this case, was deposited on waveguide grating. The device shown was used as a sensor to detect changes in the thickness of material. FIG. 16 illustrates the parameters of the device and material. Waveguide grating is made of Si and is fabricated on endface of waveguide which, in this embodiment, is an optical fiber. Grating period, $\Lambda$, is 0.907 µm, thickness, d, of waveguide grating is 1.1 µm, refractive index, $n_{wg}$, of waveguide grating is 3.2, and refractive index, $n_{air}$, of air is 1.0. The refractive index, $n_{material}$, of the material to be detected is 1.4. FIG. 17 illustrates the TE polarization spectral response of the waveguide grating device illustrated in FIG. 16 to material and to changes in the thickness of material. As shown in FIG. 17, the peak wavelength shifted from 1.554

μm to 1.564 μm and 1.575 μm, as 20 nm and 40 nm of material were added, respectively. Due to the higher index modulation in this sensor design, a resonance shift of 10 nm per 20 nm change in thickness is available for sensing. The incident wavelength was in the range of 1.55 μm, which corresponds to tunable laser diode wavelengths.

EXAMPLE 7

Figure 18:
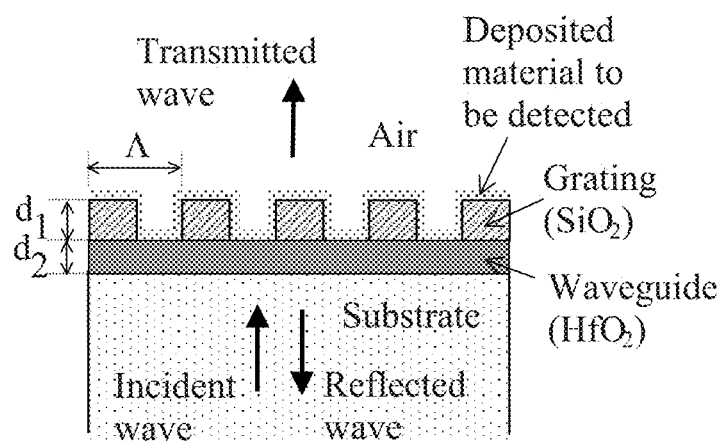
FIGS. 18 and 19. Thickness sensing in air. TE polarization spectral response of an embodiment of the present devices useful as fiber endface reflection filter (FIG. 19). Approximately 1 nm shift for 10 nm of adhered material (n=1.4). The physical parameters of the waveguide grating are as follows (FIG. 18): grating period $\Lambda$=0.349 μm, f=0.5, $d_1$=0.12 μm, $d_2$=0.15 μm, $n_{H,1}$=1.45 (SiO$_2$), $n_2$=2.0 (HfO$_2$), $n_{L,1}$=$n_C$=1.0, $n_S$=1.45.
Figure 19:
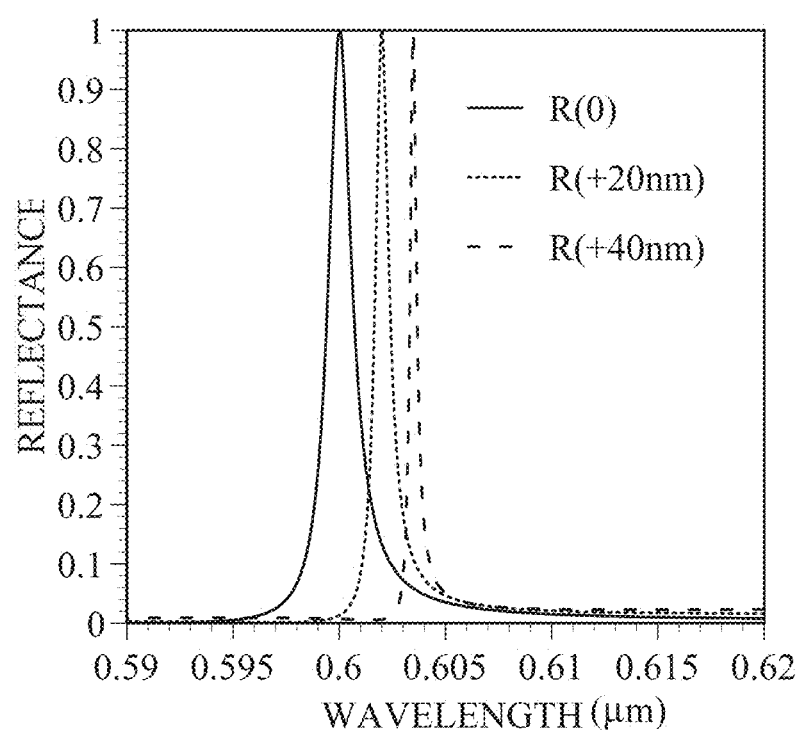

Sensor Placed in Liquid Media, air, and Used to Sense Changes in Thickness of Material Deposited on Double-Layer Waveguide Grating A waveguide grating device with a double-layer waveguide grating is depicted in FIG. 18. The depicted design is useful for thickness sensing in air using a visible incident light source. FIG. 18 illustrates certain parameters of both the device and the material deposited on the waveguide grating of the device. The waveguide grating is composed of a grating layer made of $SiO_2$ in contact with a waveguide layer made of a $HfO_2$, which is fabricated on endface of waveguide. Grating period, Λ, is 0.349 μm, fill factor, f, of grating layer is 0.5, thickness, $d_1$, of grating layer is 0.12 μm, thickness, $d_2$, of waveguide layer is 0.15 μm, refractive index, $n_{H,1}$, of grating layer is 1.45, refractive index, $n_2$, of waveguide layer is 2.0, refractive index, $n_{L,1}$, is 1.0, as is refractive index, $n_C$, and refractive index, $n_S$, is 1.45. FIG. 19 illustrates the TE polarization spectral response of the waveguide grating device illustrated in FIG. 18 to material and to changes in the thickness of material. As shown, a resonance shift of approximately 1 nm was determined for each 20 nm of material added to the thickness of grating layer.

EXAMPLE 8

Figure 20:
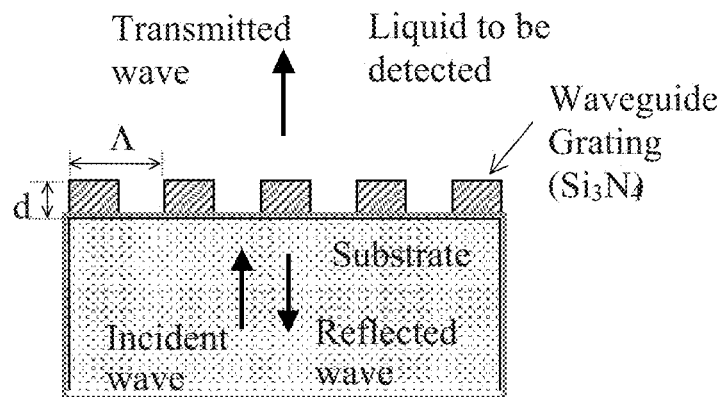
FIGS. 20 and 21. Refractive index sensing in water. Approximately 3.1 nm shift for 0.01 change in refractive index (FIG. 21). The peak wavelength shifts from 807.4 nm to 810.1 nm and 813.3 nm, as the refractive index of the detected liquid varies from 1.34 to 1.35 and 1.36, respectively. Linewidth=0.8 nm. The physical parameters of the waveguide grating are as follows (FIG. 20): grating period $\Lambda$=0.530 μm, f=0.5, d=0.470 μm, $n_H$=2.0 (Si$_3$N$_4$), $n_S$=1.45, $n_L$=$n_C$=1.34, 1.35, and 1.36.
Figure 21:
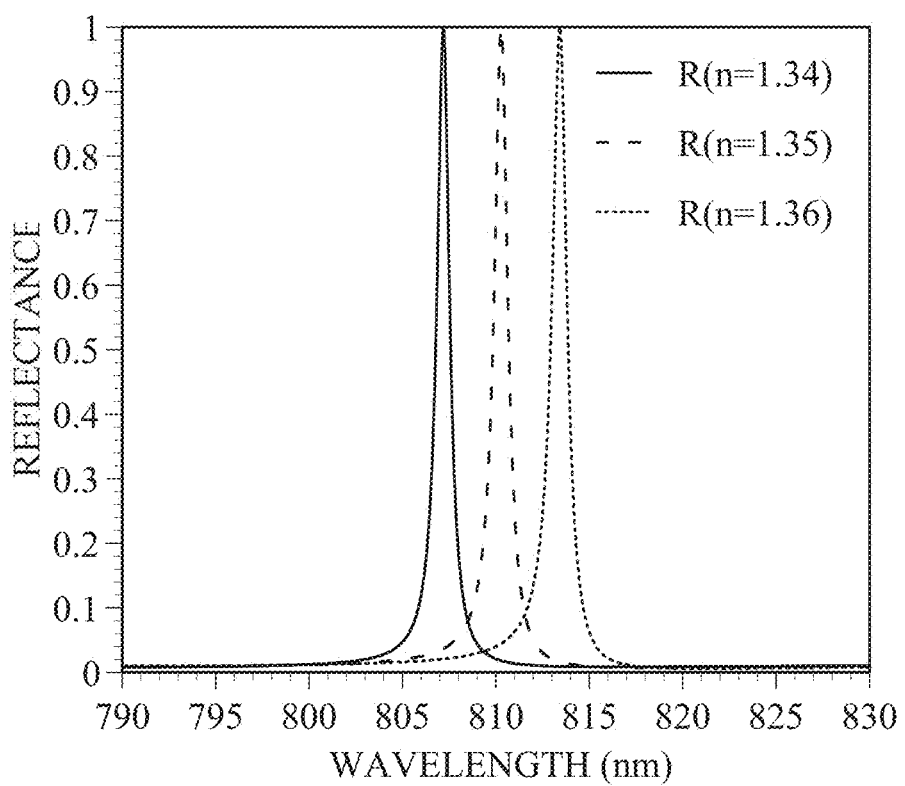

Sensor Placed in Liquid Media and Used to Sense Changes in Refractive Index of Liquid A waveguide grating device with a highly sensitive single-layer waveguide grating is depicted in FIG. 20. The depicted design is useful for refractive index sensing in liquid. This sensor was fabricated using $Si_3N_4$ as the waveguide grating and may be used to detect small or large changes in the refractive index of a liquid. FIG. 20 illustrates certain parameters of the device. Waveguide grating is made of $Si_3N_4$ which is fabricated on endface of waveguide. Grating period, Λ, is 0.530 μm, fill factor, f, of waveguide grating is 0.5, thickness, d, of waveguide grating—is 0.470 μm, refractive index, $n_H$, of the waveguide grating is 2.0, and refractive index, $n_S$, of the substrate is 1.45. Refractive index, $n_L$, of the liquid being sensed is the same as refractive index, $n_C$, of cover region, both of which are determined to range from 1.34 to 1.36. FIG. 21 illustrates the TE polarization spectral response of the waveguide grating device illustrated in FIG. 20 to liquid and to changes in the refractive index of material. As shown, a resonance shift of approximately 3.1 nm was determined for a change in refractive index of liquid of 0.01. The peak wavelength shifted from 807.4 nm to 810.1 nm and 813.3 nm, as the refractive index of the detected liquid varied from 1.34 to 1.35 and 1.36, respectively. Also shown in FIG. 21, the linewidth is 0.8 nm.

Figure 22:
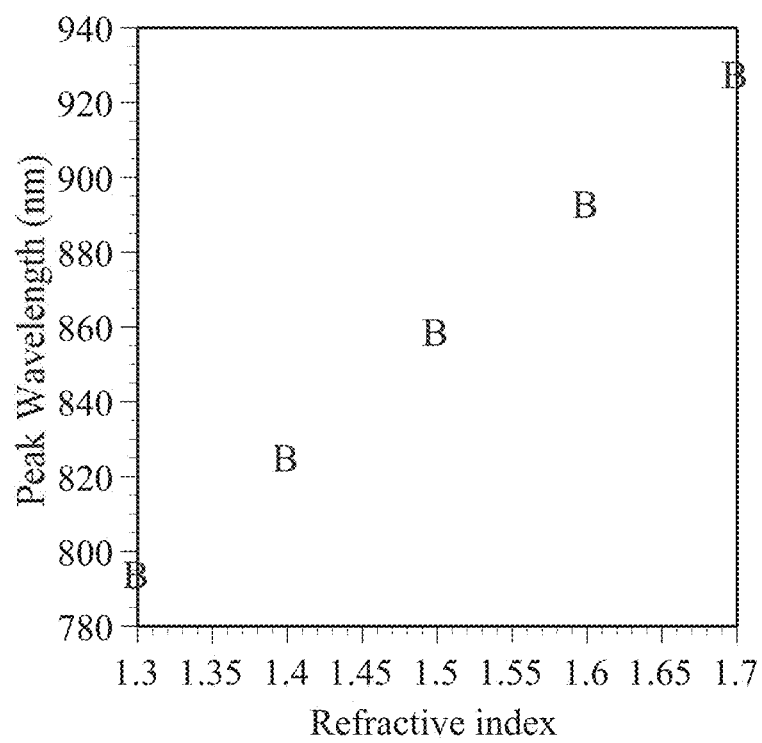
FIG. 22. Plot of peak wavelength shift for large dynamic range sensing. Response is linear and sensitivity is retained for a refractive index range from 1.3 to 1.7. Corresponds to structure described in FIG. 20.

FIG. 22 illustrates the extremely large dynamic range and linear response available for the sensor design depicted in FIG. 20. FIG. 22 is a plot of the reflectance peak wavelength shift that occurred as the refractive index of the detected liquid increased over a large range of refractive index values. The response depicted in FIG. 22 is relatively linear and sensitivity may be maintained for a refractive index range from 1.3 to 1.7. As illustrated by these figures, high sensitivity is maintained for both refractive index ranges, making this design a very attractive and flexible sensor design.

All of the compositions and/or methods and/or apparatus disclosed and claimed herein may be made and executed without undue experimentation in light of the present disclosure. For example, techniques associated with preparing the endfaces of the present waveguides such as cleaving and polishing are known in the art. Techniques associated with fabricating, including dipping and spin coating, heating, and etching, and techniques associated with depositing, including sputtering, thermal evaporation, electron-beam evaporation, molecular beam epitaxy, metal-organic chemical vapor deposition, chemical vapor deposition and liquid phase epitaxy, are known in the art. Techniques associated with patterning, including holographic interferometry, photolithography, electron-beam lithography, laser-beam lithography, and contact printing, are known in the art.

While the compositions and methods of this invention have been described in terms of specific embodiments, it will be apparent to those of skill in the art that variations may be applied to the compositions and/or methods and/or apparatus and in the steps or in the sequence of steps of the method described herein without departing from the concept, spirit and scope of the invention. For example, it is contemplated that waveguide gratings may be fabricated on graded index lenses. Additionally, the waveguide gratings of the present devices may be fabricated on the endfaces of the waveguides by directly recording the grating pattern into a dielectric material such as glass, for example. In such an embodiment, a photosensitive polymer for patterning or etching the grating pattern into the dielectric would not be used. Such fabrication may be realized through, for example, stresses that may be induced by illumination of the dielectric with a laser or an electron beam. For example, chalcogenide glass forms a surface relief grating if exposed to a laser interference pattern. Additionally, the present waveguide gratings may be fabricated on electro-optic waveguides. For example, an electro-optic fiber (such as one commercially available from Sentel Technologies) fabricated from a nonlinear dye-doped polymer having electrodes embedded around the fiber core may be prepared as described above to have an endface on which a waveguide grating may be fabricated. Since the refractive index of the core of such a fiber changes upon the application of a voltage, the resonance transmission or reflection peak may change depending on the refractive index of the core. In such an embodiment, the effect just described may be useful in calibrating the device or tuning it to a specific wavelength band (tunable filter). More specifically, it will be apparent that certain agents that are both chemically and physiologically related may be substituted for the agents described herein, while the same or similar results would be achieved. For example, dielectric materials from which the grating and waveguide layers of the present devices may be made include nonlinear dielectric materials. For example, polymers that incorporate nonlinear materials (for second order or third order nonlinear effects) or semiconductor materials having nonlinear materials therein may be utilized for the present layers. Consequently, present devices having waveguide gratings with such nonlinear materials may be used as wavelength converters (second harmonic generation). All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abel, et al., "Fiber-optic evanescent wave biosensor for the detection of oligonucleotides," *Analytical Chemistry*, 68:2905-2912, 1996.

Avrutsky, et al., "Interference phenomena in waveguides with two corrugated boundaries," *Journal of Modern Optics*, 34:1303-1320, 1989.

Bolin, et al., "Refractive index of some mammalian tissues using a fiber optic cladding method," *Applied Optics*, 28:2297-2303, 1989.

Boye and Kostuk, "Investigation of the effect of finite grating size on the performance of guided-mode resonance filters," *Applied Optics*, 39(21):3549-3653, 2000.

Brundrett, et al., "Normal-incidence guided-mode resonant grating filters: design and experimental demonstration," *Optics Letters*, 23(9):700-702, 1998.

Chen, "Excitation of higher order modes in optical fibers with parabolic index profile," *Applied Optics*, 27(11): 2353-2356, 1988.

Collings and Caruso, 1997 "Biosensors: recent advances," Reports on Progress in Physics, 60:1397-1445, 1997.

Cunningham, Introduction to Bioanalytical Sensors John Wiley and Sons, 1998.

Cush, et al., "The resonant mirror: a novel optical biosensor for direct sensing of biomolecular interactions Part I: Principle of operation and associated instrumentation," *Biosensors and Bioelectronics*, 8:347-353, 1993.

De Maria, et al., "Fiber-optic sensor based on surface plasmon interrogation," *Sensors and Actuators B*, 12:221-223, 1993.

Ferguson and Walt, "Optical fibers make sense of chemicals," Photonics Spectra, pp. 108-114, 1997.

Furlong, et al., "A fundamental approach for biosensor characterization," Proceedings of Sensors Expo, Helmers Publishing, 353-356, 1996a.

Furlong, et al., "Fundamental system for biosensor characterization: application to surface plasmon resonance (SPR)," presented at Chemical, biochemical and environmental fiber sensors VIII, Denver, Colo., 1996b.

Gale, et al., "Zero-order diffractive microstructures for security applications," Proceedings SPIE on Optical Security and Anti-counterfeiting systems, 1210:83-89, 1990.

Gaylord and Moharam, "Analysis and applications of optical diffraction by gratings," Proc. IEEE, 73:894-937, 1985.

Goldberg, "Genetic algorithms in search, optimization and machine learning," Addison-Wesley, Reading, Mass., 1989.

Golden, et al., "An evanescent wave biosensor—Part II: Fluorescent signal aquisition from tapered optic probes," IEEE Transactions on Biomedical Engineering, 41:585-591, 1994.

Homola and Slavik, "Fibre-optic sensor based on surface plasmon resonance," Electronics Letters, 32:480-482, 1996.

Jin, et al., "Limitation of absorption-based fiber optic gas sensors by coherent reflections," *Applied Optics*, 36:6251-6255, 1997.

Johns, et al., "Computational and in vivo investigation of optical reflectance from human brain to assist neurosurgery," Journal of Biomedical Optics, 3:437-445, 1998.

Jorgenson and Yee, "A fiber-optic chemical sensor based on surface plasmon resonance," Sensors and Actuators B, 22:75-81, 1993.

Jung, "Surface Plasmon Resonance Fiber Optic Sensors," Proceedings of the 3rd Pacific NW Fiber Optic Sensor Workshop, Troutdale, Oreg.; 2-8, 1997.

Kersey, "A review of recent developments in fiber optic sensor technology," Optical Fiber Technology, 2:291-317, 1996.

Liu, et al., "High-efficiency guided-mode resonance filter," Optics Letters, 23(19):1556-1558, 1998.

Luff, et al., "Integrated Optical Mach-Zender Biosensor," Journal of Lightwave Technology, 16:583-592, 1998.

Magnusson and Wang, "New principle for optical filters," Applied Physics Letters, 61:1022-1024, 1992.

Magnusson, et al., "Guided-mode resonance Brewster filter," Optics Letters, 23(8):612-614, 1998.

Melendez, et al., "Development of a surface plasmon resonance sensor for commercial applications," Sensors and Actuators B, 38-39:375-379, 1997.

Melendez, et al., "Biological Sensor Systems," presented at Sensors Expo Proceedings, 1996.

Moharam, et al., "Formulation for stable and efficient implementation of the rigorous coupled-wave analysis of binary gratings," *Journal of the Optical Society of America, Part A*, 12:1068-1076, 1995a.

Moharam, et al., "Stable implementation of the rigorous coupled-wave analysis for surface-relief gratings: enhanced transmittance matrix approach," *Journal of the Optical Society of America, Part A*, 12:1077-1086, 1995b.

Norton, et al., "Coupled-mode theory of resonant-grating filters," *Journal of the Optical Society of America, Part A*, 14(3):629-639, 1997.

Norton, et al., "Experimental investigation of resonant-grating filter lineshapes in comparison with theoretical models," *Journal of the Optical Society of America, Part A*, 15(2):464-472, 1998.

Ouellette, "Biosensors: Microelectronics marries biology," The Industrial Physicist, pp. 11-12, September 1998.

Peng and Morris, "Experimental demonstration of resonant anomalies in diffraction from two-dimensional gratings," *Optics Letters*, 21:549-551, 1996.

Rosenblatt, et al., "Resonant grating waveguide structures," *IEEE Journal of Quantum Electronics*, 33:2038-2059, 1997.

Sethi, "Transducer aspects of biosensors," Biosensors and Bioelectronics, 9:243-264, 1994.

Sharma and Rogers, "Biosensors," Meas. Sci. Technol., 5:461-472, 1994.

Shin et al., "Thin-film optical filters with diffractive elements and waveguides," *Optical Engineering*, 37:2634-46, 1998.

Slavik, et al., "Miniaturization of fiber optic surface plasmon resonance sensor," Sensors and Actuators B, 51:311-315, 1998.

Slavik, et al., "Novel surface plasmon resonance sensor based on single-mode optical fiber," Chemical, Biochemical and Environmental Sensors IX, Munich, Germany, 16-18 June, Proceedings of SPIE, 3105:325-331, 1997a.

Slavik, et al., "Optical fiber surface plasmon resonance sensor for an aqueous environment," Proceedings of the International Conference on Optical Fiber Sensors, Williamsburg, Va., pp. 436-439, 1997b.

Sychugov, et al., "Waveguide coupling gratings for high-sensitivity biochemical sensors," Sensors and Actuators B, 38-39:360-364, 1997.

Tamir and Zhang, "Resonant scattering by multilayered dielectric gratings," Journal of the Optical Society of America A, 14:1607-1617, 1997.

Tibuleac and Magnusson, "Reflection and transmission guided-mode resonance filters," *Journal of the Optical Society of America, Part A*, 14:1617-1626, 1997.

Tibuleac, et al., "Direct and inverse techniques of guided-mode resonance filter designs," IEEE Antennas and Propagation Society International Symposium, Conference Proceedings 4:2380-2383, 1997.

Tibuleac, et al., "Dielectric frequency selective structures incorporating waveguide gratings," IEEE Transactions on Microwave Theory and Techniques, 48:553-561, 2000.

Tibuleac, et al., "Resonant diffractive structures integrating waveguide gratings on optical fiber endfaces," Proceedings of IEEE Lasers and Electro Optics Society. Annual Meeting, San Francisco, Calif., November 1999, Conference Proceedings 2: 874-875, 1999.

Tibuleac, Masters Thesis, 1996, University of Texas at Arlington.

Tibuleac, Sorin, Ph.D. Dissertation, The University of Texas at Arlington, 1999.

Tugendhaft, et al., "Reflection intensity optical fiber sensors for the mid-infrared," Applied Optics, 36:1297-1302, 1997.

Wang and Magnusson, "Multi-layer Waveguide Grating Filters," *Applied Optics,* 34(14):2414-2420, 1995.

Wang and Magnusson, "Design of waveguide-grating filters with symmetrical line shapes and low sidebands," *Optics Letters,* 19:919-921, 1994.

Wang and Magnusson, "Theory and applications of guided-mode resonance filters," *Applied Optics,* 32: 2606-2613, 1993.

Wang, et al., "Self-referenced fiber optic sensor for micro-displacement measurement," *Optical Engineering,* 34(1): 240-243, 1995.

Wawro, et al., "Optical fiber endface biosensor based on resonances in dielectric waveguide gratings," Intl Biomedical Optics Symposium, Photonics West, San Jose, Calif., January 2000, Proceedings SPIE, 3911:86-94, May 2000.

Wawro, Debra, M. S. Thesis, The University of Texas at Arlington, December 1999.

Zuffada, et al. "Synthesis of novel all-dielectric grating filters using genetic algorithms," IEEE Transaction on Antennas and Propagation, 46:657-663, 1998.

Zuffada, et al., "Designing dielectric grating filters with PGAPACK," *Electromagnetic System Design using Evolutionary Optimization: Genetic Algorithms*, edited by Y. Rahmat-Samii and E. Michielssen, John Wiley and Sons, 1999.

APPENDIX

Principles of Genetic Algorithm Search and Optimization

An important characteristic feature of genetic algorithms is that they operate on a coding (e.g., a binary coding) of the parameters rather than on the parameters themselves [77, 104-108]. Thus, the first task of a genetic algorithm is to generate a set of random numbers in a particular encoding that corresponds to the variables of the problem. Each variable is called a "gene" or "allele" and represents a particular feature or character such as, for instance, the thickness or refractive index of a layer in a diffractive optics problem. By combining several genes one obtains a string called a "chromosome," which represents a candidate solution. For example, in a homogeneous-layer thin-film optimization procedure a chromosome would be composed of the thicknesses and the refractive indices of all the layers in a structure. Many such candidate solutions are generated simultaneously by a genetic algorithm. Together they form a "population," and successive populations generated by the genetic algorithm are referred to as "generations."

Figure 24:
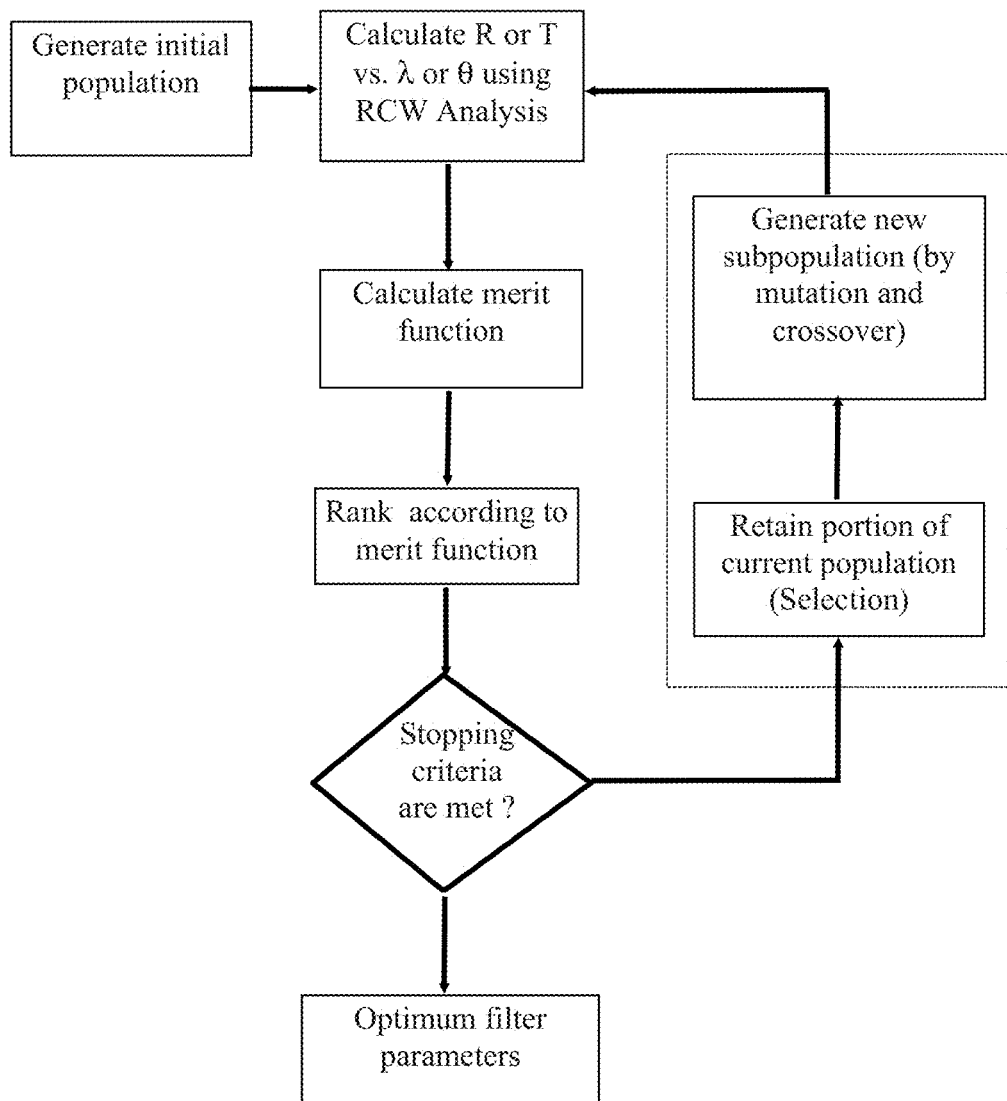
FIG. 24 (see Appendix). Flow chart of a genetic algorithm using rigorous coupled-wave analysis for merit function evaluation [77]. The program uses the library PGAPACK [110] to perform specific genetic algorithm operations such as mutation, crossover, selection, ranking, and generation of new chromosomes.

There are many implementations of genetic algorithms, but they all have in common the basic operators of selection, crossover, and mutation [77,104-108]. All these operators are applied on the population of a generation to create the next generation. A typical flow chart for a genetic algorithm optimization procedure is presented in FIG. 24. An initial population is generated randomly with each gene spanning its allowed range of values. The domain can be discrete for some genes and continuous for others, the only restriction consisting in the locations of the genes in the chromosome, which must remain the same for all chromosomes. A merit (sometimes referred to as cost, fitness, or residual) function is calculated for each chromosome. This merit function is problem specific and the success of the optimization procedure depends largely on the choice of the merit function. The chromosomes are ranked in terms of their performance evaluated by the merit function. Successive generations are then created by retaining a part of the chromosomes from one generation to the next and by forming new chromosomes through recombination of the best chromosomes in the old population. The greater the fitness value of a chromosome, the more likely it is to participate in the recombination process. Some algorithms retain a fixed number of chromosomes [110] while others are more problem-specific and retain all chromosomes with fitness better than a user-defined value [111].

Figure 25:
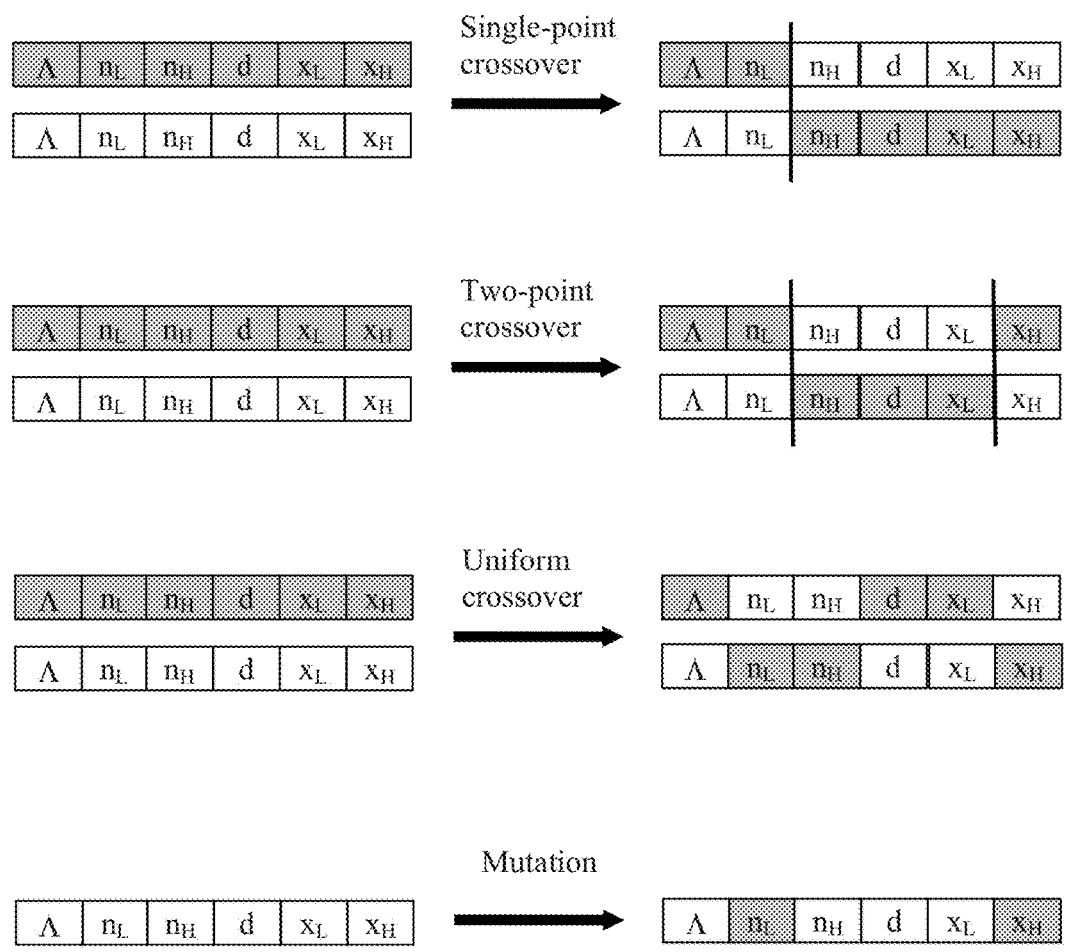
FIG. 25 (see Appendix). Crossover and mutation operations illustrated for chromosomes composed of 6 genes encoded as real numbers. In the 3 types of crossover operations shown here genes of the parent chromosomes (white and grey) are exchanged to yield new chromosomes. In the mutation operation, one or more genes are randomly changed from one value to another.

The recombination process consists of applying either or both crossover and mutation operators. In the crossover operation, two chromosomes exchange portions of their encoded representation. The three types of crossover mechanisms encountered in genetic algorithms are illustrated in FIG. 25. A single-point crossover is realized by choosing a point in the chromosome chains at random and exchanging the data to the right of this point between the parent chromosomes. In the two-point crossover the data between two randomly selected points is swapped while in the multiple-point crossover data is exchanged at random between the two parent chromosomes. Higher ranked strings will be more likely to participate in the crossover and thus form new chromosomes.

The crossover operation is a random but structured information exchange between chromosomes and represents the essential tool in local searches, (i.e., in exploring points within the hyperplanes already represented in the population) [105]. However, crossover alone would produce convergence in local extrema and, to explore other points in space and avoid "premature convergence," the mutation operator is introduced in the genetic algorithm.

A mutation is the random change of a gene from one value to another. Mutation is carried out with a user-defined probability and according to the statistical rules implemented in the genetic algorithm program. Mutation has a very important role in the search process ensuring variability in the population and hence, avoiding the entrapment of the algorithm in local extrema of the merit function.

The operators of selection, crossover and mutation are independent of the application, and only the merit function contains domain-specific knowledge. Another operator utilized in some genetic algorithms to diversify the search is the restarting operator. After a number of generations the best string is retained while all the others are discarded, and the whole population is reseeded as mutant variations of the best string. For the same purpose of avoiding premature convergence, other genetic operators introduce a random disturbance in every chromosome of a population after a number of generations or when all chromosomes have reached the same set of genes.

The genetic algorithm ends after a user-determined fixed number of iterations, when the merit function has reached an extremum that is close enough to the desired value, or when all chromosomes in a population have merit functions within a small enough range.

Genetic Algorithm Program for Multilayer Waveguide Gratings

Program Description

A genetic algorithm program has been developed for optimization of diffractive optics structures with multiple homogeneous and grating layers and incident TE polarized plane waves [65,71,77]. The program employs rigorous coupled-wave analysis for calculation of the reflected and transmitted diffraction efficiencies [84-86] and, hence, for evaluation of the merit function for the generated structures. The software library PGAPack [110i] performs specific genetic algorithm operations (chromosome generation, ranking, selection, crossover, mutation, etc.)

The algorithm seeks to find the physical parameters of the diffractive structure that generates the spectral dependence of the zero-order reflected (or transmitted) diffraction efficiency provided by the user in a reference data file. Alternatively, the optimization can be performed for the angular dependence of the diffraction efficiency and at a fixed wavelength of the incident light. The physical parameters to be found in the optimization process are the grating period, the refractive indices, and the thicknesses of the layers, the fill factors, and relative spatial phase shifts of the gratings. The refractive indices of the cover and substrate, the angle of incidence (or the wavelength for angular dependence optimization), the maximum number of layers, and the minimum and maximum values for the thicknesses, fill factors, and grating period are required as input parameters to the program. The refractive indices of the candidate solutions are selected from a list of discrete values supplied by the user in a separate input file. All other physical parameters (grating period, fill factors, thicknesses) are allowed to vary continuously within the ranges established by the user. Therefore, the program seeks the minimum of the merit function in a mixed discrete and continuous parameter space. This is a practical approach since in fabrication of diffractive optical structures only a limited number of materials can be used in a given spectral range while the thicknesses, fill factors, and the grating period can be varied continuously within a range, and within the accuracy limitations of the equipment. In some applications one or more of the physical parameters may be fixed due to either fabrication constraints (e.g., fill factor of the grating equal to 0.5) or user knowledge about the physics of the problem (e.g., known grating period for center wavelength of resonance filters). This feature is included in the program and will expedite the search procedure by reducing the dimension of the parameter space. A priori information can also simplify the search procedure by reducing the range over which a parameter can vary during optimization, thereby reducing the total number of points in the parameter space.

The physical parameters of the diffractive structure can be encoded as binary, binary Gray, or real numbers [110]. For binary and binary Gray representations of real and integer numbers, the user must specify the number of bits for encoding the thicknesses, the grating period, the fill factors, and the refractive indices. The number of bits allocated for each variable determines the accuracy of the representation of real numbers. Increasing the accuracy allows a better solution to be found but at the same time increases the total number of points in the parameter space decreasing the convergence. The binary and the binary Gray encodings allow the genetic algorithm to access and operate on individual bits of a gene, instead of the gene as a whole as in the real encoding [110]. For instance, a single-point crossover operation may take place with the crossover point in the middle of a gene in the binary encodings but only between genes in the real encoding. The Gray binary encoding differs from the binary encoding in that consecutive integer numbers differ by only one bit. This difference induces different paths in the genetic algorithm optimization procedure. For instance, mutation of one bit in a gene produces an incremental change in the value of the corresponding physical parameter if it is represented in Gray code, but may lead to a large variation in the case of binary encoding.

Figure 26A:
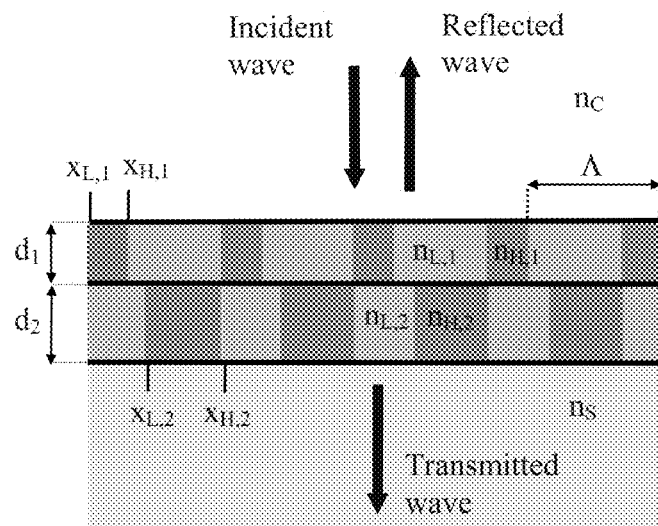
FIGS. 26A and 26B (see Appendix). Example of a diffractive structure consisting of two gratings in two separate layers, with physical parameters shown in FIG. 26A and corresponding chromosome represented in FIG. 26B. The chromosome is a candidate solution in the optimization process. A set of chromosomes forms a population. The total population of chromosomes at a given iteration is called a generation. In this case, the parameters to be optimized are the grating period $\Lambda$, the thicknesses $d_1$, $d_2$, refractive indices, $n_{L,1}$, $n_{H,1}$, $n_{L,2}$, $n_{H,2}$, and relative positions of the high-refractive index materials within a grating period, $x_{L,1}$, $x_{H,1}$, $x_{L,2}$, and $x_{H,2}$.
Figure 26B:
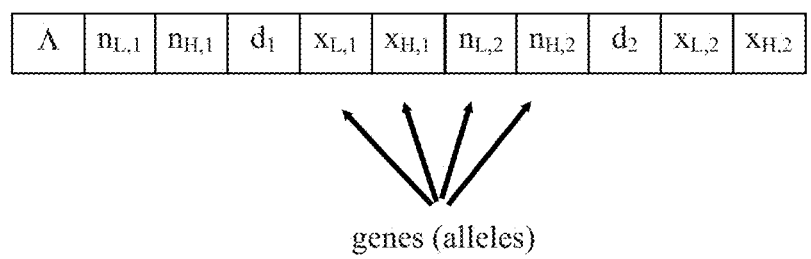

The program starts by randomly generating a population of chromosomes in the specified encoding and range of values for each variable. As an example, FIG. 26B shows the chromosome of a double-layer grating with its genes corresponding to the physical parameters of the structure illustrated in FIG. 26A [65,71]. The chromosome has ($5N_L+1$) genes where $N_L$ is the number of layers of the diffractive structure. Each layer is assumed to be a grating with the same period A, but with different refractive indices $n_H$ and $n_L$, thicknesses d, and coordinates (relative to the grating period) of the high-refractive index region of each grating $X_L$ and $X_H$. To select the refractive indices in each layer, the algorithm generates integer random numbers, which represent pointers to refractive index values in the corresponding input file. Homogeneous layers are generated either when the same refractive index is selected for both regions of the binary grating, or when the fill factor defined as ($X_H-X_L$) is smaller or greater than the values specified by the user in the input file $f_{min}$ and $f_{max}$. For ($X_H-X_L$)<$f_{min}$ the layer is considered as homogeneous with the refractive index $n_L$, while for ($X_H-X_L$)>$f_{max}$ the layer is homogeneous with refractive index $n_H$. Different values of $X_L$ in different layers generate phase-shifted layers. The number of layers $N_L$ is fixed and provided by the user. However the program can analyze structures with fewer layers whenever it selects a layer thickness that is smaller than the minimum layer thickness (from the input file). In this case, the thickness is set to zero and the number of layers decreases by one.

The number sequence forming a population of strings is unique for each run of the program. A feature is included that allows the same number sequence to be generated each time for debugging or reproducibility purposes [110]. In binary representation, each bit of a string has equal probabilities of being set to 0 or 1. In the real encoding the genes are set to a value selected uniformly within the user-specified range.

The population (i.e., the total number of chromosomes generated in the beginning, which is to remain constant after each iteration) is established by the user depending on the dimension of the search space and the length of the chromosome. An increased number of genes and/or a large range of variation for the genes may require a large population for effective optimization. Operating with larger populations, the genetic algorithm is more likely to find the global minimum of the merit function since it searches more regions of the space simultaneously. However, this is achieved at the expense of an increase in computational time, which imposes a practical limitation on the population size.

The initially generated population is evaluated by calculating a merit function for each chromosome as the deviation between the synthesized value of reflected (or transmitted) zero-order diffraction efficiency and the desired one. The genetic algorithm searches for the global minimum of the following merit function $$MF = \left[\frac{1}{M}\sum_{i=1}^{M} w_i |DE_{GA,i} - DE_{ref,i}|^n\right]^{1/n} \quad (5.1)$$

where $DE_{GA,i}$ are zero order reflected (or transmitted) diffraction efficiency values calculated with rigorous-coupled wave analysis for the structure generated by the genetic algorithm, $DE_{ref,i}$ are the reference data points, M is the total number of target values, $w_i$ are the weight factors, and n is the power index of the merit function. The target points represent either a wavelength or an angular dependence of a diffraction order efficiency. Any diffraction order may be selected for optimization, but for the applications of interest to this work concerning only zero-order gratings, the zero-order efficiencies are utilized. The power index of the merit function can take any integer values but in thin-film optics optimization routines the most common value is n=2. Different values of n, can affect the optimization results due to changes induced in the relative contributions of individual target deviation points $|DE_{GA,i}-DE_{ref,i}|$ to the merit function. For larger values of n higher deviations, will be emphasized and the merit function becomes more sensitive to nonequal deviations forcing the genetic algorithm to find a more uniform approximation to the reference data [96].

Once the merit function has been calculated, the chromosomes are ranked from the best-fit to the least-fit, with the best-fit possessing the lowest merit function. A number of chromosomes are retained while others are replaced by newly generated chromosomes. The selection mechanism typically used is the tournament selection consisting in retaining the best chromosomes of a population. Other selection mechanisms such as probabilistic tournament (with an associated probability of selecting a chromosome), proportional and stochastic universal selection can also be chosen for use in the optimization procedure [110]. The number of chromosomes replaced is an input parameter to the program and has an important influence on the optimization progress. A high percentage of chromosomes replaced provides more new points for fitness testing which is beneficial in the search procedure, but it will also increase the computation time. It is also possible that a large replacement will cause the elimination of certain chromosomes that, after subsequent crossover and mutation, would have generated the optimum solution. Therefore, several convergence tests need to be performed to establish the optimum population replacement for a specific problem [77].

The new population that replaces the discarded chromosomes is formed by crossover and mutation of the chromosomes that are retained from the old generation [110]. The chromosomes that survive become parents and generate enough chromosomes to maintain the total population constant from one generation to another. The algorithm allows the user to decide whether a string can undergo both crossover and mutation or just one of the two operations.

In the case where either crossover or mutation is carried out, the probability of going towards one or the other operation is decided by a random logical variable that has an associated flip probability (provided in the input file) of returning a logical value "true." A probability of 0.5 corresponds to flipping an unbiased coin. In the case when both mutation and crossover are performed, the random logical value of the flip probability determines whether crossover is executed first followed by a mutation operation or vice versa [110].

Crossover takes place by pairing the chromosomes selected to survive from the old generation into the new one from top to bottom of the list (with best-ranked strings at the top). The crossover operation is performed with a probability defined by the user in the input file. The algorithm has the options of single-point, two-point or uniform crossover (FIG. 25). For the latter type of crossover, the probability of swapping two parent bits (or genes in case of real encoding) called uniform crossover probability, must be specified in the input file.

Mutation takes place with a probability defined by the user in the input file. For binary encoding, mutation is performed by replacing one or more of the bits of a chromosome with its complement. For real encoding, the mutation occurs for one or more genes of a chromosome and can be one of several types: "range," "constant," "uniform," or "Gaussian" [110]. If the mutation is of the "range" type, the gene will be replaced with a number selected with equal probability from the allowed range of variation for the gene. In the other three mutation types the gene g is replaced by g±p×g where the value of p is determined differently for each mutation operator. For constant mutation, p is a constant provided by the user. Uniform mutation occurs when p is selected uniformly from an interval $[0-M_u]$ where $M_u$ is an input parameter. In the Gaussian type of mutation p is generated by a Gaussian distribution with mean 0 and standard deviation σ given in the input file.

After generating a new pair of chromosomes through crossover and/or mutation, the algorithm performs a verification to determine whether they are different from their parent chromosomes. If the new chromosome is identical to the parent chromosome, the mutation operator is applied to the new chromosome until at least one mutation has occurred.

After evaluation of the newly generated chromosomes and ranking the new generation, the process of selection, crossover, and mutation is repeated until the stopping criteria is met. This can be determined by a fixed number of iterations, no change in the best string after a number of iterations, or when certain fraction of the population has the same merit function [110]. The genetic algorithm also has the restarting option by which the best string is kept and all others are generated as mutants of the best string. The number of iterations between restarting operations is defined by the user.

The program prints the best $N_{out}$ chromosomes and their corresponding merit functions in the output file, where $N_{out}$ is an input parameter. By printing a number of the top chromosomes, the user can asses the distribution of solutions and hence the degree of convergence of the algorithm. A large dispersion in the gene values of the final chromosomes indicates that the algorithm has not yet converged and changes need to be made in the input parameters of a future run. Typical changes would be to try more iterations, larger populations, or impose more constraints according to a priori knowledge about the physics of the problem [111]. However changes in other genetic algorithm input parameters can also improve the convergence and the effectiveness of the optimization.

Convergence Tests

The genetic algorithm developed in this work has a general applicability. The genetic operators and optimization procedure can be utilized in any optimization task involving multilayer structures containing gratings and homogeneous layers, with minor modifications pertaining to the encoding and decoding of the chromosomes. The merit function evaluation subroutines can be applied to optimization of any structure that can be modeled with the rigorous coupled-wave analysis.

However, the optimum set of the program-input parameters may be problem specific due to the dimension of the solution space and the particular variation of the merit function in the parameter space. To determine the influence of the input parameters on the optimization procedure and final result, and to find some guidelines for selecting the appropriate set of input parameters for a specific application, it is important to study the evolution of the optimization process (i.e., the convergence) for various starting conditions [65,77].

In this section, the convergence of the merit function is studied as a function of key genetic-algorithm parameters such as the population replaced at each iteration, mutation probability, type of encoding, number of generations, population size, for the same problem. In all tests discussed here, the program is required to design a single-layer guided-mode resonance reflection filter with the response specified in the input file by the spectral dependence of the zero-order reflection diffraction efficiency. This reference data is generated with the rigorous coupled-wave theory for a single-layer grating with the following physical parameters: grating period $\Lambda=314$ nm, thickness $d=134$ nm, fill factor $f=0.5$, refractive indices of the grating: $n_H=2.1$ and $n_L=2.0$, refractive indices of the cover and substrate: $n_C=1.0$ and $n_S=1.52$, and normally incident, TE polarized plane wave. The optimization is performed in terms of the layer thickness, fill factor and refractive indices of the grating over a wavelength range 0.546-0.554 µm. The grating period is fixed at the value $\Lambda=314$ nm, the cover and substrate refractive indices have constant values of $n_C=1.0$ and $n_S=1.52$, respectively, and the incident angle is set at $\theta=0°$. The allowed range for fill factor optimization is between 0.1-0.9 and the thickness range is 50-350 nm. Throughout the tests the algorithm uses the same set of 13 refractive indices with values from 1.3-2.5 in increments of 0.1. The materials are assumed to be lossless although the program can handle lossy grating structures as well.

Comparing the merit function values for tests with the three different types of crossover, it was found that multiple crossover yields the best results in comparison with the single-point and two-point crossover operators. The crossover probability was maintained at 0.8 and the uniform crossover probability was 0.5 for all tests performed. Other genetic algorithm parameters kept constant for all tests were the flip probability equal to 0.5, the tournament selection type, and maximum iteration as the stopping criterion.

The tests performed with populations of 500 and 1000 chromosomes indicate that although fast convergence and low merit function values are also possible with a smaller number of chromosomes, for certain values of the genetic algorithm parameters, the larger population is generally expected to yield lower merit functions, for all other parameters being constant. However, in some cases the increased computation time for larger populations may not be rewarded by a substantial decrease in merit function and an optimum population has to be determined for a typical chromosome length and search space. It has been observed that larger populations also provide the algorithm with less sensitivity to the other input parameters, and therefore fewer trials are required to determine the optimum set of genetic algorithm parameters.

A more detailed investigation of the convergence sensitivity to genetic algorithm parameters was performed for the population replacement and the mutation probability, contrasting real versus binary and Gray encoding performance [77]. Hence, the population size was fixed at 500, the crossover type was uniform with probability fixed at 0.8, and the number of generations and mutation probability were varied. For the real encoding the mutation type was chosen to be Gaussian with standard deviation $\sigma=0.1$. In all cases the newly created strings were specified to undergo both crossover and mutation. When using binary or Gray encoding, 10 bits were chosen to represent the thickness, 10 bits to represent the fill factor, and 4 bits to represent the pointer to the set of materials. In this case uniform crossover with probability 0.8 was chosen. The number of generations was taken to be 400, to ensure that convergence had been reached.

After performing at least four runs for the same set-up, with different random number sequences in the genetic algorithm functions to seed the population, in order to construct a statistically significant sample of the outcomesit was noted that the real encoding produced smaller merit functions, therefore indicating that for this problem it is better suited than the others. Overall, the sensitivity to replacement values over the range 50-250 chromosomes was not very strong considering the total distribution of results. In the case of real encoding, on average, the lowest merit function was obtained for a replacement value of 150. In the case of binary and Gray encodings, slightly smaller merit functions were achieved for the replacement value of 250. However, this replacement also produced a large spread of the residuals indicating that a poor solution can obtained as well as a good one.

Turning to the behavior of the residual as a function of increasing values of mutation probability, for the binary and Gray encoding, a replacement value of 50 was used, whereas for the real encoding the value was 200. Otherwise, the same genetic algorithm parameters as discussed above were retained. The binary and Gray encoding results were not very sensitive to the value of mutation probability. However, on average, the binary encoding favored lower mutation probabilities than the real encoding, which benefits from an increase in the value of this parameter to 1. In the real encoding, the mutation operator was applied to the gene as a whole, which, for the structures studied here, are represented by 4 numbers. In the binary encoding, mutation took place at the level of individual bits (e.g., for a representation of the filter parameters (d, f, $n_H$, $n_L$) with (10, 10, 4, 4) bits, the mutation is applied individually to all of the 28 bits of the chromosome with the specified mutation probability).

Therefore, for the mutation to be active in the search procedure with the real encoding, the mutation probability must be higher than in the binary case where a low probability is compensated by the larger number of elements (bits) to which it is applied. The differences observed between the binary and the real encodings were also due to the different manner in which mutation was carried out. In the real encoding, the Gaussian mutation did not change the gene value by an arbitrarily large amount as in the binary case, but applied a random change in a limited range (determined by σ) around the value of the gene.

Thus, in the real encoding, mutation performed a more localized search alongside the crossover operator before shifting to a different region of space and was able to find a global minimum with greater accuracy. It was found that mutation probabilities of 1 were detrimental in the binary encoding due to the rapid changes occurring in the best chromosomes, which prevented the fine tuning performed by crossover. On average, very low mutation probabilities (0.001) produced equally poor results by precluding the algorithm from exploring new regions in the parameter space.

Turning to the convergence history for three different values of number of chromosomes replaced at each generation (i.e., 50, 150 and 250), when increasing this number, note that the value of the merit function at convergence was reached after a decreasing number of generations. While the computational burden increased with the increase of the chromosomes replaced per generation, this was offset by the ability to reach convergence in fewer generations.

Therefore, the total amount of calculations necessary to reach convergence was similar in all cases. Note that the real encoding generally provided lower merit functions than the binary and Gray encodings. The high sensitivity of the guided-mode resonances to structural parameters was equivalent to a rugged search space for the genetic algorithm with multiple and narrow local extrema. Therefore, the improved fine-tuning performed by the mutation operator in the real encoding lead to superior convergence results.

The number of reference reflectance vs. wavelength points has been found to significantly influence the final result of the optimization process. It is well known from homogeneous thin-film optimization techniques that more "targets" typically lead to improved results due to the additional information supplied by the user [94].

The number of data points was an even more critical parameter in the design of grating devices that exhibit sharp variations in the reflectance and transmittance spectral dependence. In this case, the global minima of the merit function can not be reached if insufficient target data is provided. In reference 112, for instance, the micro-genetic algorithm uses only one reference point with zero-order reflectance equal to 1 at the wavelength $\lambda=1.0$. The resulting structure exhibits an almost 100% peak at $\lambda=1.0$ but other high-efficiency peaks are also present in the proximity of the desired peak thus limiting the filter range. The side peaks can be eliminated in the optimization process by providing the merit function with more reference reflectance points. In the present work, between 40-80 reference data points were used. The major drawback of the increased number of target data was the increased computation time.

The distribution of reference reflectance points in the spectral range of interest was also important in the search for an optimum design. In the case of the rapidly varying reflectance characteristics studied here, it was advantageous to use unequally spaced data points with more reflectance values in the resonance spectral region and less in the sidebands. Utilizing this type of distribution, the algorithm was able in all tests to find a resonance and typically within ±0.1 nm of the reference reflectance peak.

A different method to emphasize some reference points over others is to introduce different weight factors. Increased values of the weight factors in some reference points will raise the accuracy in these spectral regions at the expense of a larger target deviation in wavelength regions considered of lesser importance.

REFERENCES

The following references, to the extent that they provide exemplary procedural or other details supplementary to those set forth herein, are specifically incorporated herein by reference.

[65] S. Tibuleac, D. Shin, R. Magnusson, and C. Zuffada, "Guided-mode resonance filters generated with genetic algorithms," Proceedings of the Topical Meeting on Diffractive Optics and Micro-Optics, Kailua-Kona, Hi., June 1998, Conference Proceedings, vol. 10, pp. 24-26, 1998.

[71] S. Tibuleac, D. Shin, R. Magnusson, and C. Zuffada, "Design of reflection and transmission guided-mode resonance filters with genetic algorithms," Optical Society of America Annual Meeting, Baltimore, Md., October 1998, Conference Proceedings, p. 128, 1998.

[77] C. Zuffada, D. Levine, and S. Tibuleac, "Designing dielectric grating filters with PGAPACK," Electromagnetic system design using evolutionary optimization: genetic algorithms, edited by Y. Rahmat-Samii and E. Michielssen, John Wiley and Sons, 1999.

[84] T. K. Gaylord and M. G. Moharam, "Analysis and applications of optical diffraction by gratings," Proc. IEEE, vol. 73, pp. 894-937, May 1985.

[85] M. G. Moharam, E. B. Grann, D. A. Pommet, and T. K. Gaylord, "Formulation for stable and efficient implementation of the rigorous coupled-wave analysis of binary gratings," J. Opt. Soc. Am. A, vol. 12, pp. 1068-1076, May 1995.

[86] M. G. Moharam, D. A. Pommet, E. B. Grann, and T. K. Gaylord, "Stable implementation of the rigorous coupled-wave analysis for surface-relief gratings: enhanced transmittance matrix approach," J. Opt. Soc. Am. A, vol. 12, pp. 1077-1086, May 1995.

[94] TFCalc manual, Thin Film Design Software for Windows, Version 3.0, Software Spectra, Inc., 1995.

[96] Sh. A. Furman, and A. V. Tikhonravov, *Basics of Optics of Multilayer Systems*, Editions Frontieres, Paris, 1992.

[104] D. Goldberg, *Genetic Algorithms in Search, Optimization, and Machine Learning*, Addison-Wesley, Reading, Mass., 1989.

[105] B. P. Buckles and F. E. Petry, *Genetic Algorithms*, IEEE Computer Society Press, Los Alamitos, Calif., 1992.

[106] L. Davis, Ed., *Genetic Algorithms and Simulated Annealing*, Pitman, London, 1987.

[110] D. Levine, "Users guide to the PGAPack parallel genetic algorithm library," Argonne National Laboratory, ANL 95/18, January 1996.

[111] R. L. Haupt, "An introduction to genetic algorithms for electromagnetics," IEEE Antennas and Propagation Magazine, vol. 37, pp. 7-15, April 1995.

[112] E. G. Johnson and M. A. G. Abushagur, "Microgenetic-algorithm optimization methods applied to dielectric gratings," J. Opt.

What is claimed is:
1. A method of using a waveguide grating, comprising:
 contacting a waveguide grating device with a medium, the waveguide grating device comprising:
  at least one waveguide having an end, the end having an endface; and a waveguide grating fabricated on the endface of the at least one waveguide, the waveguide grating having at least one waveguide layer and at least one grating layer;

where the contacting comprises contacting the waveguide grating with the medium;

directing light through the at least one waveguide such that the light contacts the waveguide grating, the waveguide grating being configured such that:

at least one attribute of the light is consequently modified; and a guided-mode resonance peak or minimum occurs in light that is reflected from the waveguide grating or in light that is transmitted through the waveguide grating; and determining at least one parameter of the medium using the modified attribute.

2. The method of claim 1, wherein the light is directed from a laser.

3. The method of claim 1, wherein the light is directed from a broadband source.

4. The method of claim 1, wherein the light is directed from a light emitting diode.

5. The method of claim 1, wherein the determining involves the use of an optical spectrum analyzer.

6. The method of claim 1, wherein the at least one attribute comprises the spectral content of the light.

7. A method of using a waveguide grating as a biosensor, comprising:

contacting a guided-mode resonance waveguide grating with a medium, the guided-mode resonance waveguide grating having at least one waveguide layer, at least one grating layer, and biologically sensitive material;

directing light from a broadband source toward the guided-mode resonance waveguide grating such that the light contacts the waveguide grating, the guided-mode resonance waveguide grating being configured such that at least one attribute of the light is consequently modified; and determining at least one parameter of the medium using the modified attribute.

* * * * *

UNITED STATES PATENT AND TRADEMARK OFFICE
CERTIFICATE OF CORRECTION

PATENT NO. : 10,359,573 B2  Page 1 of 1
APPLICATION NO. : 13/971737
DATED : July 23, 2019
INVENTOR(S) : Debra Weidanz et al.

It is certified that error appears in the above-identified patent and that said Letters Patent is hereby corrected as shown below:

On the Title Page

Item (54) and in the Specification Column 1 Lines 1-3 the correct title should be "RESONANT WAVEGUIDE-GRATING DEVICES AND METHODS FOR USING SAME."

Item (12) and item (72) the name of the first named inventor should be "DEBRA WEIDANZ.".

Signed and Sealed this
Eighth Day of September, 2020

Andrei Iancu
*Director of the United States Patent and Trademark Office*